United States Patent [19]

Brown et al.

[11] Patent Number: 5,288,619

[45] Date of Patent: Feb. 22, 1994

[54] ENZYMATIC METHOD FOR PREPARING TRANSESTERIFIED OILS

[75] Inventors: Peter H. Brown, Morton Grove; Federico D. Carvallo, Wheeling; Robert C. Dinwoodie; Michael T. Dueber, both of Glenview; David K. Hayashi, Chicago; R. G. Krishnamurthy, Glenview; Zohar M. Merchant, Wilmette; James J. Myrick, Glencoe; Richard S. Silver, Wilmette; Chrisanthus Thomas, Arlington, Heights, all of Ill.

[73] Assignee: Kraft General Foods, Inc., Northfield, Ill.

[21] Appl. No.: 897,255

[22] Filed: Jun. 11, 1992

Related U.S. Application Data

[63] Continuation-in-part of Ser. No. 714,432, Jun. 13, 1991, abandoned, which is a continuation-in-part of Ser. No. 455,551, Dec. 18, 1989, abandoned, and Ser. No. 700,115, May 9, 1991, abandoned, which is a continuation of Ser. No. 455,555, Dec. 18, 1989, abandoned.

[51] Int. Cl.$^5$ ............................ C12P 7/64; C12P 7/58; A23D 7/00; A23D 9/00
[52] U.S. Cl. ........................................ 435/134; 426/33; 426/601; 426/607; 426/603; 435/137
[58] Field of Search ................... 435/134, 137; 426/33, 426/601, 607, 603

[56] References Cited

U.S. PATENT DOCUMENTS

| | | | |
|---|---|---|---|
| 1,687,050 | 10/1928 | Yamamoto | 435/198 |
| 2,200,390 | 5/1940 | Freeman | 260/412.4 |
| 2,219,652 | 10/1940 | Hixson et al. | 260/419 |
| 2,278,309 | 3/1942 | Freeman | 260/419 |
| 2,285,795 | 6/1942 | Batchelder | 260/428 |
| 2,290,609 | 7/1942 | Goss et al. | 260/411 |
| 2,291,461 | 7/1942 | Freeman | 260/428 |
| 2,313,636 | 3/1943 | Freeman | 260/419 |
| 2,316,512 | 4/1943 | Freeman | 260/428 |
| 2,320,738 | 6/1943 | Jenkins | 260/428 |
| 2,480,090 | 8/1949 | Smythe et al. | 195/66 |
| 2,539,661 | 1/1951 | Freeman et al. | 260/428.5 |

(List continued on next page.)

FOREIGN PATENT DOCUMENTS 1178549  11/1984  Canada .................... 195/131

(List continued on next page.)

OTHER PUBLICATIONS

Macrae, "Enzyme-catalysed modification of oils and fats," *Phil. Trans. R. Soc. Lond.*, B 310, 227–233 (1985).
Macrae, "Lipase-Catalyzed Interesterification of Oils and Fats," *JAOCS*, vol. 60, No. 2, 291–294 (1983).

(List continued on next page.)

*Primary Examiner*—David M. Naff
*Assistant Examiner*—Michael V. Meller
*Attorney, Agent, or Firm*—Fitch, Even, Tabin & Flannery

[57] ABSTRACT

An enzymatic transesterification method for preparing a margarine oil having both low trans- acid and low intermediate chain fatty acid content is disclosed. The method includes the steps of providing a transesterification reaction mixture containing a stearic acid source material and an edible liquid vegetable oil, transesterifying the stearic acid source material and the vegetable oil using a 1-, 3-positionally specific lipase, and then finally hydrogenating the fatty acid mixture to provide a recycle stearic acid source material for a recyclic reaction with the vegetable oil. Also described is a counter-current method for preparing a transesterified oil. The method includes the steps of providing a transesterification reaction zone containing a 1-, 3-positionally specific lipase, introducing a vegetable oil into the transesterification zone, introducing a stearic acid source material, conducting a supercritical gas or subcritical liquified gas counter-current fluid, carrying out a transesterification reaction of the triglyceride stream with the stearic acid or stearic acid monoester stream in the reaction zone, withdrawing a transesterified triglyceride margarine oil stream, withdrawing a counter-current fluid phase, hydrogenating the transesterified stearic acid or stearic acid monoester to provide a hydrogenated recycle stearic acid source material, and introducing the hydrogenated recycle stearic acid source material into the reaction zone.

5 Claims, 14 Drawing Sheets

U.S. PATENT DOCUMENTS

| | | | |
|---|---|---|---|
| 2,573,900 | 11/1951 | Freeman | 260/428.5 |
| 2,676,906 | 4/1954 | Rose et al. | 195/66 |
| 2,688,626 | 9/1954 | Miller | 260/410.7 |
| 2,794,743 | 6/1957 | Farnham | 99/56 |
| 2,812,324 | 11/1957 | Huber et al. | 260/234 |
| 2,924,555 | 2/1960 | Reese | 195/116 |
| 2,985,589 | 5/1961 | Broughton et al. | 210/34 |
| 3,012,890 | 12/1961 | Dutton et al. | 99/118 |
| 3,190,753 | 6/1965 | Claus et al. | 99/54 |
| 3,201,491 | 8/1965 | Stine et al. | 260/676 |
| 3,376,326 | 4/1968 | Artman et al. | 260/410.7 |
| 3,492,130 | 1/1970 | Harwood | 99/118 |
| 3,498,882 | 3/1970 | Rogols et al. | 195/7 |
| 3,519,538 | 7/1970 | Messing et al. | 195/63 |
| 3,666,627 | 5/1972 | Messing | 195/68 |
| 3,748,348 | 7/1973 | Sreenivasan | 260/410.7 |
| 3,859,447 | 1/1975 | Sreenivasan | 426/73 |
| 3,878,231 | 4/1975 | Harwood | 260/410.7 |
| 3,909,360 | 9/1975 | Horiuchi et al. | 195/68 |
| 3,925,158 | 12/1975 | Betzing et al. | 195/66 R |
| 3,926,726 | 12/1975 | Antonini et al. | 195/30 |
| 3,969,382 | 7/1976 | Zosel | 260/409 |
| 4,032,405 | 6/1977 | Tatsumi et al. | 195/82 |
| 4,048,205 | 8/1977 | Neuzil et al. | 260/248 |
| 4,049,688 | 9/1977 | Neuzil et al. | 260/248 |
| 4,061,724 | 12/1977 | Grose et al. | 423/335 |
| 4,062,882 | 12/1977 | Sen Gupta | 260/428.5 |
| 4,066,677 | 1/1978 | de Rosset et al. | 260/428.5 |
| 4,104,294 | 8/1978 | Grose et al. | 260/443 C |
| 4,156,688 | 5/1979 | Zosel | 260/420 |
| 4,213,913 | 7/1980 | de Rosset | 260/428.5 |
| 4,243,603 | 1/1981 | Klein et al. | 260/410.7 |
| 4,258,133 | 3/1981 | Mirabel et al. | 435/176 |
| 4,267,273 | 5/1981 | Smith | 435/44 |
| 4,268,527 | 5/1981 | Matsuo et al. | 426/33 |
| 4,275,011 | 6/1981 | Tanaka et al. | 260/410 |
| 4,275,081 | 6/1981 | Coleman et al. | 426/33 |
| 4,277,412 | 7/1981 | Logan | 260/428.5 |
| 4,329,280 | 5/1982 | Cleary et al. | 260/97.6 |
| 4,331,695 | 5/1982 | Zosel | 426/430 |
| 4,353,838 | 10/1982 | Cleary et al. | 260/419 |
| 4,364,868 | 12/1982 | Hargreaves | 260/410.7 |
| 4,402,832 | 9/1983 | Gernold | 210/659 |
| 4,404,145 | 9/1983 | Cleary et al. | 260/419 |
| 4,416,991 | 11/1983 | Matsuo et al. | 435/134 |
| 4,420,560 | 12/1983 | Matsuo et al. | 435/134 |
| 4,434,051 | 2/1984 | Golem | 210/264 |
| 4,451,565 | 5/1984 | Gatfield et al. | 435/117 |
| 4,472,503 | 9/1984 | Matsuo et al. | 435/180 |
| 4,478,721 | 10/1984 | Gerhold | 210/659 |
| 4,485,172 | 11/1984 | Gierhart | 435/134 |
| 4,498,991 | 2/1985 | Oroskar | 210/659 |
| 4,511,514 | 4/1985 | Cleary et al. | 260/419 |
| 4,519,952 | 5/1985 | Cleary et al. | 260/419 |
| 4,524,029 | 6/1985 | Cleary et al. | 260/419 |
| 4,529,551 | 7/1985 | Cleary et al. | 260/419 |
| 4,534,900 | 8/1985 | Cleary | 260/428.5 |
| 4,568,496 | 2/1986 | Kulkarni et al. | 260/428.5 |
| 4,578,223 | 3/1986 | Cleary et al. | 260/419 |
| 4,614,204 | 9/1986 | Dolejs | 137/625.11 |
| 4,614,205 | 9/1986 | Oroskar | 137/625.11 |
| 4,614,718 | 9/1986 | Seino et al. | 435/72 |
| 4,645,741 | 2/1987 | Inada | 435/134 |
| 4,650,783 | 3/1987 | Chao et al. | 502/407 |
| 4,719,178 | 1/1988 | Macrae et al. | 435/135 |
| 4,770,819 | 9/1988 | Zinnen | 260/428.5 |
| 4,784,807 | 11/1988 | Zinnen | 260/405.5 |
| 4,797,233 | 1/1989 | Zinnen | 260/428.5 |
| 4,798,793 | 1/1989 | Eigtved | 435/134 |
| 4,861,716 | 8/1989 | Macrae et al. | 435/134 |
| 4,873,109 | 10/1989 | Tanaka et al. | 426/601 |

FOREIGN PATENT DOCUMENTS

| | | | |
|---|---|---|---|
| 69599 | of 0000 | European Pat. Off. | |
| 0034065 | 8/1981 | European Pat. Off. | A23D 5/00 |
| 0035883 | 9/1981 | European Pat. Off. | C12P 7/64 |
| 0126416 | 11/1984 | European Pat. Off. | C11C 3/10 |
| 00134357 | 3/1985 | European Pat. Off. | C07C 51/47 |
| 0140542 | 6/1985 | European Pat. Off. | C12N 11/08 |
| 0170431 | 2/1986 | European Pat. Off. | C11C 3/10 |
| 0185524 | 6/1986 | European Pat. Off. | C11C 3/10 |
| 0105066 | 9/1986 | European Pat. Off. | C11C 1/08 |
| 0195311 | 9/1986 | European Pat. Off. | C11C 3/00 |
| 0326198 | 2/1989 | European Pat. Off. | A23D 5/00 |
| 50-025542B | 8/1975 | Japan | |
| 55-042532A | 3/1980 | Japan | |
| 60-201326 | 9/1985 | Japan | |
| 1431781 | 4/1976 | United Kingdom | A23D 5/00 |
| 1509543 | 5/1978 | United Kingdom | C11B 3/00 |
| 2033745A | 5/1980 | United Kingdom | A61K 31/23 |
| 1577933 | 10/1980 | United Kingdom | C11C 3/10 |
| PCT/GB82/00134 | 5/1982 | United Kingdom | C12P 1/00 |
| 2119397A | 11/1983 | United Kingdom | C11C 3/10 |
| 2159527A | 12/1985 | United Kingdom | C11C 3/10 |
| 2147004A | 5/1986 | United Kingdom | C11C 2/08 |
| 2168983A | 7/1986 | United Kingdom | C12N 9/20 |

OTHER PUBLICATIONS

Macrae, "Microbial Lipases as Catalysts for the Interesterification of Oils and Fats," *Biotechnology for the Oils and Fats Industry*, AOCS Publ., Colin Rutledge, Ed.; Chap. 17, 189–198 (1984).

(List continued on next page.)

OTHER PUBLICATIONS

R. A. Wisdom, P. Dunnill and M. D. Lilly, "Enzymic interesterification of fats: the effect of non-lipase material on immobilized enzyme activity," *Enzyme Mibrob. Technol.*, vol. 7, 567–572 (1985).

Nielsen, "Industrial Application Possibilities for Lipase," *Feete Seifen Anstrichmittel*, 87 Jahrgang Nr. 1 (1985).

Carrea, "Biocatalysis in Water-Organic Solvent Two--Phase Systems," *Trends in Biotechnology*, 2:4, pp. 102–106 (1984).

Freeman, "Understanding Enzyme Stabilization," *Biotech Workshop*, p. 147.

"The Omega—3 Solution Immobilized Lipases raise cod liver oil to new heights," *BioTimes*, 3: p. 2 (1988).

L. F. J. Woods, P. A. Gibbs, S. P. Kochhar and J. B. Rossell, "Biomodification of oils and fats—A literature review," *Scientific & Technical Surveys*, 152: (Jan., 1986).

Swern, "E. Urea Complexes," *Techniques of Separation*, p. 2309–2358.

Kimura, Tanaka, Sonomoto, Nihara and Fukui, "Application of Immobilized Lipase to Hydrolysis of Triacyclglyceride," *European J. Appl Microbiol Biotechnol*, (1983) 17:107–112.

Yokozeki, Yamanaka, Takinami, Hirose, Tanaka, Sonomoto and Fukui, "Application of Immobilized Lipase to Regio-Specific Interesterification of Triglyceride in Organic Solvent," *European J. Appl Microbiol Biotechnol*, (1982) 14:1–5.

Gatfield, "The Enzymatic Synthesis of Esters in Nonaqueous Systems," *Annals New York Academy of Sciences*, pp. 560–572.

Thomas, Magnuson, McCurdy and GrootWassink, "Enzymatic Interesterification of Canola Oil," *Canadian Institute of Food Science and Technology* (1988) 21:2, pp. 167–173.

Stevenson, Luddy and Rothbart, "Enzymatic Acyl Exchange to Vary Saturation in Di- and Triglycerides," *The American Oil Chem. Society*, 56:pp. 676–680, (Jul. 1979).

Sawamura, Norio et al., "Low-melting butter substitute manufacture by enzymatic interesterification," 17--Food, Feed Chem., vol. 107, (1987) 107:76474f, JP 62 61,589.

Klibanov, Samokhin, Martinen and Berezin, "A New Approach to Preparative Enzymatic Synthesis," *Biotechnology and Bioengineering*, vol. XIX, pp. 1351–1361 (1977).

Lavayre, Verrier, Baratti, "Stereospecific Hydrolysis by Soluble and Immobilized Lipases," *XXIV Biotechnology and Bioengineering*, pp. 2175–2187.

Tanaka, Ona, Ishihara, Yamanaka and Takinami, "Enzymatic Acyl Exchange of Triglyceride in n-Hexane," *Agric. Biol. Chem.*, 45 (10) pp. 2387–2389 (1981).

Butler, "Enzymes in Non-aqueous Solvents," *Enzyme Microb. Technol.*, pp. 253–259 (1979).

Goodnight, Jr., Harris, Conner and Illingworth, "Polyunsaturated Fatty Acids, Hyperlipidemia, and Thrombosis," *Arteriosclerosis*, 2: 87–113 (Mar./Apr. 1982).

Brunner and Peter, "On the Solubility of Glycerides and Fatty Acids in Compressed Gases in the Presence of an Entrainer," *Separation Science and Technology*, 1:199–214 (1982).

Kang and Rhee, "Effect of Water on Hydrolysis of Olive Oil by Immobilized Lipase in Reverse Phase System," *Biotechnology Letters*, 10: (5) 341–346, (1988).

Hoq, Yamane and Shimizu, "Continuous Synthesis of Glycerides by Lipase in a Microporous Membrane Bioreactor," *JAOCS*, 61:(4) 776–781 (Apr. 1984).

Hixon and Bockelmann, "Liquid-Liquid Extraction Employing Solvents in the Region of Their Critical Temperatures," *American Institute of Chemical Engineers*, pp. 890–930 (1942).

List, Friedrich and Pominski, "Characterization and Processing of Cottonseed Oil Obtained by Extraction with Supercritical Carbon Dioxide," presented at AOCS annual meeting, Chicago (May 1983).

Asahi Denka Kogyo K.K., "Cocoa butter substitute production by lipase," *Chem. Abstr.*, vol. 98 (1983) 98:522553, JP 57,111,398.

"Fatty acid ester production catalyzed by lipase," 16--*Fermentations*, vol. 103, 1985, 103:121766h, JP 60 78,587.

Kitamura, Keizo, "Production of cotton seed salad oil," *Chem. Abstr.*, vol. 106, 1987, 06:83306k, JP 61, 260,890.

Hiroto Yoshitaka et al., "Interesterification of oils and fats by lipase to hard butter manufacture," 17–*Food, Feed Chem.*, vol. 107, 1987, 107:38369t, JP 62 61,591.

(List continued on next page.)

OTHER PUBLICATIONS

Sawamura, Norio et al., "Enzymatic manufacture of hard butter having low diglyceride content," 17–*Food, Feed Chem.*, vol. 107, 1987, 107:38370m, JP 62 61,590.

Nakazato et al., "Alcohol carboxylic acid ester manufacture with lipase for foods," 17–*Food, Feed Chem.*, vol. 107, 1987, 107:3837n, JP 62 58,992.

Gancet, Guignard and Fourmentraux, "Catalysis by a Lipase-bearing *Rhizopus arrhizus* Mycelius in (Halogeno) Fluorinated Hydrocarbons," *Annals New York Academy of Science*, pp. 213–218.

Rheineck (Research Supervisor: Archer–Daniels–Midland Company, Minneapolis 2, Minn.), "Recent Advances in the Technology of Drying Oils," Chap. 8, pp. 165–262.

Alford, Pierce and Suggs, "Activity of microbial lipases on natural fats and synthetic triglycerides," *J. Lipid Res.*, 8: 390–394 (1964).

"Lipid decomposition by immogilized lipase," *Chem. Abstr.*, vol. 100, 1984, 100:205610m, JP 59 28,483.

Chi, Nakamura and Yano, "Enzymatic Interesterification in Supercritical Carbon Dioxide," *Agric. Biol. Chem.*, 52:6, pp. 1541–1550 (1988).

Funazukuri, Hachisu andakao, "Measurment of Diffusion Coefficients of C18 Unsaturated Fatty Acid Methyl Esters, Napthalene and Benzene in Supercritical Carbon Dioxide by a Tracer Response Technique," *Anal. Chem.*, 61:118–122 (1989).

Ralston, *Fatty Acids and Their Derivatives*, John Wiley & Sons, Inc., New York; Chapman & Hall, Ltd., London, pp. 274–321.

"Commercial Fatty Acids and Their Derivatives", pp. 378–385.

Drew and Hixson, "The Solubility Relationship of High Molecular Weight Fatty Acids and Their Esters in Propane Near the Critical Temperature," *American Institute of Chemical Engineers*, pp. 675–694 (Presented at the St. Louis, Mo. meeting, Nov. 9–21, 1944).

Gembicki, Johnson and Ekwall, UOP Inc., Des Plaines, IL., "Sorbex Separations A Key to New Product Opportunities".

Swientek, "Supercritical fluid extraction separates components in foods," *Food Processing*, pp. 32–36 (Jul. 1987).

Nakamura, Chi, Yamada and Yano, "Lipase Activity and Stability in Supercritical Carbon Dioxide," *Chem. Eng. Commun.*, 45: pp. 207–212 (1986).

Morita, Narita, Matoba and Kito, "Synthesis of Triacylglycerol by Lipase in Phosphatidylcholine Reverse Micellar System," 61 *JAOCS* 10, pp. 1571–1574 (1984).

Inada, Nishimura, Takahashi, Yoshimoto, Saha and Saito, "Ester Synthesis Catalyzed by Polyethylene Glycol-Modified Lipase in Benzene," 122 *Biochemical and Biophysical Research Communications* 2, pp. 845–850 (1984).

Ikushima, Hatakeda, Ito Saito, Assano and Gotto, "A Supercritical Carbon Dioxide Extraction from Mixtures of Triglycerides and Higher Fatty Acid Methyl Esters Using a Gas-Effusion-Type System," 27 Ind. Eng. Chem. Res., pp. 818–823 (1988).

Miller, Teale & Davis (Dept of Med., The General Infirmary, Leeds LS1 3EX, U.K.) "Mixed Lipolytic Activities of an Enzyme Preparation from Pancreas," Proceedings of the Biochemical Society, pp. 38–39.

Soda, "Bioconversion of liphphilic compounds by immobilized biocatalysts in organic solvents," *TIBS*, p. 428 (Dec. 1983).

Zschau, "The Use of Bleaching Earth in Fatty Acid Production," 61 *JAOCS* 2, (Feb., 1984).

Bonanome and Grundy, "Effect of Dietary Stearic Acid on Plasma Cholesterol and Lipoprotein Levels," 318 *The New England Journal of Medicine*, 19, pp. 1244–1271 (1988).

Dagnai, "Enzyme Active in Hot Organic Media," *C&EN* (Jul. 2, 1984), p. 23.

LeRiche and Stubbs, "New Drying Oils Produced by Solvent Segregation," *Transactions and Communications*, pp. 3–25 (Jan. 1954).

"Enzymatic Esterification: An Effective Alternative to Chemical Synthesis," 3 *Biotechnology News* 7, p. 5 (1984).

Bailey, *Melting and Solidification of Fats*, pp. 4–5 (1950).

Goss, "Solvent Refining and Fractionation of Fats and Oils," *The Journal of The American Chemists' Society*, pp. 584–588 (Oct. 1949).

Ichihara and Noda, "Some Properties of Diacylglycerol Acyltransferase in a Particulate Fraction from Maturing Safflower Seeds," 21 *Phylochemistry* 8, pp. 1895–1901 (1982).

Kinsella, "Food Components with Potential Therapeutic Benefits: The n–3 Polyunsaturated Fatty Acids of Fish Oils," *Food Technology*, pp. 89–97 and 146 (Feb. 1986).

(List continued on next page.)

OTHER PUBLICATIONS

Randall, "The Present Status of Dense (Supercritical) Gas Extraction and Dense Gas Chromatography: Impetus for DGC/MS Development," 17, *Separation Science and Technology*, 1, pp. 1–118 (1982).

Kaimal and Suroja, "Selective Removal of Linolenic Acid from Soybean Oil by Lipase-catalyzed Interesterification at Low Temperatures," 10, *Biotechnology 5*, pp. 337–340 (1988).

Seitz, "Industrial Application of Microbial Lipases: A Review," 51, *Journal of The American Oil Chemists' Society*, pp. 12–16 (Feb. 1974).

Sohns, Beal and Griffin, Jr., "Cost of Producing Linoleic Acid from Safflower Oil," 40, *The Journal of American Oil Chemists' Society*, pp. 169–172 (May 1963).

Tombs and Blake, "Stability and Inhibition of *Asperillus* and *Rhizopus* Lipases," 700, *Biochimica et Biophysica Acta*, pp. 81–89 (1982).

Eisenbach, "Supercritical Fluid Extraction: A Film Demonstration," 88, *Phys. Chem.*, pp. 882–887 (1984).

Best, "Ingredient Trends: Specialty Oils Update," *Prepared Foods*, pp. 153–158 (Jan. 1987).

Asahi Denka Kogyo K.K., "Transesterification of fats by lipase," 16–*Fermentations*, vol. 99, 1983, 99:156866s, JP 58,116,688, p. 493.

Asahi Denka Kogyo K.K., "Transesterification of fats by lipase," 16–*Fermentations*, vol. 99, 1983, 99:156864q, JP 58,16,689, p. 493.

R. B. Aisina et al., "Microencapsulated Lipase," 63–*Pharmaceuticals*, vol. 101 1984, 101:216451z, USSR SU 1,112,056.

"Biotechnologically Redesigned Fats have Substantial Economic Possibilities," *Food Processing* (Apr., 1985) pp. 50–51.

Stahl, Schutz and Mangold, "Extraction of Seed Oils with Liquid and Supercritical Carbon Dioxide," *American Chemical Society*, pp. 1153–1157 (1980).

*Chemical Abstracts*, vol. 106, 1987, 106:83307m, JP 61,257,192.

"Transesterification of oils and fats with lipase," *Chem. Abstr.*, vol. 97, 1982, 97:214581s, JP 57,78496.

Kyono, Uchibori, Tsujita, Nakao, Morita and Nishitani, "Polyglycerol fatty acid esters by enzymic esterification," *Chemical Abstracts*, vol. 106, 1987, 106:31407z, JP 61 187,795.

Rosenberg and Schaefer, "Dietary Saturated Fatty Acids and Blood Cholesterol," *The New England Journal of Medicine*, 318:19, p. 1270 (May 1988).

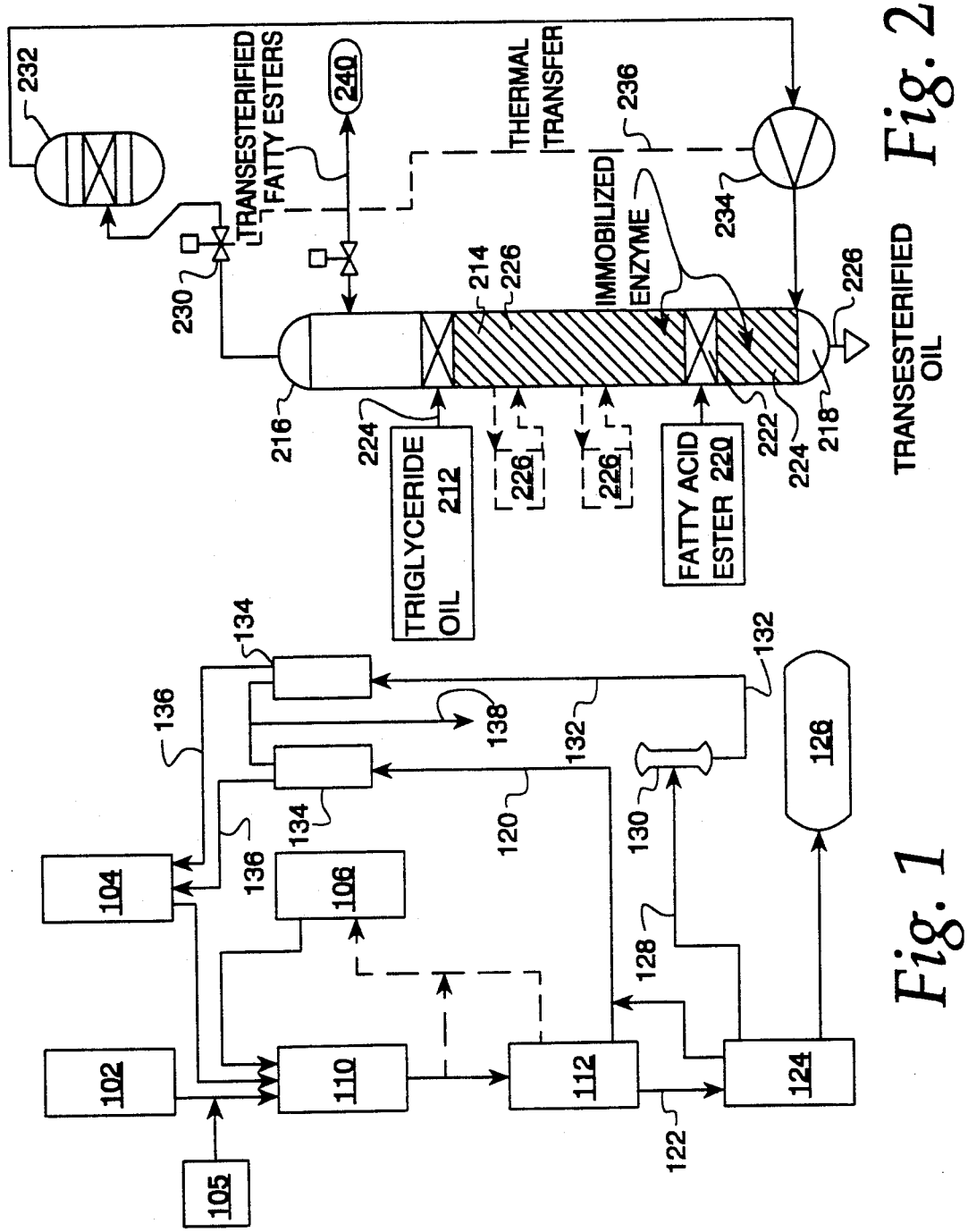

MULTISTAGE COUNTERCURRENT CASCADE SYSTEM

ENZYMATIC METHOD FOR PREPARING TRANSESTERIFIED OILS

This application is a continuation-in-part, of Ser. No. 714,432 filed Jun. 13, 1991, now abandoned which is a continuation-in-part of Ser. No. 455,551, filed Dec. 18, 1989, now abandoned and Ser. No. 700,115, filed May 9, 1991, now abandoned which is a continuation of Ser. No. 455,555, filed Dec. 18, 1989, now abandoned which are incorporated herein by reference.

BACKGROUND OF THE INVENTION

The present invention is directed to enzymatic methods for preparing glycerides and to designed glycerides of specific composition.

The present invention is, in part, directed to margarine oils, and more particularly is directed to margarine oils having both low trans- acid content and low content of intermediate chain saturated fatty acids, together with margarine-type thermal melting characteristics and/or smooth organoleptic consistency. The invention is also directed to oils having a very low level of saturated fatty acid components, and to enzymatic transesterification methods for producing low-saturate, edible oil products. This invention may also be used to introduce specific health-promoting fatty acids, e.g., omega-3 fatty acids such as eicosapentanoic acid, into triglyceride oils and fats. This invention may also be used to introduce medium chain fatty acids, e.g., having six to twelve carbon atoms per molecule, into triglycerides. Said fatty acids can be derived from natural or synthetic sources and include both odd and even carbon numbers. This invention can also be used to incorporate difunctional fatty acids, such as succinic, adipic, octanedioic acid, etc. so as to create glyceride oligomers which may have desirable properties as cooking oils, etc. This invention may also be used to introduce incompletely metabolized, low calorie fatty acids, e.g., furan fatty acids, derived from natural or synthetic sources into triglyceride oils and fats. In addition, the invention is directed to counter-current methods for enzymatic esterification, interesterification, transesterification and refining.

Margarine oils are predominantly mixtures of triglycerides which have a plastic consistency at refrigeration and/or ambient temperature, but which have the essential characteristic of melting readily and with substantial completeness in the mouth of the consumer. Such a melting characteristic requires a solid fat index which has an extended gradient over a broad temperature range. In addition, margarine oils must have a crystal size and shape which provides a smooth organoleptic consistency without graininess or similar mouthfeel defects in homogeneity. Margarine oils are distinguished from plastic shortenings, which typically have a high stearic acid content and a melting point higher than body temperature, which is characterized by the presence of substantial solid fat content at body temperature. The high solid fat content at body temperature is desirable in plastic shortenings for use in various hot dishes, or in dispersed form in products such as pastries and baked goods where the high solid fat content is not deleterious. However, a residue of solid fat such as that present in conventional plastic shortenings which fails to melt at body temperature, imparts to a margarine oil an unacceptable waxy sensation in the mouth. As used herein, the term "margarine oil" and "margarine fat" are used interchangeably.

Coconut oil and the other oils of the lauric acid type have a relatively low melting profile as a result of their relatively high concentration of intermediate chain saturated fatty acids and may conventionally be utilized as a component of margarine oils. By "intermediate chain saturated fatty acid" is meant an edible saturated fatty acid having from 8 to 16 carbon atoms, particularly including palmitic, myristic and lauric acids or mixtures thereof. Because the melting points of saturated fatty acids exhibit a progressive increase as the carbon chain is lengthened, fats of the coconut oil type which contain relatively large proportions of $C_8$ to $C_{16}$ saturated fatty acid moieties, have lower melting points than fats with an equivalent degree of unsaturation that comprise a high proportion of $C_{18}$ fatty acid glycerides. However, diets high in intermediate chain saturated fatty acids, notably lauric, myristic and palmitic acids common to lauric acid oils, have been reported in the medical literature as being a factor in the production of plasma cholesterol in populations at risk for coronary heart disease. However, stearic acid although it is a saturated fatty acid, has been reported to have minimal or even reducing effect on cholesterol level ["Effect of Dietary Stearic Acid on Plasma Cholesterol and Lipoprotein Levels", Bonanome, et al., New England Journal of Medicine, Vol. 318, 1244–1271 (1988)]. Accordingly, although lauric acid oils have desirable margarine oil properties, margarine oils which have low intermediate chain fatty acid content would be desirable.

Vegetable oils, such as cottonseed, peanut, sesame, corn and sunflower oils, and other liquid oleic-linoleic acid oils, as well as soybean oil, may be partially hydrogenated for the production of margarine oils of the requisite melt and consistency characteristics of broad thermal melting range, substantially complete melting at body temperature, and smooth organoleptic characteristics. The desired consistency is typically obtained by blending two or more partially hydrogenated vegetable oils, or blending liquid (unhydrogenated) vegetable oil with a partially hydrogenated vegetable oil. However, conventional partial hydrogenation of vegetable oils containing unsaturated acids, depending on catalyst selectivity, degree of hydrogenation and other processing variables, may produce substantial amounts of unsaturated fatty acids of trans-, rather than cis- configuration. margarine oils which contain minimal amounts of such trans- acid moieties, together with the requisite solid fat index thermal profile, smooth organoleptic consistency and low intermediate chain fatty acid content, would be desirable.

The main components of margarine oils are triacylglycerols (triglycerides) which are triesters of glycerol and various saturated and unsaturated fatty acids. The physical properties of fats and oils are, to a large extent, determined by the characteristics of the individual fatty acid moieties and by their distribution within the triglyceride molecule. Interesterification is a technique which may be used to alter the fatty acid composition and distribution and therefore the physical properties of triglyceride mixtures. In such processes, chemical catalysis by sodium metal or a sodium alkoxide is used to promote the migration of fatty acyl groups between and within glycerol molecules, so that the product consists of acylglycerol mixtures in which the fatty acyl groups are randomly distributed among the glyceride molecules. The use of enzymes such as site specific lipases permits formation of novel, functional fats which cannot be obtained by conventional chemical processes.

Edible oils and fats typically primarily comprise various fatty acid triesters of glycerol with the structure of the fatty acid moieties and their distribution on the glycerol backbone determining the physical characteristics of the oil or fat. The specific types of fatty acids also play an important role in diet and health. Fats and oils in general are a rich source of energy in the diet and are important in the synthesis of membranes and other essential cell components. Moreover, dietary fatty acid content may potentially be controlled to affect physiological characteristics such as serum cholesterol levels. For example, studies of normcholesterolemic men has shown that a dietary decrease in saturated fatty acids may have more of an effect in lowering serum cholesterol [Keys, "Prediction of Serum Cholesterol Response to Change in Fats in the Diet", Lancet, 2:959–962] than an increase in polyunsaturated fatty acids.

Natural vegetable oil triglycerides typically contain substantial amounts of esterified saturated fatty acids. For example, soybean oil may typically contain about 14–16 weight percent of esterified saturated fatty acids, and natural canola oil may contain about 5–8 weight percent of esterified saturated fatty acids. Intermediate carbon chain length (i.e., $C_{12}$–$C_{16}$) dietary saturated fatty acids, notably lauric, myristic and palmitic acids, have been reported in the medical literature as being a more significant factor in the increase of plasma cholesterol than stearic acid, which has been reported to have minimal or even reducing effects on cholesterol levels ["Effect of Dietary Stearic Acid on Plasma Cholesterol and Lipoprotein Levels", Bonanome, et al., New England Journal of Medicine, Vol. 318, 1244–1271 (1988)]. Soybean oil and canola oil typically contain, respectively, over 10 percent and over 3 percent by weight of esterified intermediate chain length saturated fatty acids, primarily palmitic acid. Accordingly, it would be desirable to economically produce or manufacture triglyceride oils having very low levels of saturated fatty acids, and particularly low levels of lauric, myristic and palmitic acids. Most food products prepared from vegetable oils having less than about 3.5 weight percent of esterified saturated fatty acids may be regarded as substantially free of such fatty acids for regulatory purposes.

Potentially, the modification of vegetable oils to produce low-saturate oil products could be carried out by dehydrogenation, chemical transesterification, enzymatic transesterification or genetic selection and modification. However, dehydrogenation processes are not available for selectively dehydrogenating esterified saturated fatty acids of vegetable oils. The use of somaclonal variation as a means of selection for genetic variation in plant parts which may produce triglycerides with specific desirable fatty acids may be used, but problems may arise in the stabilization of the desired trait in future generations. Recombinant DNA techniques might be used to increase the production of an oil of predetermined composition, but this is a very complex task in difficult or presently unknown areas of plant lipid biosynthesis. [Stumpf, "Biosynthesis and Function of Plant Lipids", Am. Soc. Plant Physiol., pp. 1–15, 1983]. For example, fatty acid synthesis has many potential rate limiting enzymes as well as proteins, such as acetyl-CoA carboxylase, ACP-acetyl transferase, 3-oxoacyl ACP synthase, ACP malonyl transferase and acyl carrier protein. Modifications of specific triglyceride synthesis entail changes in fatty acid composition dependent on acyl ACP thioesterase and various desaturase complexes, as well as acyltransferase enzymes which attach the fatty acid moieties to glycerol. Thus, to isolate the rate limiting enzymes/proteins and their corresponding genes to create transgenic plants which specifically express them in tissues for storage purposes poses substantial technical problems.

Chemical and enzymatic transesterification are well known for modifying the fatty acid composition or distribution of triglyceride oils. Chemical transesterification is based on the use of a chemical catalyst such as sodium methoxide or a sodium metal to promote the migration of the fatty acid moieties between glyceride molecules, to produce a random distribution of the fatty acid moieties.

Enzymatic transesterification of triglycerides may also be used to modify the characteristics and/or composition of triglycerides. Such processes may be used for selective interchange under relatively mild reaction conditions. For example, vegetable oils may be transesterified with a fatty acid or lower alkyl monoester to produce a variety of end products as described in U.S. Pat. Nos. 4,268,527; 4,426,991; 4,275,011; 4,472,503 and U.K. Application 2,199,397.

Extracellular microbial lipases are generally of three types, depending upon their specificity. One group of lipases is generally nonspecific, both as regards the position on the glycerol molecule which is hydrolyzed or esterified, and the nature of the fatty acid released or esterified. Depending on the reaction conditions, such lipases catalyze the nonselective hydrolysis, alcoholysis and/or esterification (including transesterification) of fatty acid triglycerides. The lipases produced by *Candida cylindracae*, also known as *C. rugosa* (Benzonana, G. and S. Esposito, Biochim. Biophy. Acta. 231:15 (1971)), *Corynebacterium acnes*, (Massing, G. S., Ibid. 242:381 (1971)), and *Staphylococcus aureus*, (Vadehra, D. V., Lipids 9:158 (1974)), *Candida lipolytica* and *Pseudomonas fluorescens* are examples of such nonspecific lipases.

A second group of lipases preferentially acts on the primary, 1- and 3-positions of the glycerol or triglyceride molecule. When a 1-, 3-positionally specific lipase is used to catalyze the transesterification of a mixture of triglycerides or a mixture of triglyceride plus free fatty acid or monoester, the action of the enzyme is substantially confined to the 1- and 3-positions of the glycerol. The lipases of *Rhizopus delemar* and *Mucor miehei* such as described in U.S. Pat. No. 4,798,793, are examples of 1-,3- specific lipases, as are the lipases of *Aspergillus niger, Rhizopus arrhizus, Rhizopus niveus, Muror javanicus, Rhizopus javenicus, Rhizopus oxyzae.*

A third group of lipases has substantial selectivity for certain long chain unsaturated fatty acids having a cis-double bond at the 9-position from the carboxylate group of the fatty acid. Long chain saturated fatty acids, and unsaturated fatty acid esters without a double bond in the 9-position, are only slowly hydrolyzed in the presence of such lipases. Thus the esters of oleic, palmitoleic, linoleic and linolenic acids, all of which have a cis double bond in the 9-position, are preferentially hydrolyzed, esterified or transesterified. The presence of an additional double bond between the carboxyl group and the double bond in the 9-position makes fatty acid esters resistant to the action of this lipase. Triglycerides containing medium chain saturated $C_{10}$ and $C_8$ fatty acids may exhibit some, albeit reduced, reactivity with such enzymes. Examples of such delta-9 specific lipases which preferentially act on long-chain fatty acids containing a cis- double bond in the 9-position are the lipase produced by the mold *Geotrichum candidum* [Macrae, A. R., in *Microbial Enzymes and Biotechnology*, edited by W. M. Fogarty, Applied Science Publishers, London, 1983, p. 225, Jensen, R. G., *Lipids* 9:149 (1974), Jensen, R. G., and R. E. Pitas, in *Lipids*, edited by R. Paolette, G. Porcellati and G. Jacini, Raven Press, New York, 1976, Vol. 1, p. 141], and the lipase produced by *Penicilliun cyclopium* [Glyceride Synthesis by Four Kinds of Microbial Lipase, Tsujisaka, et al.; *Biochim. Biophy. Acta.* 489; 415–422 (1977)]. Such lipases will activate transesterification of unsaturated delta-9 fatty acid groups of glyceride oils, but do not affect the saturated acid components of the oils.

Enzymatic methods which may be used to reduce the saturated fatty acid content of vegetable oils to levels below about 3.5 weight percent, and total levels of intermediate chain length fatty acids below about 2 weight percent, would be desirable, and it is an object of the present invention to provide such low-saturate vegetable oils. It is a further object to provide such methods which may be used to provide low-saturate oils having specific unsaturated fatty acid distribution, as well as low saturate edible oils having specific, nutritionally desirable properties of oleic, linoleic and linolenic acids. These and other objects will become apparent from the following detailed description and the accompanying drawings.

Egg yolks provide excellent functional emulsification properties for food products such as mayonnaise, and are a necessary or desirable component for many food products such as spoonable and pourable food dressings. The functional emulsification properties of egg yolks are believed to be largely attributable to phosphatide, protein and phosphatide/protein complex components of the egg yolk. However, in addition to these components which provide functional emulsifying properties, egg yolks also contain a substantial amount of cholesterol.

Methods are desirable for removing cholesterol from egg yolks without solvent denaturation or heat-denaturation of the egg yolk protein, and without causing substantial loss of phosphatides or phosphatide/protein complexes which provide the desirable functional characteristics of egg yolks. Methods which also could optionally be carried out to minimize the loss of natural egg yolk triglycerides would also be desirable. It would also be desirable if such methods could be provided which could be utilized to separate cholesterol from dry or liquid whole egg products without denaturation of egg protein.

A wide variety of methods have been used for removal of cholesterol from egg yolks, including hexane and aqueous alcohol-hexane extraction, liquified methyl ether extraction, and supercritical carbon dioxide extraction, but each of these methods has characteristic limitations or disadvantages. Extraction of egg yolk cholesterol into vegetable oil is effective for providing substantially cholesterol-free or cholesterol reduced egg yolks, but this produces a stream of cholesterol-containing vegetable oil. Such vegetable oil could be reused or used as a more desirable transesterification source material if the cholesterol could be readily removed.

Accordingly, it is an object to provide novel methods for separation of cholesterol from egg yolks and whole eggs. It is a further object to provide methods for producing low-cholesterol or cholesterol free food products such as mayonnaise, spoonable dressings and pourable dressing. These and other objects will be apparent from the following detailed description and the accompanying drawings.

DESCRIPTION OF THE DRAWINGS

FIG. 1 is a process flow diagram for an embodiment of a single step batch or cocurrent continuous reaction method for producing a margarine oil in accordance with the present invention having a minimal content of unsaturated fatty acids of trans- configuration and intermediate chain saturated fatty acid;

FIG. 2 is a process flow diagram for a continuous counter-current reaction method for producing a margarine oil having a minimal content of unsaturated fatty acids of trans- configuration and intermediate chain fatty acids;

DESCRIPTION OF THE INVENTION

Figure 3:
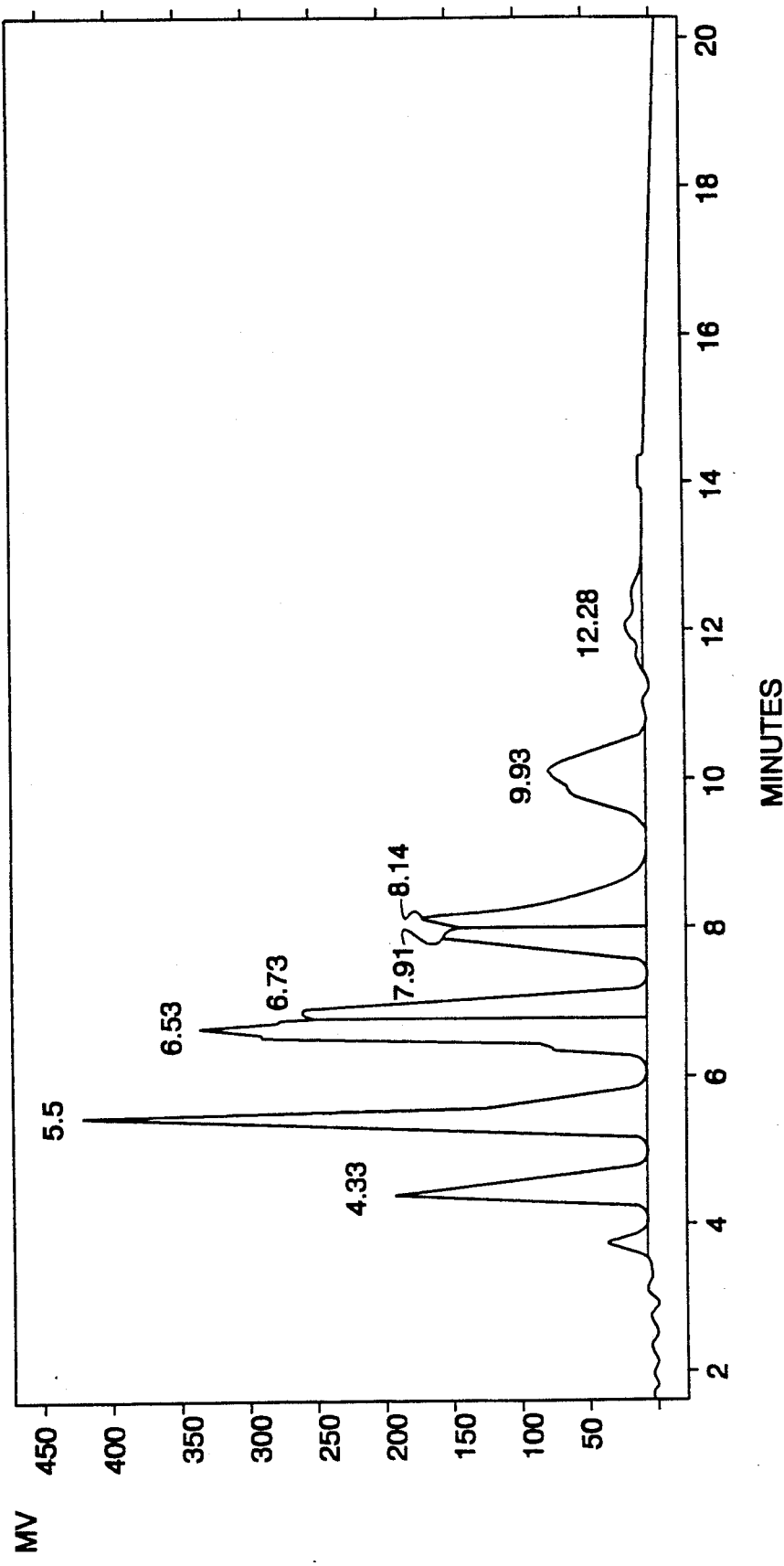
FIG. 3 is a high pressure liquid chromatographic elution chart representing the triglyceride composition of initial soybean oil used in preparing a margarine oil in accordance with the present invention.

Various aspects of the present invention are directed to margarine oils having both low trans- acid and intermediate chain fatty acid content, together with a broad margarine type solids fat index melting profile and a smooth organoleptic consistency. The present invention is also directed to methods for producing such margarine oils.

As indicated, the margarine oils are provided in accordance with the present invention have a low trans-acid content. By "trans- acid" is meant an unsaturated fatty acid having a carbon chain length of from 16 to 24 carbon atoms and having at least one unsaturated carbon-carbon bond which is in trans- configuration. In conventional margarine oil products prepared from partially hydrogenated vegetable oil, the trans- acid content may exceed 25 weight percent or more of the margarine oil composition, as a result of the partial hydrogenation conditions appropriate to providing a solid fat index of the margarine oil type. In this regard, the margarine oils in accordance with the present invention, comprise less than 6 and preferably less than 3 weight percent of esterified trans- unsaturated fatty acid moieties, based on the total weight of the margarine oil. Such oils may be provided which have less than 2, and even less than 1 weight percent of trans- unsaturated fatty acid moieties, based on the total weight of the margarine oil. As used herein, the weight percentage of trans- unsaturated fatty acids is determined in accordance with AOCS official test Cd 14-61 (1984). Also, as used herein, the weight percent of saturated or unsaturated fatty acid moieties in a margarine oil or vegetable oil glyceride composition is calculated based on the total weight of the fatty acids contained in the margarine oil. As used herein, when referring to weight percent of one or more fatty acid moieties of a margarine oil, the weight percent is calculated based on all of the fatty acid moieties of the margarine oil being hydrolyzed to free fatty acid. The weight percent of one or more species of fatty acid moiety is then calculated as the weight percent of such one or more species based on the total weight of free fatty acids. AOCS official method Ce 1-62 (81) may be used to determine the weight percent of respective fatty acid moieties of a margarine oil.

As also indicated, the margarine oil product has a minimal amount of intermediate chain saturated fatty acid moieties. In this regard, the margarine oil product comprises less than about 12 weight percent and preferably less than about 6 weight percent and most preferably less than about 3 weight percent of intermediate chain saturated fatty acids based on the total weight of the product. Specifically, the total content of palmitic, myristic, or lauric acids, or mixtures thereof, in free or esterified form, is less than 6 percent of the total weight of the fatty acid content of the margarine oil product and preferably less than half this amount, or less than 3 weight percent.

Further in accordance with the present invention, margarine oils are provided which have a broad profile of triglycerides of unsaturated $C_{18}$ fatty acids in esterified form which produce a wide variety of glyceride components of the oil. In this regard, the margarine oil has an esterified linoleic acid moiety content of from about 25 to about 45 weight percent and preferably from about 30 to about 40 weight percent and from about 0 to about 11 weight percent of esterified linolenic acid moieties and preferably from about 3 to about 5% linolenic acid moiety. Linolenic acid may generally be provided as a component of the soy oil or other linolenic acid containing oils used as a starting material. Further in accordance with the present invention, the margarine oil has an oleic acid content of from about 5 to about 25 weight percent and preferably from about 10 to about 20 weight percent. Moreover, the margarine oil comprises from about 84 to about 95 weight percent of triglycerides, and preferably from about 88 to about 92 weight percent triglycerides. The margarine oil of the invention has relatively high diglyceride content, which is believed to contribute to the smooth organoleptic properties and the solid fat melting index profile characteristics of the product. In this regard, the diglyceride content of the oil will generally be in the range of from about 5 to about 16 weight percent and preferably from about 8 to about 12 weight percent. The monoglyceride component is generally less than about 1 weight percent and preferably is less than about 0.5 weight percent, based on the total weight of the margarine oil product. The weight percent of monoglycerides and diglycerides is determined based on the actual weight of the mono and/or diglyceride component, as a percentage of the total weight of mono-, di- and triglycerides of the margarine oil composition.

It is an important aspect of the present invention that the fatty acid distribution of the margarine oil of the present invention is non-random, and is distributed differently among the 1-, 3-positions of the glycerine component and the 2-position of the glycerine component. In this regard, the esterified stearic acid is predominantly distributed in the 1-, 3-positions, while esterified unsaturated fatty acid moieties are in higher concentration at the central 2-position of the glyceride molecules. This non-random selective distribution prevents high concentrations of tristearin from forming in the margarine oil. This places the stearic acid moieties at the exterior of the molecule, and concentrates the unsaturated fatty acid component at the internally shielded and more sterically hindered central 2-position. In addition, the hydroxyl groups are non-randomly distributed in favor of the same 1- and 3-positions at which the high melting stearic acid moieties are concentrated, reducing potential distearate concentration. The weight percentage of the principal fatty acid components of the margarine oils of the present invention, at each of the respective 1-, 3- and 2-positions, is as follows:

|  | 1-, 3- Glyceride positions weight percent | 2- Glyceride position weight percent |
|---|---|---|
| Palmitic acid (P) | 5–10 | 0–2.0 |
| Stearic acid (S) | 50–70 | 0–5.0 |
| Oleic acid (O) | 5–15 | 20–30 |
| Linoleic acid (L) | 10–30 | 60–80 |
| Linolenic acid (Ln) | 0–10 | 3–12 |

As indicated, an important aspect of the present invention is the provision of a broad melting range and smooth organoleptic characteristics. The margarine oil should have a solid fat index which decreases from a value in the range of from about 7 to about 31 percent at 10° C., a typical refrigeration temperature, to a value of less than three percent at 38.7° C., a value slightly higher than body temperature. Margarine oils in accordance with the present invention are characterized by margarines with solid fat index profiles as follows:

| Temperature | Dilatometric Solid Fat Index, Percent |
| --- | --- |
| 10° C. | 7–31 |
| 21.1° C. | 3–25 |
| 26.7° C. | 0.75–10 |
| 33.3° C. | 0.5–4 |
| 38.7° C. | less than 3 |

The specified solid fat indexes at the specified temperatures are measured by dilatometric methodology in accordance with AOCS procedure Cd 10-57. The dilatometric procedure measures volume changes in the margarine oil as a function of temperature, which changes are a function of the relative proportion of solid and liquid fats. The solid fat index is a dilatometric index on a percentage scale of 0 (for no solid fat) to 100 (for all solid fat).

Different types of particularly desirable margarine oil having, respectively, a firm bodied (or "stick") consistency and a soft bodied (or "tub") consistency at refrigeration temperature, may be provided in accordance with the present invention. A particularly preferred margarine oil is a firm bodied margarine oil having a solids fat index from about 23 to about 31 at 10° C. (50° F.), and preferably from about 26 to about 27.6 at 10° C. and most preferably from about 26 to about 27.6 at 10° C. At 21.1° C. (70° F.), the firm bodied margarine oil composition has a solid fat index from about 15 to about 25 and preferably from about 21 to about 22.6. At 26.7° C. (80° F.), the firm bodied margarine oil composition has a solid fat index from about 6 to about 10, and preferably from about 8 to about 9 and more preferably from about 8 to about 9 at 26.7° C. At 33.3° C. (92° F.), the firm bodied margarine oil composition has a solid fat index from about 0.5 to about 4 and preferably from about 1.9 to about 2.9, and at 38.7°. (100° F.), the firm bodied margarine oil composition has a solid fat index from about 0 to about 3 and preferably less than 2.

A soft-bodied or "tub" margarine oil product may also be provided in accordance with the present invention. A soft-bodied margarine oil in accordance with the present invention will a solid fat index from about 7 to about 12 and preferably from about 9.5 to about 10.5 at 10° C. At 21.1° C. (70° F.), the soft-bodied margarine oil composition has a solid fat index from about 3 to about 10 and preferably from about 5 to about 8. At 26.7° C. (80° F.), the soft-bodied margarine oil composition has a solid fat index of from about 0.75 to about 8, and typically from about 1 to about 7, preferably about 2 to about 4. At 33.3° C. (92° F.), the soft-bodied margarine oil composition has a solid fat index from about 0.5 to about 3 and preferably from about 0.7 to about 1.2. At 38.7° C. (100° F.), the margarine oil composition has a melting dilation range from about 0 to about 1.5 and preferably less than about 0.8.

The low trans- acid and low intermediate chain saturated acid margarine oils of the present invention may be provided using immobilized enzyme systems and an inexpensive oil source such as soybean oil in a precise sequence of transesterification, separation, full hydrogenation of fatty acids liberated during transesterification and recycle steps. By "transesterification" is meant an exchange of fatty acid moiety or acyl radical at a glyceride oxygen or hydroxyl radical, which includes interesterification and intraesterification.

Generally in accordance with the present invention, the margarine oil may be provided by enzymatic transesterification of an edible liquid vegetable oil comprising at least about 73 and preferably 80 weight percent of eighteen carbon fatty acid moieties ($C_{18}$ saturated and unsaturated fatty acids), and more preferably at least about 85 weight percent of $C_{18}$ fatty acid moieties based on the total weight of the edible liquid vegetable oil such as soybean oil. Such $C_{18}$ fatty acid moieties include stearic acid, oleic acid, linoleic acid and linolenic acid. In addition, the edible liquid vegetable oil should comprise less than 5 and preferably less than 1 weight percent of esterified palmitic acid in the 2- glyceride position, and less than 2.5 and preferably less than 0.5 weight percent of esterified stearic acid in the 2- glyceride position.

The liquid vegetable oil may desirably further comprise at least about 15, and more preferably at least about 22 weight percent of esterified oleic acid in the liquid vegetable oil. In addition, the liquid vegetable oil will preferably comprise at least about 20 weight percent of esterified linoleic acid, and at least about 0.25 and preferably at least 5 percent of esterified linolenic acid. Moreover, the liquid oil should contain less than 2 weight percent, and preferably less than 1 weight percent of esterified stearic acid in the 2-position. As will be discussed, the limited content of stearic acid in the 2-position limits the possible formation of high melting tristearin. Sunflower, soybean, safflower, corn, soy and canola (low erucic acid rapeseed) oils or blends thereof may also be used as starting material for the manufacture of margarine oils in accordance with the present invention. Soybean oil is a particularly preferred starting material. High oleic acid oils, such as high oleic (e.g., having greater than 80% oleic acids), sunflower, safflower, olive oil do not by themselves provide margarine oils in accordance with the present invention because the solids fat index distribution does not produce the finished oil characteristics. The low linoleic acid content of such oils produces a sharper melting point which is undesirable. These oils must therefore be interesterified in combination with linoleic oils, such as standard sunflower, safflower, corn, cottonseed or mixtures thereof.

The transesterification reaction is carried out by directed enzymatic transesterification of the liquid vegetable oil starting material with a relatively high proportion of stearic acid, using a 1-, 3-positionally specific extracellular lipase enzyme. Extracellular microbial lipases are generally of three types, depending upon their specificity. Some lipases are generally nonspecific, both as regards the position on the glycerol molecule which is hydrolyzed or esterified, and the nature of the fatty acid released or esterified. Depending on the reaction conditions, such lipases catalyze the nonselective hydrolysis, alcoholysis and/or esterification (including transesterification) of fatty acid triglycerides. The lipases produced by *Candida cylindracae*, also known as *C. rugosa* (Benzonana, G. and S. Esposito, *Biochim. Biophy. Acta.* 231:15 (1971)), *Corynebacterium acnes*, (Massing, G. S., *Ibid.* 242:381 (1971)), and *Staphylococcus aureus*, (Vadehra, D. V., *Lipids* 9:158 (1974)), are examples of such nonspecific lipases. Such lipases are not utilized in the present methods, because they do not provide the non-random distribution required by the margarine oils of the present invention.

The 1-, 3-positionally specific lipases utilized in the present invention constitute a second type of lipases which act on the outer, 1- and 3-positions of the glycerol or triglyceride molecule. When a 1-, 3- positionally specific lipase is used to catalyze the interesterification of a mixture of triglycerides or a mixture of triglyceride plus free fatty acid or monoester, the action of the enzyme is substantially confined to the 1- and 3-positions of the glycerol. The lipases of *Rhizopus delemar* and *Mucor miehei* are examples of 1-, 3-positionally specific lipases, as are the lipases of *Aspergillus niger, Rhizopus arrhizus, Rhizopus niveus, Muror javanicus, Rhizopus japenicus, Rhizopus oxyzae*.

A particularly preferred enzyme is an immobilized *Mucor miehei* lipase (NOVO Lipozyme IM 20) such as described in European Patent Application 0140542, which is incorporated by reference herein. A third group of lipases has substantial selectivity for certain long chain unsaturated fatty acids having a cis- double bond at the 9-position of the fatty acid (from the carboxylate group), and are also not used in the present methods.

The manufacturing processes for preparing the low trans- fatty acid, low intermediate chain saturated fatty acid margarine oils may be carried out in batch mode, or in continuous flow cocurrent or counter-current mode. A continuous process can use a reactor containing enzyme catalyst, said reactor being a packed bed, fluidized bed or ebullating bed where the enzyme catalyst remains in the bed and reactants continuously flow through the bed. Batch and continuous processes may be carried out in a single transesterification step or multiple steps. The use of multiple steps permits use of lower stearic acid/liquid vegetable oil ratios in each step, but requires multiple separation steps. Single step batch or cocurrent continuous processes require relatively high ratios of stearic acid to liquid vegetable oil in the initial reaction mixture, but are generally more economical than multi-step processes.

In accordance with such manufacturing methods, the high $C_{18}$ liquid vegetable oil is combined with a stearic acid source material comprising at least about 84 weight percent of stearic acid, based on the total weight of fatty acids in the stearic acid source. The stearic acid source material is preferably stearic acid which is at least 84 percent by weight stearic acid, and less than 6 weight percent palmitic acid. However, stearic acid esters of low molecular weight monohydric alcohols such as methyl stearate and ethyl stearate may also be utilized. The stearic acid source material may include minor amounts (e.g., 0–10 weight percent) of unsaturated $C_{18}$ fatty acids or esters, and/or saturated or unsaturated $C_{20}$–$C_{22}$ fatty acids or esters. For cocurrent or batch reactions, the stearic acid component is combined with the vegetable oil in one or more reaction stages to provide a transesterification mixture which may vary in composition depending upon the end product desired, the number of transesterification stages to be utilized, and the degree of equilibrium to be achieved in the transesterification mixture. In general, for both reactions, the weight ratio of stearic acid to triglyceride in the initial transesterification mixture should be at least about 1:3, and preferably at least about 1:1. For single step transesterification mixtures, the weight ratio of stearic acid to triglyceride in the initial transesterification mixture should be at least about 1:2, and preferably in the range of from about 1:1 to about 3:2. A weight ratio of 1.15 parts stearic acid to 1 part soybean oil in a solvent such as hexane is particularly preferred in a single step process. The stearic acid and the triglyceride are desirably dissolved in hexane or other suitable solvent in a weight ratio in the range of from about 0.5 to about 2.0, solvent to combined stearic acid plus triglyceride vegetable oil such as soybean oil.

The transesterification mixture is contacted with the immobilized enzyme under time and temperature conditions for substantially equilibrating the ester groups in the 1-, 3-positions of the glyceride component, with the nonglyceride fatty acid components of the reaction mixture. The reaction time may range from about 0.5 hour to about 100 hours, depending on the concentration and activity of the lipase, and the temperature of the reaction mixture. For a continuous reaction, the system can be represented by weight hourly space velocity (WHSV) which is pounds per hour of reactants fed per pound of enzyme catalyst contained within the reactor. WHSV may be 0.01 to about 5 inverse hours. The reaction temperature may desirably be in the range of from about 35° C. to about 60° C. By "substantially equilibrate" is meant that the transesterification reaction is at least 50 percent complete, and preferably at least 90 percent complete. Lower equilibrium transesterification conditions (e.g., 50–90% equilibrated) may be utilized to increase the reaction speed and or reduce the amount of enzyme used, but this increases the stearic acid required and increases the separation step processing requirements.

There is generally an increase in the diglyceride content of the transesterification mixture as a result of excess water in the reaction mixture. The free fatty acid or fatty acid monoester components, which include a mixture of unsaturated fatty acids together with stearic acid, are then separated from the glyceride components. The fatty acid components are subsequently fully hydrogenated to provide a stearic acid source material for blending with the liquid vegetable oil for subsequent, recyclic utilization in the transesterification reaction.

In other embodiments, long chain saturated fatty acids having from 20 to 24 carbon atoms may be used to replace the stearic acid, in whole or in part, as reactants in the transesterification process. Such long chain saturated fatty acids include arachidic acid, behenic acid and lignoceric acid. A particular preferred long chain saturated fatty acid source comprises at least about 80 weight percent behenic acid, based on the total weight of fatty acids. Due to the higher melting points of such long chain saturated fatty acids, the composition as well as the process parameters may be varied to provide compositions having desired solid fat index characteristics. The weight percentage of such long chain saturated fatty acid components of the margarine oils at each of the respective 1-, 3- and 2-positions may be provided as follows:

|  | 1-, 3- Glyceride positions weight percent | 2- Glyceride position weight percent |
| --- | --- | --- |
| Palmitic acid (P) | 5–15 | 0–2.0 |
| Oleic acid (O) | 5–20 | 20–30 |
| Stearic acid | 0–50 | 0–5.0 |
| Linoleic acid (L) | 10–40 | 60–80 |
| Linolenic acid (Ln) | 0–10 | 3–12 |
| Long chain saturated fatty acids (C20–C24) | 5–50 | 0–5.0 |

Illustrated in FIG. 1 is a flow chart illustrating an embodiment of a batch or continuous cocurrent manufacturing method for preparing a firm-bodied margarine oil in accordance with the present invention. In the illustrated embodiment, a liquid vegetable oil 102, which is bleached and deodorized soybean oil, is combined with stearic acid 104 which is at least 94 percent by weight stearic acid, and hexane 106, in a weight ratio of 1:1.15:4 to form a transesterification mixture. The transesterification mixture may desirably be blended before introduction into the reactor 110, by proportional pump metering.

The water 105 may be introduced into the soybean oil 102 or stearic acid 104 at a desired level to maintain enzyme activity at a desired level (e.g., saturated or slightly supersaturated with water) and accommodate and control diglyceride formation in the transesterification reaction. The water 105 may desirably be introduced by conducting the transesterification mixture of soybean oil, hexane and stearic acid through an anionic resin bed or column in which the anionic exchange resin is water-saturated at a temperature of 40°-55° C. The soybean oil, stearic acid, hexane and water are introduced into enzymatic transesterification reactor 110 at a temperature in the range of 35° to 75° C., and preferably about 40°-50° C. The esterification reactor 110 contains an immobilized 1-, 3-positionally specific transesterification lipase, such as the 1-, 3-positionally specific lipase from *Mucor miehei* on a suitable substrate (e.g., NOVO IM 20 Lipase as described in Example 1). Alternatively, the esterification reactor 110 may contain a non-immobilized powdered or granular 1-, 3-positionally specific microbial from a suitable source, e.g., *Mucor meihei, Rhizopus javanicus, Rhizopus niveus, Aspergillus niger, Mucor javanicus, Rhizopus oryzae* or *Rhizopus japonicus, Rhizopus arrhiza*, etc. For example, powdered *Mucor miehei* lipase was packed into a column. A mixture of triolein and linoleic acid (1/1 wt/wt) was saturated with water, and pumped through the bioreactor (column packed with lipase) with a weight hourly space velocity of about 0.75. The resulting effluent was analyzed and contained triglycerides of the following (triolein, dioleic mono linoleic, mono oleic dilinoleic) and diglycerides, indicating interesterification occurred. The *Mucor javanicus* lipase also effected enzymatic interesterification in a system as described above. This process is suitable for production of margarine oil if an appropriate vegetable oil-stearic acid mix is used, or would be suitable for production of vegetable oil low in saturate fatty acids if an appropriate oil (e.g., low saturated fatty acid canola-unsaturated fatty acid mix is used. Alternatively, the esterification reactor 110 may contain a non-immobilized powdered plant 1-, 3- specific lipase, a 1-, 3- specific plant lipase immobilized on an inert solid support (e.g., Celite), or 1-, 3- specific lipase whole seed or whole seedling lipase which is bound to the seed/seedling. Such enzyme lipase may come from castor bean, corn, oat or canola (rapeseed).

Another alternative catalyst is to use a whole cell lipase preparation made by cultivating an organism which produces a 1-, 3- specific lipase such as listed above, such that high quantities of lipase are produced, then processing such lipase-containing broth to yield a dry preparation of high activity and physical and chemical stability. For example, *Rhizopus oryzae* ATCC 24563 is cultivated in shake flasks on medium which was found to give high lipase titre. Suitable media are E4 and E6 as listed in Table AA below. Fifty milliliters of medium was used in a 300 ml. baffled shake flask so good aeration was provided. After a period of 2–7 days, the whole culture broth was harvested as follows: The whole broth was admixed with about 10% powdered dry ice and homogenized in a Waring blender until a smooth consistency was obtained and no lumps or pellets remained. To this mixture was added 0–2% of a suitable cross-linking agent which includes difunctional moieties which can bind to polysaccharides as present in fungal mycelia and/or proteins such as lipase enzymes. Typical cross-linking agents include glutaraldehyde, dimethyl suberimidate, ethylene-maleic anhydride and epicholorohydrin. Additional polysaccharides, e.g., pectin or proteins, e.g., egg white, may be added to alter the mechanical properties of the preparation. In one example, 0.3% epichlorohydrin was added to the culture homogenate. After a reaction period of 0.5–2 hrs., during which the mixture is kept cold, the cross-linked mixture can be directly dried or pelletized and dried. For example, in one case, the epichlorohydrin cross-linked material prepared above was lyophilized to yield a powdered material. Alternatively, the mixture can be spray-dried to yield a granular preparation. In another example, the homogenate, after adding epichlorohydrin, was dispensed dropwise into rapidly mixed hexane, yielding pellets. These pellets were then decanted from the hexane and lyophilized.

TABLE AA

| E4 Medium | Grams/Liter | E6 Medium | Grams/Liter |
|---|---|---|---|
| Soy peptone | 50 | Rice Bran | 40 |
| Tween 80 | 2 | Corn Steep liquor | 30 |
| Dextrose | 10 | | |
| $NaNO_3$ | 1 | | |
| $KH_2PO_4$ | 1 | | |
| Soy Oil | 20 | | |
| $MgSO_4$ | 0.5 | | |

Whole-cell lipase preparations have previously been described (C. Gancet and C. Guizzard, Biocatalysis in Organic Media, p. 261, Elsevier, 1987, W. Okada et al., U.S. Pat. No. 4,935,358, 1990, S. Kyotani et al., J. Ferment. Technol., Vol. 66, pp. 71–83, 1988). Several novel features of the use of a nonimmobilized enzyme preparation are:

1) Homogenization of the whole broth which has been found to increase lipase activity and enable drying by spray drying techniques;
2) Cross-linking said homogenate to improve the physical and mechanical stability of the final catalytic form, preferably with epichlorohydrin;
3) Producing catalytic pellets by shearing said cross-linked homogenate in the presence of a water immiscible solvent such as hexane;
4) Producing granular enzyme catalyst by spray drying the cross-linked homogenate.

It is important to carry out the transesterification reaction under inert gas in a substantially oxygen-free environment in order to prevent oxidation or rearrangement of linoleic and linolenic acid components which are more vulnerable to such oxidation in unrestricted condition. The oil may be vacuum degassed prior to reaction and maintained under oxygen-free nitrogen if desired.

It is known that peroxides and other oxygenated species which may form in the transesterification feed irreversibly deactivate the enzyme and shorten its effective catalytic life. Adding an anti-oxidant to the feed prevents the formation of these deleterious oxygenates and greatly preserves the enzyme activity over time. In one example, addition of 1,000 ppm TBHQ to the feed gave over a ten-fold increase in enzyme half-life, e.g.

from less than 50 hrs. to over 500 hrs. Suitable antioxidents include TBHQ, propyl gallate, BHA, BHT, tocopherol, beta-carotene, etc. Alternatively, the feed can be passed through a column containing a material which selectively adsorbs peroxides and similar species. Such absorbent can be clay or quinone-containing phenolic resin. Such anti-oxidant use has general application to enzymatic methods described herein.

Such transesterification reactions, as indicated, may be batch or continuous cocurrent flow reactions which reach or approach equilibrium as a function of the concentration of components in the mixture. Separation of the fatty acid components from the transesterification mixture is typically a necessary step of such transesterification procedures. In this regard, as shown in FIG. 1, the transesterified reaction mixture which has been transesterified in reactor 110 is conducted to crystallization separator 112. A portion of the hexane may be removed by evaporation prior to introduction into the separator 112 if desired. In the separator, the saturated fatty acid components are precipitated out of solution by reducing the temperature and collecting the precipitate. The saturated fatty acid components, primarily unesterified stearic acid and a small amount of palmitic acid largely derived from the soybean oil 102, is selectively precipitated at temperatures in the range of from $-20°$ C. to about $25°$ C.

The reaction mixture may be seeded with stearic acid and palmitic acid crystals to facilitate precipitation in the separator 112. The precipitated saturated fatty acids 120 may be separated from the remaining transesterified glyceride reaction mixture in an appropriate manner, such as by filtration or centrifugation. The separated fatty acid crystals may be washed with a cold solvent for triglycerides, such as hexane, to remove any liquid glyceride components entrapped with the saturated fatty acids 120. The glyceride stream 122 from the separator 112 comprises the transesterified glyceride component, the unsaturated fatty acids displaced from the soybean oil 102 upon transesterification, which are not precipitated in crystallization separator 112, and the remaining saturated fatty acids which had not previously crystallized together with at least a portion of the hexane solvent. The solvent may be removed by evaporation and returned to the solvent storage vessel for regular use. The glyceride stream 122 is conducted to a vacuum distillation apparatus 124, for removal of the remaining fatty acids and any hexane present in the mixture. The distillation may be a conventional steam deodorizer distillation apparatus at a temperature of 204 to 274° C. at a vacuum of 1.0 to 25 Mm of mercury. The vacuum distillation will be carried out in accordance with conventional steam stripping practice to reduce the fatty acid content to less than 0.10 weight percent, and preferably less than 0.05 weight percent, to provide a margarine oil product stream 126, and a fatty acid distillate stream 128. The fatty acid stream 128 is predominantly $C_{18}$ unsaturated acids derived from the original soybean oil 102. Stearic and palmitic acids may be present in this stream. The palmitoleic and other intermediate chain unsaturated fatty acids may typically constitute less than 0.2 weight percent of the unsaturated fatty acid stream 128. The unsaturated fatty acid stream 128 is introduced into hydrogenator 130 (which may be of conventional design), where the unsaturated fatty acids are fully hydrogenated to provide a stearic acid stream 132. The stearic acid streams 120, 132 may be subjected to fractional distillation in distillation apparatus 134 to separate intermediate chain fatty acids 138 having less than 18 carbon atoms, and to provide purified stearic acid streams 136 for introduction into stearic acid source vessel 104. In this regard, for example, the lower molecular weight saturated fatty acids may be readily distilled off under vacuum conditions without damage to the saturated stearic acid. The margarine oil 126 may be provided which has a desirable, broad solid fat index, a smooth mouthfeel, a trans- acid content of less than 6 weight percent, and an intermediate saturated fatty acid content of less than 6 weight percent.

While crystallization and distillation techniques are described in the embodiment of FIG. 1 for component separation, supercritical or subcritical inert fluids such as supercritical carbon dioxide, supercritical hydrocarbons such as propane, or fluorocarbons or such subcritical pressurized liquids near the critical temperature may be used to selectively dissolve, precipitate or otherwise separate fatty acids, triglycerides and other edible fat and oil components to provide low trans- acid, low intermediate chain fatty acid margarine oils. Counter-current subcritical liquefied gas separation methods utilizing a cosolvent such as ethanol (e.g., at a level in the range of from about 0.5 to about 5 percent, based on the weight percent of subcritical liquefied gas, as described hereinafter) are desirable methods for separation of fatty acids, mono- and diglycerides.

Selective enzymatic interesterification of a batch or continuously flowing homogenous mixture of fatty acids and triglyceride oils followed by separation of the oil, and fatty acid components, by means of various separation techniques and methods such as short path molecular distillation, crystallization fractionation, adsorption-desorption separation, membrane separation (e.g., using zeolitic membranes), counter-current solvent separation, selective complex formation and the like may be used to provide products in accordance with the present disclosure. However, such methods have significant limitations in terms of enzyme utilization efficiency, reactant ratios, and potential end products. Counter-current transesterification, esterification and/or interesterification systems may also be utilized, which establish a counter-current reactant/reaction-product gradient in the reaction zone. Such counter-current systems may also be used to self-separate reactant and reaction components such as fatty acids and/or fatty acid monoesters, from the transesterified oils or other products. Such counter-current processes and systems, which are an important aspect of the present disclosure, may typically use less fatty acid/monoester reactant, and may use enzymes at high efficiency, permitting smaller enzyme reaction zones and reducing enzyme costs.

In order to provide counter-current systems, a plurality of at least 2 phases is provided which are respectively selective toward different components of the reaction system, and which may be transported in a counter-current manner relative to each other. One example of a such counter-current system utilizes a subcritical (e.g., in a range from about 30° C. below, and preferably from about 10° C. below, the critical temperature of the liquefied gas, to the critical temperature of the liquefied gas) liquefied gas such propane, ethane, ethane/methane mixtures, propane/methane mixtures, fluorocarbons, carbon dioxide and mixtures thereof under conditions at which the liquefied gas is partially immiscible with triglyceride oils, and preferentially dissolves fatty acids/and/or fatty acid monoesters in respect to triglycerides. In this regard, the subcritical liquefied gas tends to lose its solvent power as it approaches its critical temperature, typically as a function of effective molecular weight of the solute. Accordingly, higher molecular weight compounds, such as fatty triglycerides, become less soluble than lower molecular weight compounds such as free fatty acids or fatty acid monoesters of lower alkyl alcohols. Under conditions of phase separation, compounds which are more soluble in the liquefied gas phase are selectively retained in this phase. A subcritical liquefied gas such as propane or ethane, preferentially carrying the fatty acids, is also much lighter than the triglyceride phase, so a gravity or centrifugal counter-current system can be established in which the triglyceride phase goes "down", and the fatty acid phase goes "up". Similarly, the subcritical liquefied gas, such as liquid carbon dioxide, or fluorocarbon liquefied gas may be selected to be heavier than the oil phase, so that these relations are reversed. There is also some selectivity for saturated fatty acids unsaturated fatty acids and saturated triglycerides over unsaturated triglycerides in the liquefied, subcritical ethane or propane phase.

While the typical operating temperatures of 70°–95° C. for propane are outside the range for most lipases, cooled lipase-containing reaction zones may be used in a counter-current system, or liquefied gas counter-current solvents may be employed which have a lower critical temperature, such as ethane, ethane/propane mixtures, methane/propane mixtures, as well as $CO_2$, certain fluorocarbons, and mixtures thereof.

Advantages of counter-current transesterification systems include the ability to use relatively small amounts (e.g., 15%) of unsaturated fatty acids compared to the amounts of unsaturated fatty acids used for batch or concurrent processes (e.g., 50%). This means smaller equipment costs, and easier separation steps.

In addition, the enzyme is used at maximum efficiency (i.e., there are fewer reactions "wasted" to reach batch equilibrium), because of the concentration gradients. Additionally, the reaction equilibrium is shifted toward formation of wanted products (triglycerides low in saturated fatty acids) due to enrichment of wanted substrate (unsaturated fatty acids) and removal of unwanted substrate (saturated fatty acids) and unwanted products (e.g., monoglycerides), the latter possibly causing feedback inhibition. This results in lower enzyme cost.

Moreover, selective transport of the saturated fatty acids, and the more saturated triglycerides toward the top of the reaction column, may further increase efficiency in processes for producing certain products, such as unsaturated triglycerides.

LOW SATURATE FATTY ACID FEEDSTOCKS

Low-saturate fatty acid feedstocks may be provided by inexpensive separation techniques such as direct fractional crystallization, which may produce a low saturate fatty acid mixture having reduced saturated fatty acid contents, such as about 3% saturated fatty acids in the unsaturated fatty acid mixture because of the thermodynamic phase relationship of stearic/oleic acids. Other crystallization/fractionation methods such as unsaturated fatty acid/saturated monoglyceride separation methods, as described hereinafter, may produce unsaturated fatty acid feedstock of even lower saturated fatty acid content by using fluorocarbons having a critical temperature, for example, below 95° C., subcritical counter-current reactions may be carried out at a temperature approaching the critical point, without flammability of propane or ethane:

| Fluorocarbon | Critical Temperature °C. | Critical Density g/cm | Critical Pressure |
|---|---|---|---|
| $CBrF_3$ | 67° | .745 | 39.1 Atm |
| $C_2ClF_5$ | 80° | .596 | 30.8 Atm |
| $CHF_3$ | 25.9 | .525 | 47.7 Atm |

Liquid carbon dioxide at subcritical temperatures (e.g., 25°–30° C.) may also be used as an environmentally safe counter-current liquid (having a relatively high density) for such counter-current reaction systems, or may be used at supercritical conditions.

REACTANTS

Broadly stated, the reactants contemplated for use in the disclosed process include all organic materials capable of undergoing an esterification/hydrolysis equilibrium reaction. The reactants can be divided into two categories, those having a carboxylic acid functionality and those having a hydroxyl amine or sulfhydryl functionality. The principal reactants having carboxylic acid functionality include mono-, di- and triglycerides of $C_4$–$C_{22}$ saturated and unsaturated fatty acids and their phosphatide analogs and $C_4$–$C_{22}$ saturated and unsaturated fatty acids and their short chain alkyl esters. Other reactants exhibiting carboxylic acid functionality include fatty acid dimers and trimers, dibasic acids such as adipic, succinic and maleic acids and their anhydrides, unsaturated acids such as acrylic acid and its esters such as ethyl and allyl acrylate and furan fatty acids.

The principal reactants exhibiting a hydroxyl functionality include an 1-, 1,2- and 1,2,3- hydroxy substituted propane, e.g., glycerol and propylene glycol, and $C_4$–$C_{22}$ saturated and unsaturated straight or branch chain mono- or di- primary alcohols. Other reactants exhibiting a hydroxyl functionality include sugars, such as glucose, galactose, mannose, arabinose, fructose, xylene, sucrose, maltose, lactose, etc., and sugar alcohols such as sorbitol, sorbitan, mannitol, xylitol, arabitol, arabinitol, adonitol and dulcitol, furfuryl alcohol and tetrahydrofuran, and a wide variety of products can be made using esterases, lipases (including acyltransferases) proteases, phosphatases, nucleases and phospholipases, which can form or hydrolyze esters, amides, phosphates, thioesters, etc. For example, triglycerides may be prepared in which a polyunsaturated fatty acid, such as eicosapentaenoic acid, DHA, CILA or other highly unsaturated fatty acid is esterified at the 2-position, flanked by stearic acid ester groups at the 1,3 positions of the triglyceride, for purposes of stability.

Unsaturated triglycerides may also be transesterified with reactive esters/acids/alcohols that are sensitive to heat or extreme chemical interesterification conditions to produce reactive solvent-free coatings. Linolenic glycerides such as Tung oil+allyl acrylate (or allyl alcohol or acrylic acid) non-volatile, highly reactive ester mixtures may be obtained:

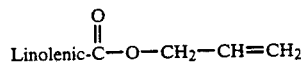

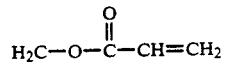

-continued

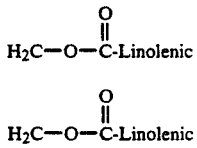

Such coating materials may be solvent-free (avoiding deleterious solvent use in oil paint products), and sufficiently, particularly when formulated with driers and/or sensitizers, reactive to cure or cross-link rapidly under UV or oxidizing conditions.

By using counter-current reaction systems (employing subcritical ethane, propane, fluorocarbons, or supercritical $CO_2$ as a separate phase), reactant and reaction product flows can be controlled to achieve high yields. Ionic materials can be separated and low molecular weight components or reaction products can be separated from higher molecular weight components. Water can be removed by such a counter-current phase to facilitate ester synthesis. Acid anhydrides, such as fatty acid anhydrides, acetic anhydride or mixed anhydrides, also might be used in a counter-current system to effectively remove water, esterify mono- and di- glycerides in a reaction mixture, and achieve ester synthesis. Defunctional acids, such as succinic anhydride may be used to form dimeric/polymeric polyglycerides having. relatively lower caloric content, and special physical properties, or dimeric/polymeric phosphatides having unique emulsification characteristics.

ENZYME

As stated herein, the disclosed processes contemplate the use of a wide variety of exocellular and intracellular or membrane bound esterase, lipase, protease, nuclease, phosphatase, acyltransferase and phospholipase enzymes. Enzymes from plant, microbial, fungal and animal sources and synthetic enzyme sources are contemplated.

The sources of lipase, esterase and phospholipase enzymes, natural plant lipase and/or phospholipase enzyme systems such as those present in oilseeds, e.g., cabbage, sunflower, safflower, soybean, cottonseed, castor bean, canola, cereal and grain seed, e.g. alfalfa, oats, rye, wheat, corn and nuts, e.g., peanuts may be useful and very desirable as "all natural" materials for food manufacture. Yeasts, such as *saccharomycopsis lipolytica Candida cylindracae, Candida lipolytica, Geotricium candidum, Apiotricum curvatum,* are also a source of lipases. However, the major enzymes exhibiting good lipase activity are those derived from bacterial and fungal sources. Well-known examples of fungi which produce lipases are *Rhizopus oryzae, Rhizopus arrhizus, Rhizopus niveus, Rhizopus dilemar, Aspergillus niger, Mucor miehei, Mucor javanicus, Mucor japonicus* and *Rhizopus janonicus.* Bacteria which produce lipases include pseudomonas fluorescens.

Lipase activity in dried seeds or seed components (e.g., soybean seeds, corn seeds) is relatively low. With exception of rice bran and castor bean acid lipase, lipase is typically present in the form of an inactive zymogen which is activated upon seed germination or synthesized de novo upon germination. In order to maximize the lipase activity, it may be desirable to germinate the seeds, to permit them to develop to a point of maximum lipase activity per unit weight, followed by drying under non-denaturation conditions. Maximum lipase activity in many oil seedlings is developed during or shortly after germination. It may be desirable to separate seedling parts having high lipase content from those having little or no lipase content. The dried, lipase-rich material may then be ground, or shredded, extracted with a solvent such as hexane or ether, and used as an inexpensive transesterification/interesterification agent. Because interesterification activity will be diffusion-limited, it may be desirable to create a "porous" dried plant material, by explosive decompression, or by infusing the plant seedling with components prior to drying, which can be extracted after drying of the seedlings to produce a porous mass. For example, sugars may be infused into the seedlings, the infused seedlings dried, and then extracted with a sugar solvent such as pyridine which does not inactivate the lipase, but leaves a porous, dried structure.

The effective activity and accessibility of cell-bound lipase may also be increased by non proteolytic enzyme treatment which removes seedling components which interfere with lipase accessibility. In the case of lipases which are membrane-bound, treatments which expose the lipase by removing inactive shielding components increase activity, and increase the lipase weight ratio. Such treatment may include cellulase or other polysugar hydrolyzing enzyme treatment e.g., treatment of cereal grain seedlings with α-amylase to degrade endosperm starch to expose bound lipase, or acid/base treatment of the germinated plant material.

Process economics generally dictate that the enzyme component catalysts be reusable, i.e., they are retained in the reaction zone through which the reactants flow or are easily separable from the finished products and by-products at the conclusion of the reaction, e.g., by filtration, centrifugation and the like. There are a myriad of ways to render enzymes reusable, generally dependent on the particular enzyme, and many of the techniques for accomplishing this result are well-known.

A well-known technique is to immobilize the enzyme by chemically bonding it to, adsorbing it on, or absorbing it in an insoluble material such as a resin, diatomaceous earth, etc. The art is replete with examples of immobilized enzyme/resin combinations and no attempt is made to set forth all of the various possibilities that might be employed in conjunction with the disclosed processes.

It is also known to cultivate a fungal mycelium such as *R. arrhizus* containing membrane bound enzyme which is freeze dried, milled and sieved to provide an insoluble biomass that can be supported in a fixed bed reactor. It is also possible to disperse an enzyme in the dispersed water droplets in a micro-emulsion containing reversed micelles. Chen et al., J. Food Sci., Vol. 56, No. 1, pp. 234–7 (1991). The micelles may be retained in the reaction zone by means of a hydrophobic membrane.

In addition to the foregoing, that lipase enzyme formulations of good enzymatic activity may be prepared by cross-linking whole microbial cells with a suitable cross-linking or binding agent such as epichlorohydrin, glutaraldehyde, dimethylsuberimidate, ethylene maleic anhydride or other difunctional agent which are formed into micro porous pellets having sufficient mechanical properties to permit use in a continuous bioreactor for interesterification of oils and fats or other applications.

Whole microbial cultures contain intracellular and extracellular lipase enzymes useful for interesterification and other purposes generally have poor mechanical properties and enzymes may be eluted during continuous bioreactor operation.

Variations include lipase catalysts for hydrolysis or other purposes and for non-lipase enzymes, e.g. amylases. This process is preferably applied with fungal species but can be applied with any microbial species.

EXAMPLE 1

*Rhizopus oryzae* was inoculated in E4 medium (Table AA) and grown at 30° C. for 4 days. The whole broth was homogenized in a Waring blender with admixed dry ice. To the homogenate was added 1% epichlorohydrin and 50 ml. of the mixture dropped into 300 ml. of hexane under rapid agitation. The homogenate became dispersed as spherical beads which upon continued holding became semi-solid due to cross-linking of the mycelium. The beads were decanted from the hexane, washed twice with Tris buffer, pH 7, 0.1 M and lyophilized. The dried beads were found to contain high lipase activity as shown by p-nitrophenol butyrate assay.

EXAMPLE 2

The homogenate of example 1 was mixed with epichlorohydrin and after standing for 5–60 min., extruded into cylindrical extrudates using a meat grinder. The extrudates were cut into cylindrical pellets of length 0.25–0.5", washed with buffer and lyophilized. The dried pellets were found to have high lipase activity.

EXAMPLE 3

The whole broth of example 1 was homogenized sufficiently to allow passage through a 30 mesh screen. Epichlorohydrin was added to the filtered homogenate and the mixture spray dried at exit temperatures held at 50°–100° C. Dry pellets of high lipase activity were obtained.

EXAMPLE 4

To the homogenate of examples 1–3, 1% of citrus-derived pectin was added prior to admixture with epichlorohydrin. Pellets of greater rigidity than those obtained in examples 1–3 were obtained.

Phospholipase A-2 may be used to transesterify or synthesize highly unsaturated fatty acids such as CLA, EPA, DHA, into the 2-position of phospholipids, to produce healthful, functional compounds. The 2-CIA/Omega-3/etc. phospholipid may be a relatively stable solid at ambient temperature, and may have useful surface active or other functional characteristics. The highly unsaturated phospholipid compound may be converted into a triglyceride by appropriate use of phospholipase C to remove the phosphate group in the sn-3 position, followed by 1,3 lipase acyl ester synthesis. Similarly, phospholipase D could be used to provide phosphate compounds (upon hydrolysis) or to provide uniform or controlled phospholipid compositions via transphosphatidylation under low water "transesterification" conditions.

Relatively pure stereoisomers of triglycerides or phospholipids may also be provided using stereospecific enzymes, which are different from random mixtures. Stereospecific, or regiospecific, designed oils may permit selective metabolic control of biological use of designed healthy oil components by human metabolic processes.

Lipases, esterases and phospholipases are active with a wide variety of compounds, in addition to glycerol and fatty acids.

Esterases/lipases may be used, particularly using counter-current processes as described herein, to produce a wide variety of products which are difficult to produce under conventional conditions. Sugar, dextrin or cyclodextrin solution droplets with lipase enzyme dissolved therein may be emulsified in a triglyceride mixture as a reactive phase. Esterases or non specific lipase may be used, rather than 1,3 specific lipases, to produce di- or tri-substitution. Mono di- or tri-substituted sugars or cyclodextrins or polysaccharides are useful compounds, as surfactants, flavor/sweetener entrapping agents, artificial fats, etc.

While the system of FIG. 1 is a batch, continuous flow or cocurrent reaction system, counter-current transesterification methods may also be used to provide enzymatically transesterified margarine oils. However, as indicated herein, counter-current reaction systems may provide higher efficiency and effective component separation.

Because of the mutual solubility of the triglyceride and fatty acid or fatty acid monoester reaction components, counter-current processes utilizing counter-current supercritical fluids which selectively extract and transport the fatty acid may desirably be utilized to provide efficient transesterification of the recycled stearic acid components. Counter-current transesterification procedures may not only provide the reaction efficiencies of counter-current operation, but also may facilitate separation of reaction products.

In supercritical fluids such as supercritical carbon dioxide, solubility of fatty acid esters such as fatty acid methyl and ethyl esters are typically an inverse function of molecular weight of the fatty acid monoester under various conditions. Similarly, the solubility of fatty acids is inversely proportional to molecular weight of the fatty acid, although fatty acids are typically less soluble in supercritical carbon dioxide, than corresponding fatty acid lower alkyl monoesters of corresponding molecular weight because of the associative or hydrogen bonding characteristics of the fatty acids. The respective solubilities of fatty acids, fatty acid esters and triglycerides in carbon dioxide is also a function of temperature and partial pressure of $CO_2$ at relatively low supercritical pressures, above the critical pressure for $CO_2$ of about 72.8 atmospheres (at critical temperature of 31.1° C.).

An embodiment of a continuous transesterification process which moves a fatty acid or fatty acid monoester component counter-current to the triglyceride flow, and which also removes such fatty acid transesterification reaction components from the transesterified glyceride, is illustrated in FIG. 2.

The high $C_{18}$ vegetable oil to be trans-esterified, which in the illustrated embodiment is soybean oil 212, is saturated with water and introduced into the high pressure column 214 at a point 224 between the upper outlet 216 and the lower stearic acid source material inlet 222. Alternatively, it may be desirable to reduce the water content to subsaturation. The saturation point of the oil to be 0.4% water. Operating the reactor at a lower water content, e.g., 0.2%, was found to alter the product distribution, i.e., reduce the amount of mono- and diglycerides formed. The soybean oil may be conducted through a column containing a water-saturated anionic exchange resin to remove non-triglyceride impurities which might poison the enzyme, and condition the oil for the reaction. The rate of introduction of the soybean oil 212 corresponds to the transesterification reaction rate permitted by the activity of the immobilized enzyme in the column 214. In this regard, the column is packed with an immobilized lipase enzyme, which is immobilized on organic or inorganic, high surface area supports such as porous ceramic rings or pellets, organic supports such as crosslinked ion exchange or phenolic resins which are insoluble in the supercritical fluid, or diatomaceous earth (e.g., Celite). The surface area of the column packing is very large in order to promote interesterification reaction (e.g., more than 750 square meters of surface area per cubic meter), and to promote equilibrium dissolution of the low molecular weight components in the supercritical fluid. As an alternative to immobilized lipase, non-immobilized powdered or granular microbial lipase or cross-linked whole microbial lipase or powdered animal lipase, or powdered or cross-linked whole plant cell lipase immobilized as previously described may be used. These materials can be used in a packed-bed column reactor similar to that employed for immobilized lipase, or can alternatively be used in a fluidized-bed reactor, ebullating bed reactor or continuous stirred tank reactor. Non-immobilized powdered lipase and whole-cell cross-linked fungel lipase containing powder can be used in a packed bed reactor for operations in excess of 200 hrs.

Stearic acid or preferably a lower alkyl stearic acid monoester 220, such as a methyl or ethyl ester of stearic acid (e.g., ethyl stearate), which is desired to be transesterified with the triglyceride 212, which may be saturated with water is introduced into the column 214 at a point 222 between the point 224 of introduction of triglyceride, and the lower outlet 218 at a rate which maximizes the desired transesterification reaction. Because this transesterification reaction is conducted in a counter-current manner, a lower ratio of stearic acid source material components to soybean oil may be used. Lower alkyl monoesters of the stearic acid source material are preferred because they have higher solubility in the supercritical gas.

In operation, supercritical carbon dioxide (or another supercritical fluid, or a subcritical liquefied gas such as an ethane-propane mixture or a subcritical liquefied fluorocarbon gas having a critical temperature for example in the range of from about 30° C. to about 80° C.), is introduced at the bottom of the column 214 under pressure and temperature conditions at which relatively low molecular weight fatty acids or fatty acid esters such as stearic acid and ethyl stearate are significantly dissolved, but at which the high molecular weight triglycerides are relatively not substantially dissolved. For example, carbon dioxide pressures in the range of from about 1,100 psi to about 4,500 (e.g., 2,000–3,000 psia for ethyl stearate use), at a reaction temperature in the range of, for example, from about 30° C. to about 40° C., are particularly preferred to provide relatively high fatty acid and/or fatty acid monoester solubility, while providing relatively low triglyceride solubility in the upwardly moving supercritical carbon dioxide stream. Such conditions of pressure and temperature may be provided in which the density of the supercritical gas is less than that of the triglyceride components, so that counter-current flow is readily achieved. The supercritical fluid may contain a small amount of water vapor to maintain the catalyst and to facilitate fatty acid solubility in the supercritical gas phase. The temperature, of course, cannot exceed the operating temperature of the enzyme, which will be damaged at high temperatures. In this regard, at lower supercritical pressures, the solubility of the fatty esters and triglycerides is higher at lower temperatures, and a temperature should be selected (e.g., 35°–55° C.) which maximizes throughput rate for counter-current transport of the fatty monoester, and the transesterification reaction rate which is necessary to achieve transesterification of the triglyceride and the fatty acid or fatty acid monoester. Fatty acid monoesters, such as methyl and ethyl stearate and the transesterified reaction product monoesters are substantially more soluble in the supercritical fluid than the corresponding acids, and accordingly are preferred reactants. The supercritical gas also serves as a diluent of the triglyceride phase to decrease the viscosity rate.

The supercritical carbon dioxide gas phase is less dense than the downwardly moving liquid soybean oil stream at pressures used in the system of FIG. 2 (e.g., 1,500–3,500 psia), and the density difference provides the counter-current flow in the system. The pressure, temperature, column distances and flow rates of fatty acid or fatty acid monoester and carbon dioxide are selected so that in the zone 224 between the point of introduction of the carbon dioxide and the point 222 of introduction of the stearic acid or monoester, the fatty acid or fatty acid monoester is progressively dissolved from the triglyceride into the upwardly moving supercritical $CO_2$ stream. The zone 224 is primarily a stripping zone in which the fatty acid and/or fatty acid monoester components are removed from the transesterified oil product. The fatty acid or fatty acid monoester components (including the transesterified components) may be substantially completely removed from the triglyceride stream 226 before it is discharged from the column at outlet 218. In this regard, the weight ratio of the flow rate of the carbon dioxide to the flow rate of the stearic acid component 220 introduced in the column 214 may desirably be selected to be in the range of from about 5:1 to about 50:1, under conditions to maximize solubility of the fatty acid or preferably fatty acid monoester component while minimizing the solubility of the triglyceride component phase. In the zone 224, during the time of transit of the soybean oil (e.g., 0.25–6 hours), the stearic acid monoester 220 undergoes transesterification with the triglyceride component. Because the flow of triglyceride and stearic acid or monoester is effectively diminishingly cocurrent in this stripping zone, the enzymatic transesterification reaction will tend to approach the equilibrium condition of the fatty acid monoester-triglyceride blend at the point 222 of introduction of the monoester. Accordingly, the composition of the fatty acid or fatty acid monoester which enters the counter-current transesterification zone 226 from the monoester stripping zone 224 will be different from the composition of the fatty acid or monoester 220 introduced into the column 214 at least in part because of the transesterification which occurs in the stripping zone 224. The transesterified triglyceride margarine oil product, which may have substantially all fatty acid and fatty acid monoester components removed therefrom, is withdrawn from outlet 218. The weight ratio of triglyceride components to the stearic acid or monoester component to achieve a desired degree of transesterification of the triglyceride is substantially greater in the system of FIG. 2 than the ratio of triglyceride to fatty monoester utilized to achieve an equivalent degree of transesterification in a one or two step batch reaction. In this regard, the stearic acid or stearic acid monoester is introduced into the bottom of the column at a rate compared to the rate of introduction of soybean oil which may, for example, be about half the proportion used in a batch reaction (e.g., 1:3 to 1:1 weight ratio of stearic acid component to soybean oil).

The fatty acid or monoester component is dissolved in the upwardly moving $CO_2$ gas stream and carried into the transesterification zone 226, where it tends toward approaching equilibrium through exchange with the composition of fatty acids or monoesters in the counter-current oil flow, while this composition is also being changed, through the action of the immobilized enzyme in the column. Accordingly, the fatty acid or monoester component dissolved in the supercritical gas is effectively transesterified in a counter-current manner with the liquid triglyceride stream as it is conducted from its point of introduction 224 to the point 220 of introduction of the fatty acid monoester.

The triglyceride phase mixture continuously undergoes transesterification reaction as it moves downwardly in the zone 226 containing lipase enzyme counter-current to the flow of supercritical gas, such that the mixture has an increasing concentration of the desired triglyceride components as it moves down the column. There is also an increasing concentration of transesterified fatty acid or monoester having fatty acid or monoester components derived from the triglyceride in the upwardly moving supercritical gas stream, in the direction toward the point of introduction of the triglyceride. Water vapor may be included in the carbon dioxide flow, the fatty acid ester flow and/or the triglyceride flow to accommodate the transesterification reaction, which may exceed the solubility of water in the triglyceride component, and to produce a desired level of diglycerides. Fatty acid components produced by hydrolysis reactions in the column 214 may also be removed by the supercritical carbon dioxide flow.

The transesterified fatty monoester dissolved in the supercritical $CO_2$ gas stream is carried from the column at outlet 216, through pressure let-down valve 230 into separation tank 232, where dissolved fatty acid monoester is taken out of supercritical solution as a result of the pressure reduction. The tank 232 may alternatively be heated to further reduce the solubility of the fatty acid monoester. The solubility reduction may also be accomplished by a combination of a limited pressure reduction (e.g., by 500–1,000 psi) and a temperature increase (e.g., to 70°–100° C.) so that the work to recompress the $CO_2$ for recycle use may be reduced. Alternatively, and preferably, the pressure letdown system will desirably be an energy recovery system, such as a piston or turbine engine in which the pressure let-down work is recovered and dissolved components are collected in the recovery system, so that the pressure let-down energy may be at least partially recovered for recompression of the carbon dioxide upon recyclic operation.

The carbon dioxide which is separated from the fatty acid or monoester is conducted to compressor/thermal conditioner 234 where it is recompressed and reintroduced at the preselected operating temperature as previously discussed. A heat-pump 236 may be used to transfer heat between the compressor 234 and the separator 232 and/or pressure let-down valve 230. If an energy recovery system is used, the pressure let-down piston or turbine motor will desirably be on the same or a directly connected shaft as the compressor. The flow rate of supercritical carbon dioxide (or other supercritical gas solvent) through the column 214 is correlated with the flow rate of fatty acid ester 220 so that it is adequate to dissolve substantially all of the fatty acid monoester under the operating conditions, but dissolves a minimal amount of the initial soybean oil and other triglyceride components. The solubility of the fatty acid or fatty monoester components will desirably be greater than 1 weight percent, and preferably greater than 2 weight percent, while the solubility of triglycerides will be less than 0.5 weight percent and preferably less than 0.25 weight percent in the carbon dioxide gas phase.

If desired, the transesterified fatty acid or monoester collected in the separator tank 232 is conducted to a hydrogenation reactor 240 to fully hydrogenate the unsaturated fatty acid components to provide a predominantly stearic acid fatty monoester for reintroduction into the column 214 at point 222, as shown in FIG. 2. The hydrogenated fatty acid components may be distilled to remove $C_{12}$–$C_{16}$ fatty acids, and may be esterified with a lower alkyl monohydric alcohol such as ethanol prior to or subsequent to such distillation. Intermediate chain fatty acid components may be selectively fractionated from the recycle mixture after hydrogenation. While the system of FIG. 2 utilizes supercritical gas, such counter-current methods may also utilize a subcritical liquefied gas such as propane, propane/ethane mixtures, and liquified fluorocarbon gases, as further described herein, having a critical temperature in the range of e.g., 30° C.-90° C. Such systems, at temperatures near (e.g., within 20° C. lower than) the critical temperature, exhibit selective solubility of fatty acids and monoesters in 2-phase systems, and generally may be used as described in a manner similar to that of FIG. 2 at elevated pressures sufficient to maintain the subcritical solvents in the liquid state. The counter-current system of FIG. 2 may also be used for a wide variety of transesterification, esterification, and separation reactions in addition to those which produce the margarine oils or cocoa butter substitutes. It will also be appreciated that by increasing the ratio of saturated fatty acid/monoester to triglyceride used in the reaction zone, the counter-current process of FIG. 2 may be used to produce 1-, 3- disaturated glycerides at very high efficiency and high purity. Such 1-, 3- disaturated triglycerides are useful as cocoa butter substitutes or extenders.

COCOA BUTTER

The disclosed processes may also be utilized to prepare a synthetic cocoa butter from inexpensive raw materials. Natural cocoa butter contains substantial quantities of unsaturated $C_{18}$ fatty acids at the 2-position, position, the 1- and 3-positions being primarily palmitic and stearic residues. If the palmitic acid components of the recycle stream is retained, the cocoa butter substitute will contain palmitic esters in the 1-, 3-positions with the stearic acid esters. If the palmitic acid component is reduced or substantially removed before counter-current introduction, a 1-, 3- distearoyl triglyceride product of relatively high purity may be prepared. It is this combination of saturated and unsaturated residues that gives cocoa butter the melting point characteristics which makes it highly desirable in the confectionery industry. Natural cocoa butter, however, is in short supply and is relatively expensive as compared to other triglycerides.

The disclosed processes may be utilized to esterify relatively inexpensive triglyceride fractions derived from palm oil and olive oil containing significant amounts of 2-unsaturated fatty acids with palmitic and stearic acids and/or esters in the presence of a 1,3 specific lipase to provide a synthetic triglyceride having the melting characteristics and mouthfeel of cocoa butter. In this connection, 62 grams of a palm oil mixed with 38 grams of stearic acid and dissolved in a hexane solvent. 2.0 grams lipase S (G. B. Fermentations) enzyme is added and the reaction is carried out under stirring at 40° C. for 92 hrs. After separation of enzyme and solvent, a triglyceride is obtained having the following fatty acid distribution. The product had the mouthfeel and a differential scanning colorimeter profile which closely mimics natural cocoa butter.

| Fatty Acid Distribution (wt. %) | |
| --- | --- |
| Palmitic (P) | 27.4 |
| Stearic (S) | 31.5 |
| Oleic (O) | 30.1 |
| Linoleic (L) | 8.6 |
| Linolenic (Ln) | 0.4 |

A very efficient counter-current process, such as that illustrated in FIG. 2, may be provided by producing 1-, 3-disaturated glyceride products, as previously indicated. Another aspect of the present invention for manufacture of tailored triglycerides is directed to providing a lipid composition for use as a cholesterol free, low saturate, butterfat (milkfat) substitute, derived from vegetable oils, having flavor generating potential and thermal melting characteristics similar to butterfat. The lipid composition is particularly suitable for cheeses and cheese products.

Cheese is a concentrated dairy product that requires select microorganisms and their enzyme systems to develop characteristic flavor and texture. Cheeses consist of varying ratios of milk proteins, fat and moisture; they may be made from whole milk, partly skimmed, skim milk or whey and may or may not contain added cream or nonfat dry milk solids. Casein is usually coagulated with rennet and tactic acid or with other suitable enzymes and acids. Ripening agents may vary from none to select strains of bacteria, yeasts and molds. Factors having the greatest affect on the composition of the finished cheese are source of milk (cow, ewe, goat, buffalo), fat content, ratio of casein to milk solids and method of manufacture.

As an example, cheddar cheese is a hard, close-textured, bacteria ripened variety of cheese that requires several months of curing at low temperatures to develop the characteristic flavor. A large portion of the flavor is derived from the hydrolysis of protein to peptides and amino acids and the hydrolysis of milk fat to free fatty acids. During cheese ripening, the hydrolysis of butterfat to yield free fatty acids from $C_4$–$C_{10}$, in particular $C_4$ and $C_6$, and their subsequent microbial metabolism leads to the production of certain desirable flavors in cheese.

Butterfat is substantially complex and contains an extraordinary variety of component fatty acids including volatile fatty acids and high levels of cholesterol, a substance linked to heart disease. Every member of the saturated acid series from butyric ($C_4$) to behenic ($C_{22}$) is present and each member of the monoethenoid series from decenoic to octadecenoic. octadecadienoic acids are present in significant amounts as well as traces of hexadecadienoic acid, octadecatrienoic acids and highly unsaturated $C_{20}$ and $C_{22}$ acids. The average composition of butterfat has been reported in Bailey, Industrial Oil & Fat Products, 3d Ed., Interscience Publishers, Inc. (1964), p. 168, as follows:

| Saturated Fatty Acids | Average Composition of fatty acids, wt. % |
| --- | --- |
| Butyric | 2.8–4.0 |
| Caproic | 1.4–3.0 |
| Caprylic | 0.5–1.7 |
| Capric | 1.7–3.2 |
| Lauric | 2.2–4.5 |
| Myristic | 5.4–14.6 |
| Palmitic | 26–41 |
| Stearic | 6.1–11.2 |
| Above $C_{18}$ | 1.2–2.4 |

Fatty acids can be classified as short, intermediate or long chain. Short chain fatty acids are fatty acids having from 1 to 6 carbon atoms, particularly acetic, propionic, butyric and caproic. Intermediate chain fatty acids are fatty acids having from 7 to 17 carbon atoms, particularly including caprylic, caproic, lauric, myristic and palmitic. Long chain fatty acids are fatty acids having 18 or more carbon atoms, particularly stearic.

Intermediate chain dietary saturated fatty acids, notably lauric ($C_{12}$), myristic ($C_{14}$) and palmitic ($C_{16}$) acids common to coconut and palm oils and many natural and processed food products, have been reported in the medical literature as being a factor in the elevation of plasma cholesterol in populations at risk for coronary heart disease. However, stearic acid, although it is a saturated fatty acid, has been reported to have minimal or even reducing effect on cholesterol level ["Effect of Dietary Stearic Acid on Plasma Cholesterol and Lipoprotein Levels", Bonanome, et al., New England Journal of Medicine, Vol. 318, 1244–172 (1988)]. Accordingly, triglyceride oils which have low ($C_{12-16}$) intermediate chain fatty acid content would be desirable.

This embodiment of the present invention is directed to a lipid composition which can be used as a butterfat substitute and which has a solids fat index and $C_4$–$C_{10}$ profile similar to butterfat, but which is far less complex in composition than butterfat. As compared to butterfat, this lipid composition has far less myristic ($C_{14}$), palmitic acid ($C_{16}$) and far more stearic acid ($C_{18}$). These lipid compositions also differ from those of butterfat in that the levels of saturated fatty acids from $C_{12}$ to $C_{16}$, particularly myristic acid and palmitic acid are far less than those of butterfat.

The butterfat substitute lipid compositions of the present invention have from about 1% to about 5% of butyric acid, from about 1% to about 5% of caproic acid, from about 2% to about 6% of palmitic acid, from about 20% to about 45% of stearic acid, from about 10% to about 35% of oleic acid, from about 10% to about 35% of linoleic acid and from about 1% to about 10% of linolenic acid, and may also have from about 0%–2% caprylic acid and from about 0%–4% caproic acid. In particular, the myristic acid level of the butterfat substitute lipid compositions of the present invention is less than about 1%, whereas butterfat usually has about 11–12% of myristic acid and palmitic acid is reduced to less than 5% from the 24% level in butterfat.

The butterfat substitute lipid compositions of the present invention have a low, but significant level of $C_4$, $C_6$, $C_8$ and $C_{10}$ saturated fatty acids and have a unique combination of $C_{16}$ and $C_{18}$ saturated fatty acids and $C_{18}$ unsaturated fatty acids. The butterfat substitute lipid compositions of the present invention may be manufactured by any of the heretofore described interesterification methods.

As used herein, the weight percent of saturated or unsaturated fatty acid moieties in a glyceride composition is calculated based on the total weight of the fatty acids contained in the oil composition. As used herein, when referring to weight percent of one or more fatty acid moieties of a margarine oil, the weight percent is calculated based on all of the fatty acid moieties of the composition being hydrolyzed to free fatty acid. The weight percent of one or more species of fatty acid moiety is then calculated as the weight percent of such one or more species based on the total weight of free fatty acids. AOCS official method Ce 1-62 (81) may be used to determine the weight percent of respective fatty acid moieties.

The butterfat substitute lipid compositions of the invention have a minimal amount of intermediate chain saturated fatty acid moieties. In this regard, the margarine oil product comprises less than about 10 weight percent and preferably less than about 6 weight percent of intermediate chain saturated fatty acids based on the total weight of the product. Specifically, the total content of palmitic, caprylic, caproic, myristic, and lauric acids, or mixtures thereof, in free or esterified form, is less than 10 percent of the total weight of the fatty acid content of the butterfat substitute lipid compositions of the present invention and preferably less than 6 weight percent. The myristic acid content is preferably less than 1 weight percent and the palmitic acid content is preferably less than 5%.

The butterfat substitute lipid compositions have a wide variety of glyceride components and a higher amount of unsaturated fatty acids than butterfat. In this regard, the butterfat substitute lipid compositions have a linoleic acid moiety content of from about 10 to about 35 weight percent and preferably from about 15 to about 30 weight percent and from about 1 to about 6 weight percent of linolenic acid moieties and preferably from about 2 to about 5 weight percent linolenic acid moiety. Linolenic acid may generally be provided as a component of the soy oil or other linolenic acid containing oils, such as canola oil, used as a starting material. Alternatively, linolenic acid can be provided during the interesterification process to increase esterified linolenic acid content of oils having a low linolenic acid content, such as corn oil and safflower oil. Further in accordance with the present invention, the butterfat substitute lipid compositions have an oleic acid content of from about 10 to about 35 weight percent and preferably from about 12 to about 30 weight percent. Moreover, the butterfat substitute lipid compositions comprise from about 84 to about 95 weight percent of triglycerides, and preferably from about 88 to about 92 weight percent triglycerides. The butterfat substitute lipid compositions of the invention have relatively high diglyceride content, which is believed to contribute to the smooth organoleptic properties and the solid fat melting index profile characteristics of the product. In this regard, the diglyceride content of the oil will generally be in the range of from about 5 to about 16 weight percent and preferably from about 8 to about 12 weight percent. The monoglyceride component is generally less than about 1 weight percent and preferably is less than about 0.5 weight percent, based on the total weight of the butterfat substitute lipid compositions. The weight percent of monoglycerides and diglycerides is determined based on the actual weight of the mono and/or diglyceride component, as a percentage of the total weight of mono-, di- and triglycerides of the butterfat substitute lipid compositions.

An important aspect of the butterfat substitute lipid compositions of the present invention is the provision of a broad melting range. The butterfat substitute lipid compositions should have a solid fat index which decreases from a value in the range of from about 7 to about 31 percent at 10° C., a typical refrigeration temperature, to a value of less than one percent at 38.7° C., a value slightly higher than body temperature. Butterfat substitute lipid composition oils in accordance with the present invention are characterized by solid fat index profiles as follows:

| Dilatometric Temperature | Solid Fat Index Percent |
|---|---|
| 10° C. | 7-31 |
| 21.1° C. | 3-25 |
| 26.7° C. | 0.75-10 |
| 33.3° C. | 0.5-4 |
| 37.8° C. | less than 1 |

The specified solid fat indexes at the specified temperatures are measured by dilatometric methodology in accordance with AOCS procedure Cd 10-57. The dilatometric procedure measures volume changes in a fat or margarine oil as a function of temperature, which changes are a function of the relative proportion of solid and liquid fats. The solid fat index is a dilatometric index on a percentage scale of 0 (for no solid fat) to 100 (for all solid fat).

The oils of the present invention may be provided using immobilized microbial, animal or plant enzyme, non-immobilized powdered microbial, animal or plant enzymes or whole cell microbial, animal or plant systems as previously described and an inexpensive oil source such as soybean oil in a precise sequence of transesterification, separation, full hydrogenation of fatty acids liberated during transesterification and recycle steps.

Generally in accordance with the present invention, the butterfat substitute lipid compositions may be provided by enzymatic transesterification of an edible liquid vegetable oil comprising at least about 73 and preferably 80 weight percent of eighteen carbon fatty acid moieties ($C_{18}$ saturated and unsaturated fatty acids) based on the total weight of the edible liquid vegetable oil. Such $C_{18}$ fatty acid moieties include stearic acid, oleic acid, linoleic acid and linolenic acid. In addition, the edible liquid vegetable oil should comprise less than 14 weight percent of esterified palmitic acid.

The liquid vegetable oil may desirably further comprise at least about 15, and more preferably at least about 22 weight percent of esterified oleic acid in the liquid vegetable oil. In addition, the liquid vegetable oil will preferably comprise at least about 20 weight percent of esterified linoleic acid, and at least about 0.2 and preferably at least 5 percent of esterified linolenic acid. Sunflower, soybean, safflower, corn, olive and canola (low erucic acid rapeseed) oils or blends thereof may be used as starting material for the manufacture of butterfat substitute lipid compositions in accordance with the present invention. Soybean and canola oils are particularly preferred starting materials due to their high linolenic acid content. Other vegetable oils such as sunflower, safflower and olive oil can be used as starting oils, but these oils must be interesterified in combination with free linolenic acid. In addition, blends of these oils can be used.

The manufacturing processes for preparing the butterfat substitute lipid compositions may be carried out in batch mode, continuous flow mode or in continuous cocurrent or counter-current mode as previously described. Batch processes may be carried out in a single transesterification step or multiple steps. The use of multiple steps permits use of lower stearic acid/liquid vegetable oil ratios in each step, but requires multiple separation steps. Single step batch or cocurrent continuous processes require relatively high ratios of stearic acid to liquid vegetable oil in the initial reaction mixture, but are generally more economical than multi-step processes.

In accordance with such manufacturing methods, the high $C_{18}$ liquid vegetable oil is combined in a reaction mixture blend with a stearic acid source material, a butyric acid source material and a caproic acid source material. The reaction mixture blend preferably contains from about 3 to about 40 percent of the liquid vegetable oil, from about 30 to about 80 weight percent of the stearic acid source, from about 5 to about 25 weight percent of the butyric acid source and from about 3 to about 15 weight percent of the caproic acid source. The stearic acid source material is preferably stearic acid which is at least 94 percent by weight stearic acid, and less than 6 weight percent palmitic and other acids. However, stearic acid esters of low molecular weight monohydric alcohols such as methyl stearate and ethyl stearate may also be utilized. The stearic acid source material may include minor amounts (e.g., 0-10 weight percent) of unsaturated $C_{18}$ fatty acids or esters, and/or saturated or unsaturated $C_{20}$-$C_{22}$ fatty acids or esters.

For cocurrent or batch reactions, the stearic acid, butyric acid and caproic acid components are combined with the vegetable oil in one or more reaction stages to provide a transesterification mixture which may vary in composition depending upon the end product desired, the number of transesterification stages to be utilized, and the degree of equilibrium to be achieved in the transesterification mixture. In general, for both reactions, the weight ratio of stearic acid to triglyceride in the initial transesterification mixture should be at least about 0.6:1, and preferably at least 2:1; the weight ratio of butyric acid should be at least about 0.1:1, preferably 0.3:1; and the weight ratio of caproic acid should be at least about 0.1:1, preferably 0.2:1. A weight ratio of 4.75 parts stearic acid, 0.35 parts butyric acid and 0.22 parts caproic acid to 1 part soybean oil in a solvent such as hexane is particularly preferred in a single step process. The fatty acids and the triglyceride are desirably dissolved in hexane or other suitable solvent in a weight ratio in the range of from about 0.5 to about 2.0, solvent to combined fatty acids plus triglyceride vegetable oil, such as soybean oil.

EXAMPLE

Soybean oil (SBO) was converted into a butterfat substitute lipid composition product which has a similar solid fat index/melting temperature profile to that of butterfat, and a smooth organoleptic characteristic. This was done by interesterifying soybean oil with stearic acid, butyric acid and caproic acid in a one step process, using a *Mucor miehei* immobilized lipase, which is 1-, 3-positionally specific, supplied by NOVO Laboratories, Inc., such as described in European Patent 0140542.

The fatty acid composition of the five major fatty acids of the starting soybean oil was as follows:

TABLE 1

| | |
|---|---|
| Palmitic (P) | 10.3 |
| Stearic (S) | 4.2 |
| Oleic (O) | 23.9 |
| Linoleic (L) | 52.3 |
| Linolenic (Ln) | 6.9 |

In a one step reaction, 95 grams of a commercial stearic acid product, 7 grams of a commercial butyric acid product and 4.5 grams of a commercial caproic acid product were mixed with 20 grams of the liquid soybean oil calculated to give a reaction product having final theoretical stearic acid concentration of about 45 weight percent.

The reaction was carried out in a hexane solvent system and utilized 0.175 grams of Novo lipase (containing 3.0-11.0 weight percent of water) per gram of total reactants. The reaction mixture was incubated at 40° C. in a stirred reaction vessel at 250 rpm for a period long enough to assure complete mixing (18-24 hours). To stop the reaction, the lipase was removed via filtration and the hexane solvent distilled off. The free fatty acids were removed by distillation at less than 1.0 Mm Hg at a temperature of 500° F.

The following table shows the Fatty Acid Distribution (FAD) in weight percent of two trial products and the Solid Fat Index (SFI) of one trial product after hexane fractionation compared to butterfat:

TABLE 2

| | FAD, % | |
|---|---|---|
| | Trial #1 | Trial #2 |
| Butyric acid | 1.8 | 3.9 |
| Caproic acid | 1.6 | 2.6 |
| Palmitic Acid (P) | 4.6 | 2.1 |
| Stearic Acid (S) | 40.9 | 45.7 |
| Oleic Acid (O) | 12.4 | 11.0 |
| Linoleic Acid (L) | 33.4 | 30.7 |
| Linolenic Acid (Ln) | 3.1 | 3.5 |

| | SFI | |
|---|---|---|
| °C. | Trial #1 | Butterfat |
| 10.0 | 27.0 | 31.8 |
| 21.1 | 17.3 | 12.6 |
| 26.7 | 6.7 | 8.9 |
| 33.3 | 5.9 | 2.8 |
| 37.8 | 4.9* | <0.1 |

*Some tristearin formed during deodorization

Generally in accordance with another aspect of the present invention, methods are provided for manufacturing a triglyceride oil having less than 3.5 and preferably less than 3 weight percent of esterified saturated fatty acid, and desirably less than 2, and more preferably less than 1 weight percent of intermediate chain length esterified saturated fatty acid.

Various aspects of the present invention are also directed to low saturate liquid vegetable oil products having less than 3.5 weight percent, and preferably less than 3 weight percent saturated fatty acid moieties, and specific unsaturated fatty acid distribution, which liquid vegetable oil products have desirable properties for use in food products such as mayonnaise, margarine, table spreads or salad dressings. Such low saturate vegetable oil products will also desirably have less than about 2 and preferably less than 1 weight percent of intermediate chain saturated fatty acids. By "intermediate chain saturated fatty acid" is meant lauric, myristic and palmitic acids having carbon chain lengths of $C_{12}$, $C_{14}$ and $C_{16}$, respectively. As used herein, the weight percent of saturated or unsaturated fatty acid moieties in a margarine oil or vegetable oil glyceride composition is calculated based on the total weight of the fatty acids contained in the margarine oil. Also, as used herein, when referring to weight percent of one or more fatty acid moieties of a composition (such as the weight percentage of $C_{12}$–$C_{16}$ fatty acids), the weight percent is calculated based on all of the fatty acids of the composition being fully hydrolyzed to free fatty acid. The weight percent of one or more species of fatty acid is then calculated as the weight percent of such one or more species based on the total weight of free fatty acids. AOCS official method Ce 1-62 (81) may be used to determine the weight percent of respective fatty acids of an oil or fat composition.

In accordance with an embodiment of certain method aspects of the present invention, a high-unsaturate vegetable oil, such as canola (low erucic acid rapeseed) oil, high oleic safflower oil, high oleic sunflower oil, high linoleic safflower oil, high linoleic sunflower, soybean oil or mixtures thereof, having from about 4 weight percent to about 15, and typically from about 5 to about 7 weight percent of saturated fatty acids with respect to the total fatty acid content of the vegetable oil is provided for transesterification reaction. Canola oil is a particularly desirable starting material because it has a relatively low saturated fatty acid content. The vegetable oil should best be refined and bleached oil which is substantially free of proteinaceous and other nonglyceride components which might poison or otherwise interfere with transesterification enzymes. In addition to vegetable oils, animal fats, such as tallow, lard and butterfat may be used.

Canola oil typically comprises in the range of from about 5 to about 7 weight percent of saturated fatty acid moieties. However, the saturated fatty acids of canola oil (and other vegetable oils) is not randomly distributed with respect to the 1-, 2- and 3- positions of the glyceride molecules of the oil. A major portion of the saturated fatty acid content is located in the 1- and 3- primary positions of the glyceride molecules of the canola oil. In this regard, canola oil typically may have an overall stearic acid content of about 1.5–2 weight percent based on the total fatty acid content of the oil, with from about 2 to about 3 weight percent of the fatty acid moieties in the 1- and 3- positions being stearic acid and less than about 1 weight percent of the fatty acids in the secondary 2- position being -stearic acid. Similarly, canola oil may typically have an overall palmitic acid content of about 4 weight percent, with about 6 weight percent of the fatty acid groups in the 1- and 3- positions being palmitic acid and less than about 1 weight percent of the fatty acid groups in the 2- position being palmitic acid.

In accordance with certain aspects of the present methods, the saturated fatty acids of the primary 1- and 3- positions are selectively removed, and replaced with unsaturated fatty acids by selective transesterification reaction. This may be accomplished without substantially affecting the fatty acid distribution of the starting material oil in the 2- position. By "transesterification" is meant an exchange of fatty acid moiety or acyl radical at a glyceride oxygen or hydroxyl group, which includes interesterification and intraesterification.

In order to carry out such methods, the high unsaturate vegetable oil such as canola oil is combined with an unsaturated fatty acid transesterification component selected from the group consisting of free fatty acids, fatty acid monoesters of lower alkyl monohydric alcohols (e.g., methanol, ethanol and propanol), and mixtures thereof, which has less than 2 weight percent, and preferably less than 1 weight percent of saturated fatty acids to provide a transesterification blend. The unsaturated fatty acid transesterification component should comprise at least about 98 weight percent of unsaturated fatty acids having a chain length of from 12 to about 22 carbon atoms, and less than 2 weight percent of saturated fatty acids having a carbon chain length in the range of from 12 to 18 carbon atoms based on the total fatty acid content of the transesterification component. Desirably, the fatty acid transesterification component comprises less than 0.75 weight percent and preferably less than 0.5 weight percent of intermediate chain saturated fatty acids, by weight, based on the fatty acid content of the transesterification component.

The high-unsaturate vegetable oil such as canola oil and the unsaturated fatty acid are combined in a weight ratio of vegetable oil to unsaturated fatty acid transesterification component in the range of from about 1:10 to about 4:1 in batch reaction processes (which may utilize multiple reaction steps), and typically in the range of from about 1:2 to about 2:1 in single stage batch or cocurrent reactions to provide a transesterification mixture. The ratio of reactants may be selected to provide a desired degree of substitution under the reaction conditions, to provide a low-saturate glyceride product having a selective level of saturated fatty acid content below about 3.5 weight percent, and preferably below 3 weight percent. Moreover, the ratio of reactants and the composition of the unsaturated fatty acid transesterification component may be selected to provide specific compositions of the transesterified low saturate oil, in terms of unsaturated fatty acid composition. For example, nutritionally desirable unsaturated fatty acids in appropriate levels and ratios have been identified such that an increase in the omega-3 to omega-6 ratio in the average diet could yield distinct health benefits. Natural triglycerides do not typically contain these unsaturated acids in such proportions, but such compositions may be provided in accordance with the present invention. Further in accordance with methods of the present invention, the transesterification mixture is contacted with a transesterification enzyme, which is desirably a 1-, 3-specific transesterification enzyme such as an immobilized lipase from *Mucor miehei* as described in U.S. Pat. No. 4,798,793 issued Jan. 17, 1989, which is incorporated by reference herein. Alternatively, a non-immobilized powdered or granular lipase or cross-linked whole cell lipase containing preparation, as previously described, may be used. The transesterification mixture is contacted with the immobilized enzyme under time and temperature conditions for substantially equilibrating the fatty acid content in the 1- and 3- positions of the glyceride component, with the fatty acid transesterification components of the reaction mixture. The enzymatic transesterification reaction produces a transesterified triglyceride component and a transesterified fatty acid component. The reaction time may range from about 0.5 hour to about 100 hours, depending upon the concentration and activity of the lipase and the temperature of the reaction mixture. For a continuous flow reactor, e.g., a packed bed reactor, a weight hourly space velocity ("WHSV") of oil of 5 inverse hours can be used. The reactant blend contains 0.01 to 5% water. Said water may be added to the reactant blend by passing the blend through a bed of water-containing adsorbent, e.g., resin IRC 900, or by emulsifying the water into the oil blend in a mechanical mixed vessel. The transesterification reaction will desirably be carried out at a temperature in the range of from about 20° C. to about 80° C., and more preferably in the range of from about 40° C. to about 70° C. By "substantially equilibrate" is meant that the transesterification reaction is at least about 50 percent complete, and preferably at least 90 percent complete. Lower equilibrium transesterification conditions (e.g., 50–90 percent equilibrated) may be utilized to increase the reaction speed and or reduce the amount of enzyme used, but this increases the unsaturated fatty acid required and increases the separation step processing requirements.

Following enzymatic transesterification, a transesterified fatty acid component may be separated from the transesterified glyceride component of the transesterification mixture. The transesterified glyceride component has less than 3 weight percent esterified saturated fatty acid content, based on the total weight of the glyceride. Depending upon the ratio of initial components and the extent of transesterification reaction, the transesterified glyceride component will comprise less than 3.5 weight percent of saturated fatty acids based on the total weight of fatty acids in the transesterified glyceride component, and may preferably have less than 3 weight percent of esterified saturated fatty acids, and for specific uses may desirably comprise less than two weight percent of saturated fatty acids.

Further, in accordance with the present invention, the transesterified fatty acid component separated from the transesterification mixture is fractionated to separate the unsaturated fatty acids from saturated fatty acids, to provide a recycle unsaturated fatty acid source material comprising less than 2 weight percent and preferably less than 1 weight percent of saturated fatty acids, based on the total weight of fatty acids in the source material. The recycle fatty acid source material is combined in a recyclic manner with the high unsaturate vegetable oil such as canola oil as an unsaturated fatty acid transesterification component, as previously described, to produce low-saturate triglyceride oils in accordance with the present invention. The recyclic use of the unsaturated fatty acid components is important to the economics of the process.

The fractionation of saturated fatty acids from the fatty acid mixture to provide such a low level of saturated fatty acid content is a difficult fractionation step and may be carried out by a variety of procedures, such as vacuum distillation, selective urea adduction, membrane fractionation (e.g., using zeolitic membranes) and/or selective adsorption chromatography. The saturated fatty acids are difficult to remove from unsaturated fatty acids at low concentration levels. Solvent crystallization at low temperatures may be used to remove at least a portion of the saturated fatty acid content, although typically such solvent crystallization procedures do not reduce the saturated fatty acid content to levels below about 2-3 weight percent of the fatty acid mixture. However, such solvent crystallization fractionation procedures may be used to reduce the saturated fatty acid content for subsequent procedures such as molecular distillation, membrane fractionation (e.g., using zeolitic membranes), urea adduction or other selective absorption fractionation procedures. It is important that the technique utilized ultimately provide a separation such that an unsaturated fatty acid recycle component having less than 2 weight percent by weight, based on the total weight of the fatty acids of the recycle component, and preferably less than 1 weight percent, is provided for recyclic transesterification use. Desirably, at least about 90 weight percent of the unsaturated fatty acid component from the transesterification reaction will be recovered for recyclic use.

In accordance with the present methods, enzymatic transesterification is utilized to reduce the level of saturated fatty acids in a triglyceride vegetable oil by the addition of unsaturated fatty acids in a ratio (oil:fatty acid) such that at substantial equilibrium among the exchangeable fatty acids, the percentage of unsaturates on the glyceride backbone is reduced from that of the starting material. By selectively choosing the unsaturated fatty acids used for transesterification, the enzymatic transesterification reaction may be driven to a desired targeted fatty acid composition in accordance with the present invention.

In accordance with such methods, enzymatic transesterification processes may produce oils with less than 3.5 weight percent of saturated fatty acids and preferably less than 3 weight percent saturated fatty acids, based on the total fatty acid content. For example, by using an immobilized *Mucor miehei* lipase and canola oil, high oleic sunflower oil or high oleic safflower oil, respectively, as the respective starting feedstocks, interesterified oils having reduced levels of saturated fatty acid contents of 1.6%, 1.0% and 0.9%, respectively, may be readily provided. Moreover, such low saturate products may be provided having a substantially 1:1 ratio of monounsaturates to polyunsaturates. Such starting feedstock materials may also readily be converted to oils having a 2:1:1 weight ratio of omega-9:omega-6:omega-3 unsaturated fatty acid content. For example, canola oil may also be readily interesterified to produce an oil with a 2:1:1 weight ratio of omega-9:omega-6:omega-3 esterified unsaturated fatty acids, and a saturated fatty acid content of 2.1%. In order to provide economical manufacturing methods, the free fatty acids which are used to drive the reaction are recycled by separation of saturated fatty acids from unsaturated fatty acids. Separation of triglycerides from free fatty acids and/or separation of oleic, linoleic and linolenic acids from each other may also be utilized in specific embodiments of such methods.

As previously discussed, the saturated fatty acid distribution of vegetable oils such as canola oil is non-random, and is predominantly distributed at the 1-, 3-positions of the vegetable oil glycerides. Accordingly, by utilizing a 1-, 3- specific lipase such as previously described, the transesterification reaction may be limited to the 1-, 3- positions containing the predominant amount of saturated acids in the vegetable oil, without substantially affecting (or having a substantially reduced effect on) the fatty acids at the 2- position. In this manner, the amount of unsaturated fatty acid component utilized to achieve saturate reduction is decreased and effective transesterification efficiency is increased.

While 1-, 3- specific lipases are preferred for use with oils such as canola oil in which the saturated fatty acids are concentrated in the 1- and 3- positions, other lipases may also be used, particularly in oils which do not significantly concentrate saturated fatty acids in the 1-, 3- positions or which nevertheless have excessive saturated fatty acid amounts at every glyceride position. For example, it may be more economical to use a non-specific lipase, such as the lipase from *Candida rugosa* to enable the reduction of stoichiometric amounts of free fatty acids in oils in which all three positions on the triglyceride will desirably be available for exchange. Having generally described various aspects of the present invention, the invention will be more particularly described with the specific embodiment of FIG. 5.

Figure 5:
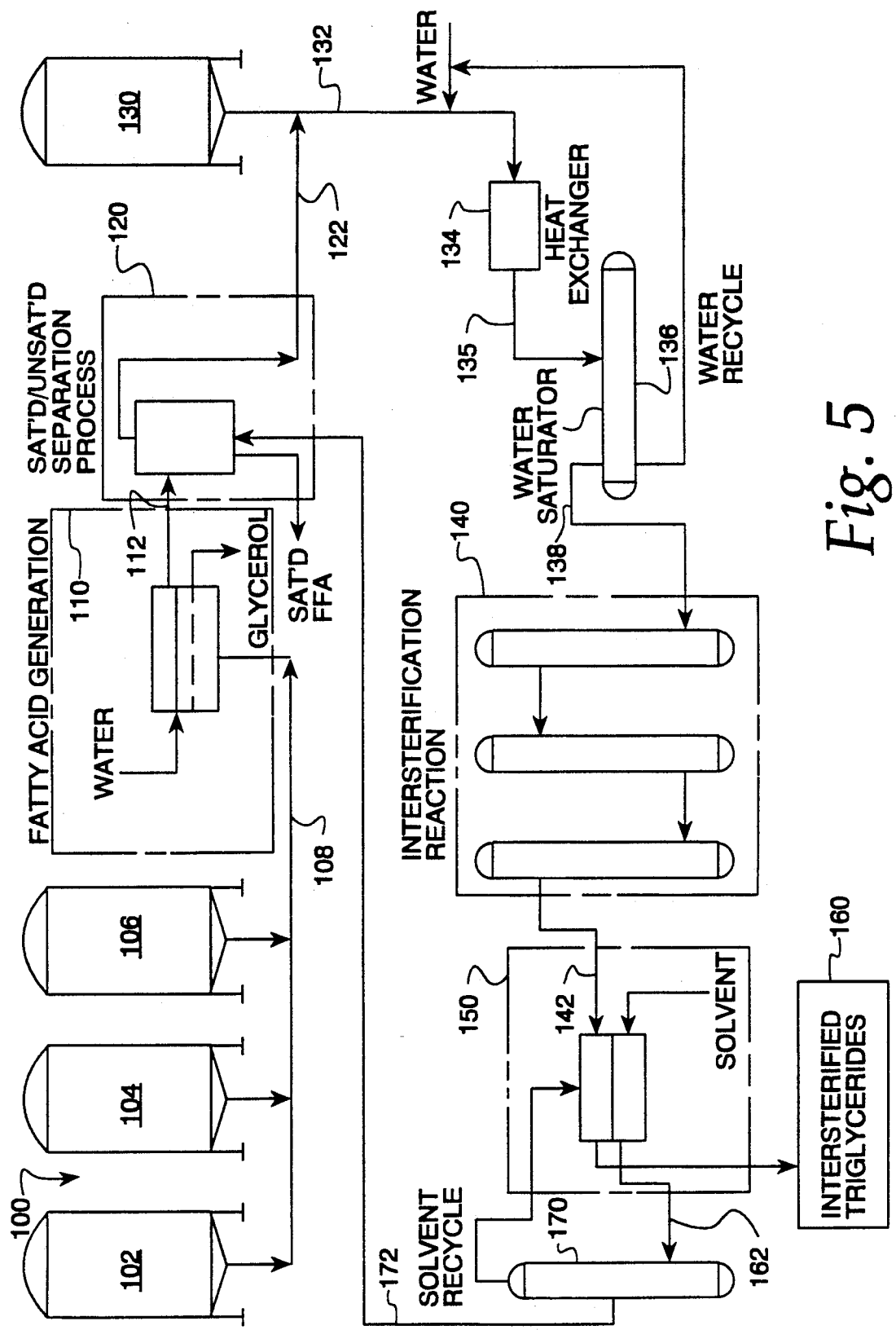
FIG. 5 is a process flow diagram for an embodiment of a single step batch, continuous flow or cocurrent continuous enzymatic transesterification reaction method for producing a low saturate triglyceride in accordance with the present invention having less than 3 weight percent esterified saturated fatty acids.

Illustrated in FIG. 5 is a schematic diagram of a system 100 for producing edible low saturate triglyceride oils in accordance with the present invention. As shown in FIG. 5, a variety of triglycerides may serve as fatty acid source materials for various unsaturated fatty acids, to produce a desired end product. In this regard, the system 100 comprises a canola oil storage vessel 102 to provide a source high in linolenic acid, a sunflower, safflower, corn or soybean oil storage vessel 104 to provide a source high in linoleic acid, and a high oleic sunflower, high oleic safflower or olive oil storage vessel 106 to provide a source high in oleic acid.

Depending on the desired fatty acid content for the transesterification product, one or more of these high linolenic, high linoleic or high oleic source triglycerides is conducted through a conduit 108 to a hydrolysis reactor such as membrane reactor 110 for hydrolysis of the fatty acids of the oil. The reactor 110 may utilize basic hydrolysis catalysts such as sodium hydroxide, sodium methoxide or an immobilized non-specific lipase to fully hydrolyze the triglyceride source material, or may utilize an immobilized unsaturated fatty acid-specific lipase, as previously described, to hydrolyze substantially only the unsaturated fatty acid components of the source triglyceride. Different enzymes may have different specificities toward different fatty acid, thus allowing production of substantially pure fatty acids.

The fatty acid components, which may include saturated fatty acid components from the source triglyceride, are separated from the glycerol component and conducted to a saturated fatty acid separator 120. The fatty acid separator 120 may utilize any appropriate separation technology, and, for example may be a separator such as a low temperature molecular distillation column, a urea adduction separator, ["Fatty Acids, Their Chemistry, Properties, Production and Uses", Part 3, K. S. Markley, Ed., Interscience Publishers, 1964], membrane separation (e.g., zeolitic membranes), which is suitable for separating substantially all of the saturated fatty acids from the unsaturated fatty acid components. The fatty acids may be separated in a pretreatment step by low temperature solvent crystallization procedures to remove a substantial portion of the saturated fatty acid content prior to introduction into the separator 120, in order to reduce the cost of the separation step, if desired.

The separation step performed by the separator 120 is an important step in the method and, as will be described in more detail hereinafter, is also used to process recycled fatty acids and optionally diglycerides produced by the transesterification reaction. An unsaturated fatty acid transesterification mixture 122 comprising less than about 2 weight percent of saturated fatty acids, and preferably less than about 1 weight percent fatty acids is produced by the separator 120. A saturated fatty acid stream 118 is discharged from the separator, and may be utilized for other purposes such as the preparation of hard fats, soaps or chemical synthesis.

In the illustrated embodiment 100, the unsaturated transesterification fatty acid mixture 122 is combined with refined canola oil from storage vessel 130. The canola oil may typically have a saturated fatty acid content which is concentrated in the 1-, 3- position, as shown in the following table:

| Typical Fatty Acid Distribution of Canola Oil & Fatty Acid Feedstocks | | | |
|---|---|---|---|
| | Canola Oil Glyceride Position | | |
| | Overall | 1 + 3 | 2 |
| Palmitic | 4.15 | 6.06 | 0.34 |
| Stearic | 1.81 | 2.72 | less than 0.1 |
| Oleic | 56.74 | 59.64 | 50.96 |
| Linoleic | 19.97 | 13.42 | 33.09 |
| Linolenic | 7.85 | 3.96 | 15.64 |
| Other | 9.48 | 14.20 | less than 0.1 |

The unsaturated fatty acid and canola oil are combined in a weight ratio in the range of from about 0.4 to about 3 of fatty acid to canola oil, to provide a canola oil—fatty acid transesterification reaction mixture 132 which is saturated or supersaturated with water by heat exchanger 134, and water saturator 136, as shown in FIG. 5. The heat exchanger 134 heats the mixture 132 of canola oil and unsaturated fatty acids to approximately the desired reaction temperature of the transesterification reaction, which will preferably be in the range of from about 40° C. to about 70° C.

The heated transesterification mixture 135 is conducted into the water saturator 136, which desirably is a column of anionic resin such as the AmberLite IRA-900 anionic resin product of Rohm and Haas, which is saturated with water. The anionic resin, in addition to rapidly saturating the canola oil-unsaturated fatty acid mixture with water, may also function to remove impurities which may poison or adversely affect the enzyme in the subsequent enzymatic transesterification reaction step. The reaction mixture 138 which is discharged from the water saturator 136 is saturated or supersaturated with water, and in this regard, may typically comprise from about 0.05 to about 0.8 weight percent of water. The mixture 138 may be supersaturated by slightly cooling a water-saturated reaction mixture. The saturation or supersaturation of the mixture 138 with water is necessary to maintain the utility of the resin-bound transesterification enzyme in the transesterification reaction, which will now be described in more detail.

The water-saturated or supersaturated reaction mixture 138 is introduced into an transesterification reactor 140, which in the illustrated embodiment 100 contains an immobilized 1-, 3- positionally specific transesterification lipase immobilized on or within an organopolymeric resin, such as the IM 20 lipase product of Novo Industries, which is an immobilized 1-, 3- positionally specific lipase derived from *Mucor miehei*, as described herein. Alternatively, non-immobilized powdered or granular lipase may be used, as previously described. These lipases are "water-soluble", at the concentrations of water utilized in the interesterification reactor, the enzymes do not dissolve but remain in a porous, granular or powdered state and thus can be practically used in the reactor. For example, *Mucor mehei* lipase (Biocatalysts, Inc.) may be used in a packed bed reactor and approaches equilibrium interesterification at a WHSV of about one. As another alternative, a cross-linked whole cell lipase can be used. A lyophilized preparation of *Rhizopus oryzae* cross-linked with epichlorohydrin also approaches equilibrium interesterification at a WHSV of about one. The fatty acids of the fatty acid source and the fatty acids of the 1-, 3-positions of the canola oil are substantially equilibrated in the reactor 140 to provide an transesterification reaction product mixture 142 which is conducted to a triglyceride/fatty acid membrane separator 150. The mixture 142 generally contains from about 2 to about 8 weight percent of diglycerides produced by the action of the enzyme and water, but may contain up to about 15 weight percent of diglycerides, depending on factors including water content and reaction conditions. As previously described, the formation of peroxides and oxygenated impurities can be suppressed by adding antioxidants such as TBHQ, BHA, BHT and propyl gallate to the feed materials in the respective storage tanks. Further, such peroxide and oxygenated impurities may be removed from the feed stream by utilizing a precolumn of clay, hydroquinone resin or other suitable material. Suppression of peroxide formation and/or removal has been shown to have an extremely beneficial effect on enzyme half-life. The life time of the immobilized lipase system is important in commercial production, and may be monitored by means of an assay system to determine the half-life of the immobilized lipase in the reactor 140. As previously indicated, impurities in both the fatty acids and canola oil may accumulate on the resin and affect the enzymatic activity, and accordingly, pure materials should best be used in the reaction. Said diglycerides may be left in the product triglyceride stream or may be separated. If separated, the diglycerides may be hydrolyzed, either using chemical hydrolysis with steam and alkali metal catalyst, or with non-specific lipase. The fatty acids released by this hydrolysis can be recovered and recycled to the interesterification reactor.

The illustrated triglyceride/fatty acid separator 150 may be a separator apparatus which separates the fatty acid components including those produced in the reaction from the di- and triglyceride components by any appropriate methods, such as by selective absorption fractionation processes, subcritical liquefied gas (e.g., propane) counter-current extraction ["Liquid-Liquid Extraction Employing Solvents in the Region of their Critical Temperatures", Hixson, et al., American Institute of Chemical Engineers, Boston, Mass. meeting May, 1942, pp. 929], water washing, and/or vacuum deodorization, etc. optionally, at least a portion of the diglyceride components may be separated with the fatty acid component if desired by selective adsorption fractionation processes, counter-current selective solvent treatment processes, or other suitable procedures, depending upon desired composition and food product utilization of the transesterified vegetable oil 160.

The transesterified di- and triglyceride product 160 has an esterified saturated fatty acid content of less than 3.5 weight percent, and may be used in a wide variety of food products, such as liquid margarine or cooking oils, mayonnaise and salad dressings, to provide products having extremely low levels of saturated fat. High levels of diglycerides together with very low levels of monoglycerides which may be provided in the process may be particularly desirable in the manufacture of certain emulsified food products containing such low saturate content oils.

The free fatty acids in product stream 162 are separated from the fractionation solvent (if used) by appropriate recovery apparatus 170, which is recycled to separator 150, to provide a recovered fatty acid stream 172 and recovered solvent 174. The recovered fatty acid stream 172 contains saturated fatty acids from the canola oil 130, and from the unsaturated fatty acid stream 122 as a result of the transesterification reaction. This fatty acid recycle stream, as previously indicated, is conducted to the separator 120 for separation of the fatty acid components and removal of saturated fatty acid components to permit recyclic use of the unsaturated fatty acid components. Amounts of saturated fatty acid recovered, and unsaturated fatty acids lost by the separator 120 or in other processing are made up by fatty acids from the source tanks 102, 104, 106 as needed to provide the proper proportion of fatty acid components, in the desired ratio, for the transesterification reaction.

Accordingly, it will be appreciated that low saturated oil may be produced by batch or continuous transesterification reaction methods to produce low-saturate oils with desired fatty acid compositions. Such oils may be selected for fatty acid composition based on the fatty acid composition of the starting oil and the fatty acid composition and relative proportions of the fatty acids used in the reaction.

While the production of low saturated edible vegetable oils using batch, continuous flow or continuous cocurrent reaction has been described, counter-current systems may also be utilized to manufacture such products. Counter-current processes utilizing counter-current supercritical or subcritical fluids which selectively extract and transport the fatty acid may desirably be utilized to provide efficient transesterification of the recycled stearic acid components. Counter-current transesterification procedures may not only provide the reaction efficiencies of counter-current operation, but also may facilitate separation of reaction products.

In supercritical fluids (solvents above their critical temperature and critical pressure) such as supercritical carbon dioxide, hydrocarbons such as ethane and ethane/propane mixtures, and fluorocarbons such as hexafluoroethane, solubility of fatty acid esters such as fatty acid methyl and ethyl esters are typically an inverse function of molecular weight of the fatty acid monoester under various conditions. Similarly, the solubility of fatty acids is inversely proportional to molecular weight of the fatty acid, although fatty acids are typically less soluble in supercritical gases, than corresponding fatty acid lower alkyl monoesters of corresponding molecular weight because of the associative or hydrogen bonding characteristics of the fatty acids.

The respective solubilities of fatty acids, fatty acid esters and triglycerides in carbon dioxide are also a function of temperature and partial pressure of $CO_2$ at relatively low supercritical pressures.

Figure 6:
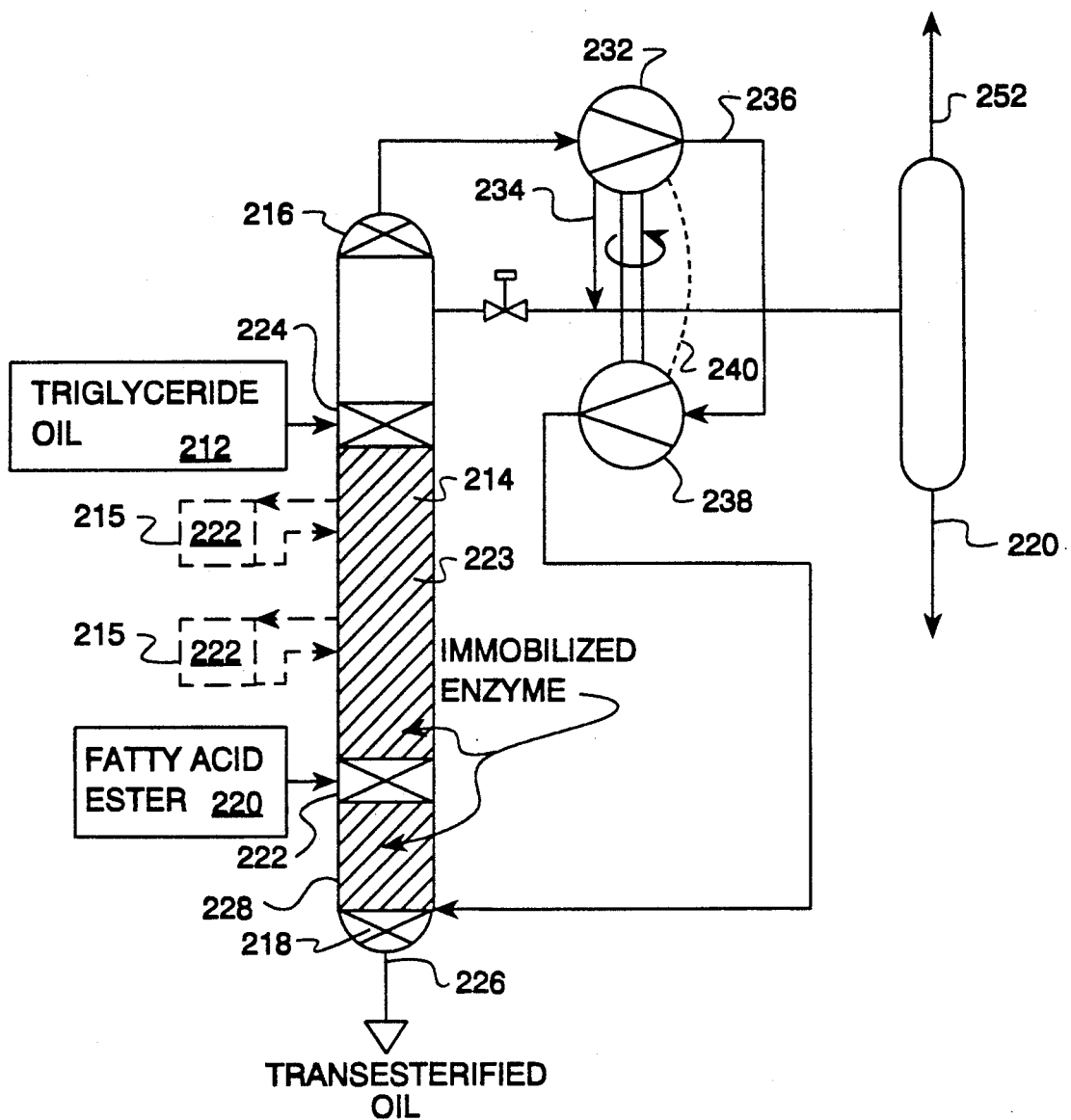
FIG. 6 is a process flow diagram for a continuous counter-current selective enzymatic reaction method utilizing a supercritical counter-current gas stream for producing a low saturate triglyceride oil having less than 3 weight percent of esterified saturated fatty acids.

An embodiment of continuous transesterification process which moves a fatty acid or fatty acid monoester component counter-current to triglyceride flow, and which also removes such fatty acid transesterification reaction components from the transesterified glyceride, is illustrated in FIG. 6.

As shown in FIG. 6, a source of canola oil 212 or other vegetable oil having a low (e.g., preferably less than 10 weight percent, and more preferably less than 7 weight percent) esterified saturated fatty acid content is provided as a starting material.

An unsaturated fatty acid (or fatty acid low alkyl monoester such as a mixture of unsaturated fatty acid methyl or ethyl esters) derived from canola oil having less than 2 weight percent and preferably less than 1 weight percent of saturated fatty acids is provided as a transesterification reactant by selective enzymatic alcoholysis or esterification of unsaturated canola oil fatty acids components. Such methyl or ethyl esters may be provided by appropriate purification procedures such as fractional crystallization, solvent/solvent extraction, membrane separation, urea adduct fractionation, selective absorption fractionation, and/or sub- or supercritical solvent extraction, to separate the unsaturated fatty acid or alcohol ester components from saturated components.

The canola oil 212 may be conducted through a column containing a water-saturated anionic exchange resin to remove non-triglyceride impurities which might poison the enzyme, and condition the oil 212 for the reaction. The rate of introduction corresponds to the transesterification reaction rate permitted by the activity of the immobilized enzyme in the column 214. In this regard, the column is packed with an immobilized lipase enzyme, which is immobilized on an organic or inorganic, high surface area substrate such as porous ceramic rings or pellets, membranes diatomaceous earth organic substrates such as crosslinked ion exchange or phenolic resins (e.g., NOVO IM 20 lipase as described herein) which are insoluble in the supercritical fluid. Alternatively, a non-immobilized powdered microbial lipase or a cross-linked whole cell microbial preparation containing lipase may be used. Alternatively, a non-immobilized powdered plant lipase or a seedling bound lipase, or immobilized or non-immobilized animal lipase may be used. The surface area of the column packing is very large in order to promote interesterification reaction (e.g., more than 750 square meters of surface area per cubic meter), and to promote equilibrium dissolution of the low molecular weight components in the supercritical fluid.

The unsaturated fatty acid (or preferably lower alkyl monoester) component 220 is introduced into a transesterification reactor 214 together with canola oil 212, for transesterification to produce a low saturate triglyceride. An immobilized 1-, 3- specific enzyme 222 such as previously described may be used for transesterification of canola oil, because the saturated acid content of canola oil is concentrated in the 1- and 3- positions. Alternatively, a non-immobilized powdered 1-, 3- specific lipase may be used. An immobilized nonspecific transesterification lipase such as the nonspecific enzyme of *Candida cylindracae* or *Candida rugosa*, may also be used. Moreover, dried lipase-containing microorganism cells and mycelia may also be used as a transesterification enzyme, either retained in the reaction zone, or conducted therethrough with the triglyceride liquid phase flow [e.g., see Gancet, et al., "Catalysis by a Lipase-Bearing Rhizopus Arrhizus Mycelium in (Halogeno)Fluorinated Hydrocarbons", Ann. N.Y. Acad. Sci., Vol. 542, pp. 213–218 (1988)].

The unsaturated fatty acid or preferably a lower alkyl unsaturated fatty acid monoester 220, such as a methyl or ethyl ester of e.g., ethyl oleate, ethyl linoleate, ethyl linolenate mixture, which is desired to be transesterified with the triglyceride 212, which may be saturated with water is introduced into the column 214 at a point 222 between the point 224 of introduction of triglyceride, and the lower outlet 218 at a rate which maximizes the desired transesterification reaction. Because this transesterification reaction is conducted in a counter-current manner, a lower ratio of unsaturated acid esters or acids 220 to canola oil 212 may be used.

In operation, supercritical carbon dioxide (or another supercritical fluid such as an ethane-propane mixture of a fluorocarbon gas having a supercritical temperature for example in the range of from about 30° C. to about 80° C.), is introduced at the bottom of the column 214 under pressure and temperature conditions at which relatively low molecular weight fatty acids or fatty acid esters are significantly dissolved, but at which the high molecular weight triglycerides are relatively not substantially dissolved. For example, carbon dioxide pressures in the range of from about 1,100 psi to about 4,500 (e.g., 2,000–3,000 psi for ethyl esters of oleic, linoleic and linolenic acids), at a reaction temperature in the range of, for example, from about 30° C. to about 70° C., are particularly preferred to provide relatively high fatty acid and/or fatty acid monoester solubility, while providing relatively low triglyceride solubility in the upwardly moving supercritical carbon dioxide stream. The supercritical fluid may contain a small amount of water vapor to maintain the catalyst and to facilitate fatty acid solubility. The temperature, of course, cannot exceed the operating temperature of the enzyme, which will be damaged at high temperatures. In this regard, at lower supercritical pressures, the solubility of the fatty esters and triglycerides is higher at lower temperatures. A reaction temperature should be selected (e.g., 35°–55° C.) which maximizes throughput rate for counter-current transport of the fatty acid monoester, and the transesterification reaction rate which is provided by the enzyme to achieve transesterification of the triglyceride and the fatty acid or fatty acid monoester. Fatty acid lower alkyl monoesters are substantially more soluble in the supercritical fluid than the corresponding acids, and accordingly are preferred reactants. The supercritical gas also serves as a diluent of the triglyceride phase to increase the reaction rate. If it is desired to operate the counter-current column at a temperature higher than the lipase enzyme can tolerate, a plurality of enzyme reaction zones 215 may be distributed along the column 214 which may be operated at a lower temperature, with appropriate heating and cooling means for fluid pumped therebetween. In this manner, the transesterification reaction and counter-current gradient functions may be separately maximized.

The supercritical carbon dioxide is less dense than the downwardly moving canola oil stream at pressures and temperatures used in the system of FIG. 6 (e.g., 35°–70° C., 1,500–3,500 psia). However, by increasing the pressure, the supercritical phase may be made more dense, still permitting gravity or centrifugal counter-current separation. The pressure, temperature, column distances and flow rates of fatty acid or fatty acid monoester and carbon dioxide are selected so that in the zone 228 between the point of introduction of the carbon dioxide and the point 222 of introduction of the unsaturated fatty acid or monoester, the fatty acid or fatty acid monoester is progressively dissolved from the triglyceride into the upwardly moving supercritical $CO_2$ stream; the acid and fatty acid monoester components (including the transesterified components) are substantially completely removed from the triglyceride stream 226 before it is discharged from the column at outlet 218. In this regard, the weight ratio of the flow rate of the carbon dioxide to the flow rate of the unsaturated acid or monoester component 220 introduced in the column 214 may desirably be selected to be in the range of from about 5:1 to about 50:1, under conditions to maximize solubility of the fatty acid or preferably fatty acid monoester component while minimizing the solubility of the triglyceride component phase. In the zone 223, during the time of transit of the canola oil (e.g., 0.25–6 hours), the unsaturated acid component 220 undergoes transesterification with the triglyceride component. Because the flow of triglyceride, and acid or monoester is cocurrent in this stripping zone, the enzymatic transesterification reaction will tend to approach the equilibrium condition of the unsaturated acid monoester-triglyceride blend at the point 222 of introduction of the monoester 220. Accordingly, the composition of the fatty acid or fatty acid monoester which enters the counter-current transesterification zone 223 from the monoester stripping zone 228 will be different from the composition of the fatty acid or monoester 220 introduced into the column 214 at least in part because of the transesterification which occurs in the stripping zone 228. The transesterified triglyceride product, which may have substantially all fatty acid and fatty acid monoester components removed therefrom, is withdrawn from outlet 218.

The ratio of triglyceride components to the unsaturated acid or monoester component 220 to achieve a desired degree of transesterification of the canola oil triglyceride is substantially greater in the system of FIG. 6 than the ratio of triglyceride to fatty acid or monoester utilized to achieve an equivalent degree of transesterification in a one or two step batch reaction. In this regard, the unsaturated acid or monoester 220 is introduced into the bottom of the column at a rate compared to the rate of introduction of canola oil which may, for example, be about half the proportion used in a batch reaction (e.g., 1:3 to 1:1 weight ratio of unsaturated acid component to canola oil).

The fatty acid or monoester component is dissolved in the upwardly moving supercritical $CO_2$ gas stream and carried into the transesterification zone 223, where it approaches equilibrium with the counter-current oil flow through the action of the immobilized enzyme in the column. It is further transesterified in a counter-current manner with the liquid triglyceride stream as it is conducted from its point of introduction 224 to the point 220 of introduction of the fatty acid monoester.

The triglyceride phase mixture continuously undergoes transesterification reaction as it moves downwardly in the zone 223 containing lipase enzyme counter-current to the flow of supercritical gas, such that the mixture has an increasing concentration of the desired triglyceride components as it moves down the column. There is also an increasing concentration of transesterified fatty acid or monoester having fatty acid or monoester components derived from the triglyceride in the upwardly moving supercritical gas stream, in the direction toward the point of introduction of the triglyceride. Water vapor may be included in the carbon dioxide flow, the fatty acid ester flow and/or the triglyceride flow to accommodate the transesterification reaction, which may exceed the solubility of water in the triglyceride component, and to produce a desired level of diglycerides, if desired. Fatty acid components produced by hydrolysis reactions in the column 214 may also be removed by the supercritical carbon dioxide flow.

The transesterified fatty monoester or fatty acids dissolved in the supercritical $CO_2$ gas stream is carried from the column at outlet 216, through a pressure letdown system, where dissolved fatty acids or monoesters are taken out of supercritical solution as a result of pressure reduction. The tank 232 may alternatively be heated to further reduce the solubility of the fatty acid monoester. The solubility reduction may also be accomplished by a combination of a limited pressure reduction (e.g., by 500–1,000 psi) and a temperature increase (e.g., to 70°–100° C.) so that the work to recompress the $CO_2$ for recycle use may be reduced. The energy recovery system may comprise a piston or turbine engine 232 in which the dissolved fatty acid or monoester 234 are collected in the recovery system, so that the energy may be recovered for recompression of the carbon dioxide upon recyclic operation. The lower pressure $CO_2$, which is depleted in or free of dissolved fatty acids or monoesters, is recompressed by compressor 238.

The carbon dioxide 236 which is separated from the fatty acid or monoester is conducted to compressor/thermal conditioner 238 where it is recompressed and reintroduced at the preselected operating temperature as previously discussed. A heat-pump or other thermal connector 240 may be used to transfer heat between the compressor 238 and the decompression engine 232. A portion of the extracted fatty acid components 234 may be recycled for reflux purposes to increase selectivity. The flow rate of supercritical carbon dioxide (or other supercritical gas solvent) through the column 214 is correlated with the flow rate of fatty acid ester 220 so that it is adequate to transport and dissolve substantially all of the fatty acid monoester under the operating conditions, but dissolves a minimal amount of the initial canola oil and other triglyceride components. The solubility of the fatty acid or fatty monoester components will desirably be greater than 1 weight percent, and preferably greater than 2 weight percent, while the solubility of triglycerides will be less than 0.5 weight percent and preferably dissolved triglycerides will be less than 10 percent of the dissolved fatty acid or monoester in the extracted product 234.

The separated fatty acid or monoester 234 may be purified in fractionation system 250 to separate purified unsaturated fatty acids 220 from other materials 252 in any suitable manner, and the unsaturated transesterification component 220 may be recycled for transesterification use.

Figure 7:
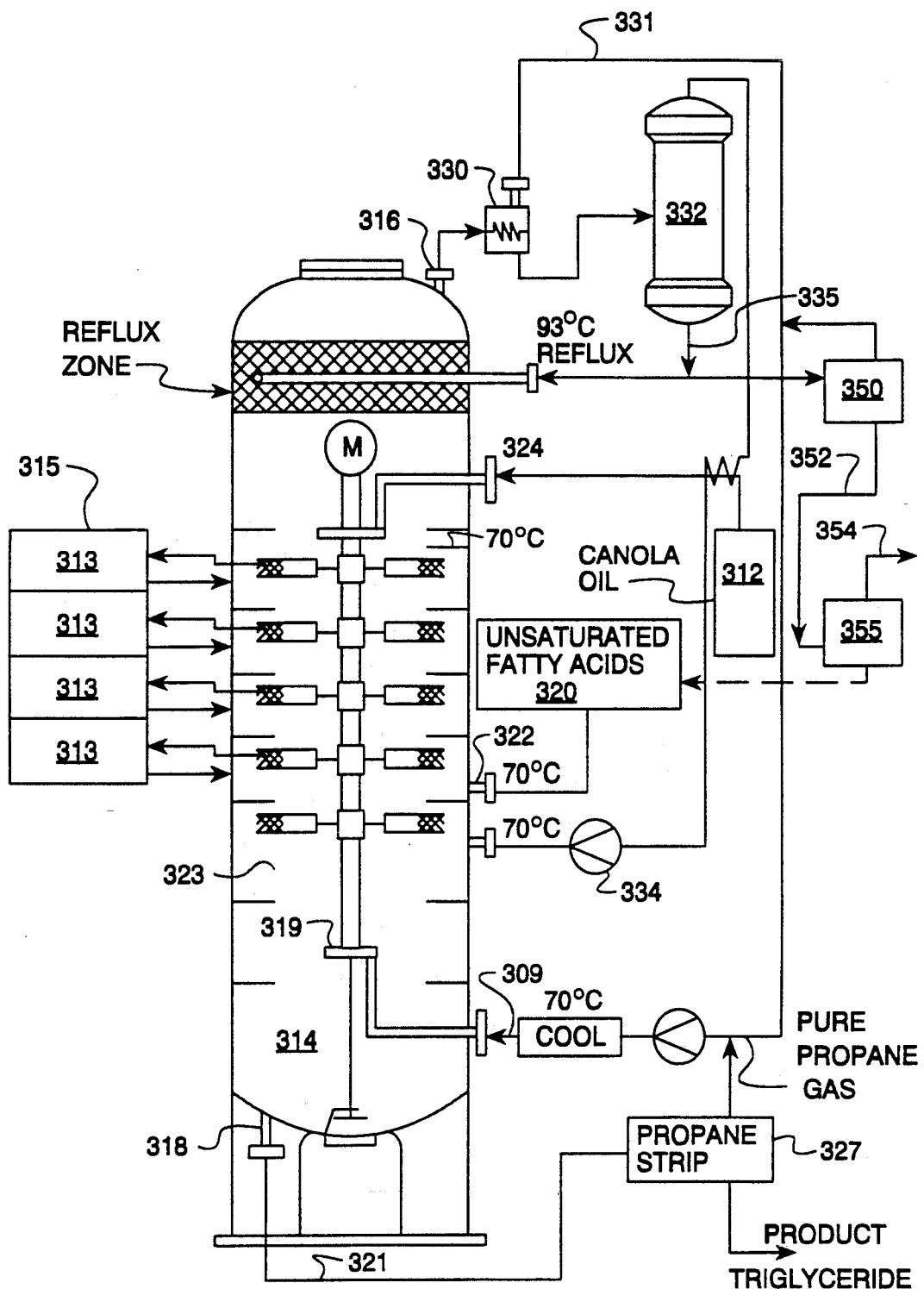
FIG. 7 is a process flow diagram for another method of preparing a low-saturate edible oil by counter-current enzymatic transesterification reaction, utilizing a counter-current subcritical gas.

Another embodiment of a continuous counter-current transesterification process is illustrated in FIG. 7, which moves a fatty acid or fatty acid monoester component counter-current to triglyceride flow, utilizing a subcritical liquified gas solvent. As shown in FIG. 7, the vegetable canola oil 312 to be transesterified is introduced into a high pressure column 314 at a point 324 intermediate the upper outlet 316 and the lower outlet 318. The rate of introduction corresponds to the transesterification reaction rate permitted by the activity of the immobilized enzyme in the column 314. The column may be packed with an immobilized lipase enzyme as previously described, which is immobilized on an inorganic, high surface area substrate such as porous ceramic rings, pellets or membranes, or diatomaceous earth (e.g., Celite), or a suitable organic substrate such as an ion exchange resin substrate (e.g., NOVO IM 20 lipase). Non-immobilized enzymes, as previously described, may also be used. Such packing may be in particulate, film or fiber form, on plates, etc. Alternatively, as shown in FIG. 7, the column 314 may be used to establish concentration gradients and counter-current flow in stages, and the immobilized enzyme 313 may be located in corresponding stages in a separate pressure vessel or vessels 315, particularly where the immobilized enzyme has an upper thermal stability limit which is below the desired 2-phase counter-current operating temperature which provides maximum selectivity. In such systems, the reaction mixture may be cooled before entering the reaction zone and reheated upon exiting the zone 315. The surface area of the column packing should be very large in order to promote transesterification reaction (e.g., more than 750 square meters of surface area per cubic meter), and to promote equilibrium dissolution of the low molecular weight components in the subcritical liquified gas.

A fatty acid or lower alkyl fatty acid monoester 320, such as a methyl or ethyl ester of an unsaturated fatty acid component (e.g., a mixture of unsaturated fatty acids or unsaturated fatty acid esters such as methyl or ethyl esters), which is desired to be transesterified with the triglyceride 312, is introduced into the column 314 at a point 322 intermediate the point 324 of introduction of triglyceride, and the lower outlet 318 at a rate which maximizes the desired transesterification reaction. For manufacture of the low saturated fat vegetable oil, a mixture of unsaturated fatty acids or monoesters comprising less than 2 weight percent of saturated fatty acids is used. The rate of introduction is about 0.25 to 1.0 the rate of vegetable oil input, lower ratios being used for higher purity (e.g., less than 0.5 or 0.25 weight percent saturated fatty acid content). The transesterification reaction is conducted in a counter-current manner, so that it is substantially more efficient than a batch reaction of the fatty acid and triglyceride components at the selected reaction ratios.

In operation, liquified propane 309 is introduced at a position 319 near the bottom of the column 314 under pressure, flow rate and temperature conditions at which relatively low molecular weight fatty acids and monoesters are significantly dissolved, but at which the high molecular weight triglycerides are less soluble and form a separate phase. The temperature, of course, cannot exceed the operating temperature of the enzyme, which will be damaged at high temperatures. In the illustrated embodiment, the propane may be introduced at a pressure of about 600 psi and a temperature of 70° C. at a rate of about 10 times the rate of introduction of fatty acid 320 on a weight ratio basis. If a lower temperature is necessary for use with an enzyme which does not exhibit high temperature stability, fluorocarbon liquefied gases, ethane, methane/propane or ethane/propane mixtures having a lower critical temperature may be used. The liquefied propane gas also dissolves to some extent in the triglyceride phase and serves as a diluent to decrease the viscosity of the reaction mixture.

The liquefied propane phase is less dense than the downwardly moving vegetable oil stream, typically having a density in the range of 0.25-0.4 g/cm$^3$, depending primarily on composition and temperature. The pressure, temperature, column distances and flow rates of fatty acids (or monoesters) and liquid propane are selected so that in the zone 323 between the point 319 of introduction of the pure liquified propane and the point 322 of introduction of the unsaturated fatty acid or monoester 320, the fatty acid or monoester components are progressively dissolved from the triglyceride into the upwardly moving liquid propane phase; the fatty acid or monoester is substantially completely removed from the triglyceride stream 321 before it is discharged from the column at outlet 318. Because of counter-current transesterification which occurs in the transesterification zone, the fatty acids or monoesters in the upwardly rising liquid propane droplets will be different from the composition of the fatty acids 320. The transesterified triglyceride product is withdrawn from outlet 318. It contains an amount of propane which is an inverse function of temperature (e.g., 30–60 weight percent propane), which is removed in propane stripping column 327 and returned for recyclic use.

The ratio of triglyceride component 312 to the unsaturated fatty acid component 320 to achieve a desired degree of transesterification of the triglyceride will be substantially greater in the counter-current system than the ratio of triglyceride to fatty monoester necessary to achieve an equivalent degree of transesterification in a batch or cocurrent reaction, as previously discussed. Moreover, high levels of transesterification substitution may be obtained with the proposed counter-current process, which could otherwise only be achieved with multiple batch reaction, and multiple component separation.

The fatty acid component is dissolved in the upwardly moving propane phase, and is continuously exchanged with the downwardly moving vegetable oil phase, creating a gradient along the column, and carried into the transesterification zone, where it tends toward dynamic equilibrium with the counter-current oil flow. It is transesterified in a counter-current manner with the liquid triglyceride stream as it is conducted from the point of introduction 324 to the point 322 of introduction of the fatty acid monoester.

A portion of the mixture is pumped from mixing stages in the column 314 to transesterification zones 313 containing a suitable transesterification enzyme. The mixture continuously undergoes transesterification reaction in the separate zones 313, and is returned to the respective phase separation zones of the column 314, such that the mixture has an increasing concentration of the desired triglyceride as it moves down the column. It is noted that the columns 314 may be maintained at a higher temperature (e.g., 70°-90° C.) at which phase separation is enhanced, while the lipase reaction zones 313 may be maintained at a lower temperature (e.g., 50°-60° C.) at which the enzyme longevity and reaction are maximized, by appropriate heating and cooling of the streams conducted there between. It is also noted that by cooling the liquid phases which increase mutual solubility (toward and including miscibility), and reheating them, which causes phase separation, extraction efficiency may be increased. Accordingly, there is also an increasing concentration of transesterified fatty acid components derived from the triglyceride in the upwardly moving liquefied gas stream, in the direction toward the point of introduction of the triglyceride. Water vapor may be included in the liquified gas phase flow, the fatty acid flow and/or the triglyceride flow to accommodate the transesterification reaction, and which may equal or exceed the solubility of water in the triglyceride component, if desired, as previously discussed. Any fatty acid components, as well as monoglycerides (and diglycerides) produced by hydrolysis reactions in the column 314 may also be (at least partially) removed by the upwardly moving liquified propane phase (which may be facilitated by a small amount of water or ethanol in the propane phase).

The transesterified fatty acid component which is preferentially dissolved in the upwardly moving liquid propane phase, is carried from the column at outlet 316 at e.g., 70°-85° C., through heater/evaporator 330 where it is heated to 93° C. to evaporate pure propane 331 and then into separation tank 332, where dissolved fatty acid components 335 are taken out of solution as a result of propane evaporation and temperature increase. In this regard, the exiting propane phase is heated to further reduce the solubility of the fatty acid (and any triglycerides), without deactivating the enzyme, which is not present in the tank 332 or the upper reflux portion of the column 314. The liquid propane exiting the column may be heated to 94°-95° C., to create two phases in the separation tank or column 332. Of course, all of the propane may be evaporated to recover the fatty acid components, but this is not necessary, particularly in view of the amount of propane utilized. A portion (e.g., 20-50 weight percent) of the separated fatty acid component may be reintroduced into the top of the column 314 into a reflux zone to enhance the selectivity of the counter-current transesterification reaction component separation. The remaining portion of the fatty acid material 335, which contains 30-60 weight percent propane as well as some di- and triglycerides (and perhaps very small amounts of monoglycerides) in addition to the fatty acid or monoester components, is conducted to a propane stripper 350 and from there the propane-free fatty acid components 352 (which may optionally first be hydrolyzed as previously described) are conducted to an appropriate separation system 352 for separation of the unsaturated fatty acid components in relatively pure form for recycle use. The saturated fatty acid components 354 are separated from the unsaturated fatty acid components in a suitable separator 355. The fatty acids (and any mono, di- and triglycerides) may be further utilized as desired. The unsaturated fatty acid components may be esterified with ethanol and recycled.

The liquid propane which is separated from the fatty acids in the tank 332 is conducted to preheat the canola oil 312 and then to pump/thermal conditioner 334 where it is cooled to 70°-75° C. and reintroduced at the preselected operating temperature. Because it has a very small amount of product fatty acids, it is introduced at an intermediate position in the column 314. A portion of the propane is evaporated at heater/propane boiler 330 and recompressed to produce a pure propane stream for fully stripping the fatty acids and lower molecular weight components upon introduction at the bottom 319 of the reactor 314. The dissolved fatty acid or monoester components may also be separated by heating the propane stream in heater 330 to a temperature above the critical temperature (96°-98° C.) of the propane (e.g., 100°-110° C.) while maintaining the system at a pressure slightly above the critical pressure (42 atmospheres), such as 44-50 atmospheres. In this way, a substantial portion of the components 335 are separated in column 332, and the supercritical propane gas may be reliquefied by cooling to a temperature below the critical temperature for reintroduction into the column 314. Such a substantially isobaric procedure minimizes heat and pumping expense. The flow rate of liquefied gas solvent through the column 314 is correlated with the flow rate of fatty acid ester 320 so that it is adequate to dissolve substantially all of the fatty acid or monoester under the operating conditions and remove it from the transesterified triglyceride 321. While the process of FIG. 7 was described with respect to subcritical liquid propane, other subcritical liquids such as ethane, ethane/propane mixtures, certain low molecular weight fluorocarbons and mixtures thereof having lower critical temperatures may be used in the process to better accommodate lipase enzyme operating temperatures of maximum efficiency and lifetime.

As previously discussed, urea adduction may be utilized to separate saturated fatty acid components from unsaturated fatty acids or monoesters to provide a substantially pure unsaturated fatty acid reaction component. Although urea typically crystallizes in a tetragonal form, it forms complexes with straight chain fatty acids and lower alkyl monoesters in which the straight chain fatty compound is included within a hexagonal crystalline urea framework to form urea inclusion compounds having a weight ratio of approximately 3:1 of urea to the included compound. In general, saturated fatty acids form more stable urea complexes than unsaturated fatty acids of the same carbon chain length. The stability constants decrease by an order of magnitude in the series stearic, oleic and linoleic acids, respectively [Chapter XX Techniques of Separation E. Urea Complexes, p. 2309, et seq., K. S. Markley, Ed., supra]. Saturated monoesters may have greatly increased stability. The stability of fatty acid complexes also increases with the carbon chain length of the fatty acid, and saturated monoesters of lower alkyl alcohols may have enhanced stability.

The urea complexes may be readily decomposed by adding water or other solvent to dissolve the urea, leaving the saturated fatty acid inclusion compounds as an oil or solid, depending upon the temperature of decomposition. A small quantity of an acid such as hydrochloric acid may be utilized to prevent formation of emulsions by traces of ammonia soaps. Conversely, heating the urea complex with a solvent such as hydrocarbon solvent in which the urea is insoluble may also be used to extract the included saturated fatty acid compound.

In order to separate saturated fatty acids (or monoesters) from unsaturated fatty acids (or monoesters), insufficient urea to combine with all the complex forming components of a mixture is added, such that the saturated component will combine with the urea and preferentially precipitate with respect to the less stable unsaturated fatty acid complexes. Utilizing differences in complex-forming capacity, highly purified unsaturated fatty acids may be isolated from various natural sources for use in transesterification processes of the present invention as previously described.

Although urea complexes have the melting point of urea, which is approximately 133° C., urea adducts become less stable with increasing temperatures and decompose at a temperature below the melting point of urea, which is characteristic for a specific complex. The dissociation temperature for stearic acid/urea adduct in the absence of any solvent is about 126° C. The dissociation temperature of the palmitic acid/urea adduct in the absence of any solvent is about 114° C., and the dissociation temperature of the oleic acid/urea compound in the absence of any solvent is about 110° C. These differences may be utilized in refining and separation processes.

The preferential activity of saturated fatty acids to form urea complexes may be used to remove substantially all of the stearic acid, and a substantial portion of the palmitic acid content of a saturated fatty acid stream in a liquid/solid counter-current distribution method of separation. For example, the fatty acids and urea dissolved in appropriate solvent may be provided as a moving liquid phase, while the precipitated reaction products may serve as the stationary solid phase. The character of the distribution curve obtained for a given mixture of fatty acids depends on the differences in the distribution coefficients for the individual acids when they are distributed between solid inclusion compounds and the organic solvent [W. N. Sumerwell, J. Am. Chem. Soc., 79, 3411–3415 (1957)].

Figure 8:
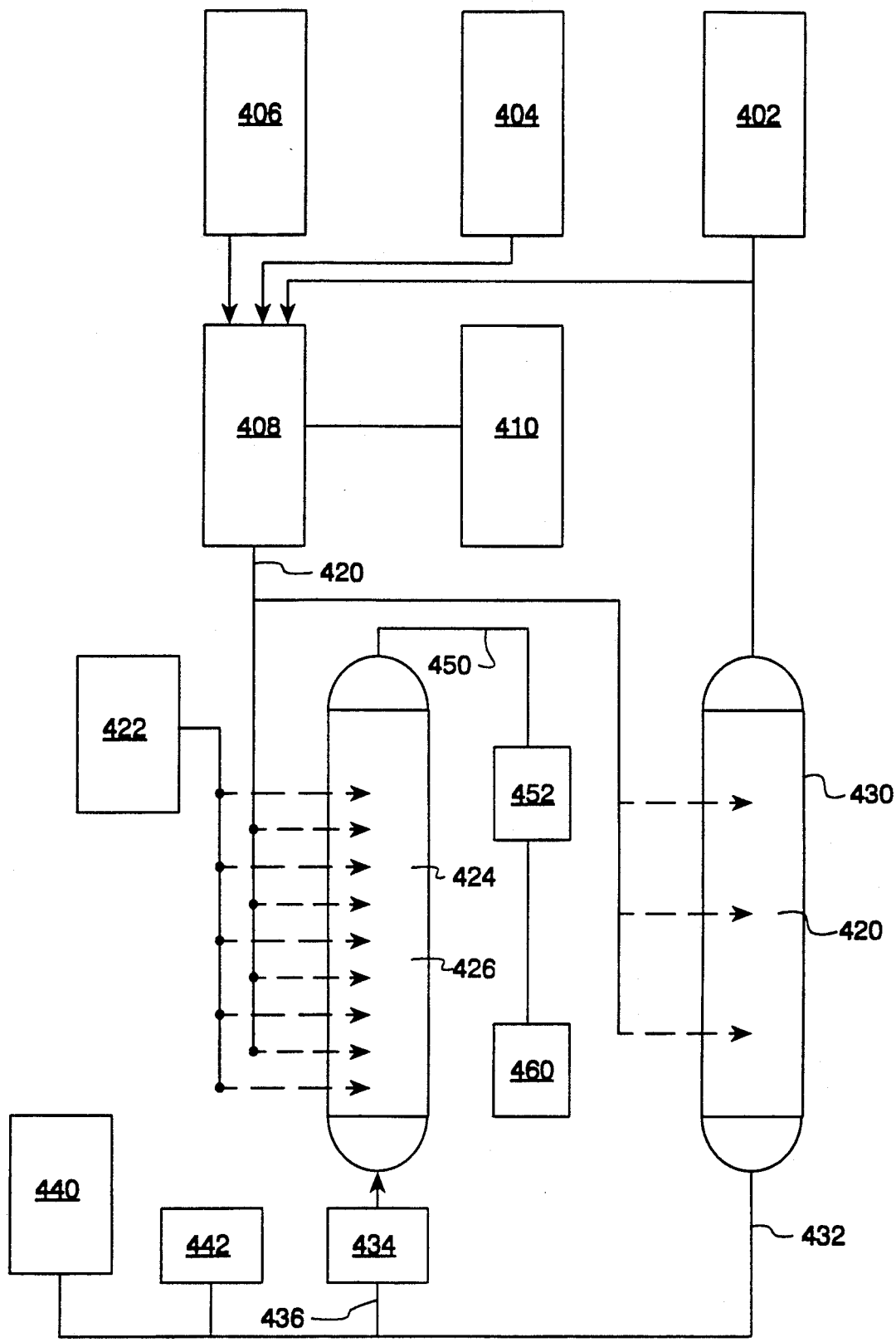
FIG. 8 is a process flow diagram of another embodiment of a transesterification method for transesterifying an unsaturated fatty acid monoester with saturated fatty acid-containing triglyceride vegetable oil to provide a triglyceride oil having very low saturated fatty acid content.

Illustrated in FIG. 8 is a continuous system for economically providing a transesterified low saturate vegetable oil in which the saturated fatty acids are removed by urea/unsaturated fatty acid inclusion reservoir compounds concomitantly with enzymatic acyl transfer reaction. In this regard, an unsaturated fatty acid/urea reservoir complex may be prepared which serves as an exchange reservoir for removal of saturated fatty acids. Such unsaturated exchange reservoir urea inclusion compounds may be prepared in a suitable manner such as shown in FIG. 8 by dissolving canola oil fatty acids or a fatty acid lower alkyl monoesters 402, (e.g., methyl or ethyl esters) in a suitable solvent. Methyl and ethyl esters are preferred because urea adducts of palmitic and stearic monoesters may have substantially higher stability constants than oleic acid or oleic acid monoesters, thereby facilitating saturated component removal.

The exchange reservoir inclusion compound crystals are formed by dissolving the canola fatty acids or monoesters which comprise about 5–8 weight percent palmitic and stearic acids (or monoesters), in a suitable amount of a solvent such as ethanol or methanol 404 (and hexane if necessary), together with about 30–50 weight percent of urea 406, based on the weight of the fatty acids. The solution is cooled in a crystallization vessel 408 to produce a first crop of urea inclusion crystals which comprise about 10–12 weight percent of the fatty acid component. The first crop of urea inclusion crystals are separated as first crop product 410. The first crop urea inclusion crystals are predominantly urea stearate and palmitate compounds, because of the tendency for the saturated fatty acid (or preferably monoester) to form urea inclusion compounds, leaving in solution at least 98–99% pure unsaturated fatty acids or monoesters in the crystallization vessel solution 408. An excess of urea, e.g., a 7:1 or more weight ratio of urea to remaining canola unsaturated fatty acids in the vessel 408, is then added and dissolved at elevated temperature. Upon cooling, a second crop of urea inclusion compounds is formed which are predominantly urea oleate and linoleate inclusion compound crystals, which form an exchange reservoir inclusion compound material 420. These exchange reservoir crystals 420 may be dried to remove solvent and used with an immobilized lipase enzyme 422 such as 1-, 3-specific lipase from *Mucor miehei* immobilized on an ion exchange resin, such as the NOVO IM 20 lipase product of Novo described in U.S. Pat. No. 4,798,793, in a weight ratio of 2:1 to about 10:1 unsaturated fatty acid urea inclusion reservoir crystals to immobilized enzyme/ionic resin component to form the packing 424 of an intraesterification reaction column 426. The reservoir crystals are also placed, without an immobilized lipase component, as the packing into a column 430. The urea reservoir crystals may be blended with, or alternated in layers with the transesterification lipase in column 426. Canola oil fatty acids or preferably lower alkyl monoesters 402 are conducted through the column 430 at a temperature in the range of 20°–110° C., preferably in the range of 40°–60° C.

A temperature selected for maximum relative stability of the palmitic acid complex over the oleic acid complex may be selected if desired to maximize removal of the palmitic acid component. Because the urea complexes of stearic and palmitic acid or preferably monoester components of the mixture 402 have a higher stability than the oleic or linoleic complexes, the stearic and palmitic acids or monoesters exchange with these unsaturated fatty acids to form more stable inclusion compounds, thereby producing an unsaturated fatty acid or monoester stream 432 which is substantially free of saturated fatty acids or monoesters. The unsaturated discharge stream 432 may be blended with refined and bleached canola oil 440 in a weight ratio of from about 30:1 to about 1:1 canola oil to fatty acid component, and preferably in a range of from about 10:1 to about 3:1, to produce a transesterification stream 436. The canola oil transesterification stream 436 may be conducted through a water saturated ionic exchange resin column 434 (e.g., at a temperature of 40°–70° C.) to saturate the oil/fatty acid (or monoester) blend 436 with water and remove impurities which might deactivate the enzyme.

The saturated intraesterification stream 436 accordingly may have a limited amount of fatty acid component and will require reduced separation treatment after transesterification.

A suitable solvent such as butane, pentane, hexane or pressurized propane 442 may be used to reduce the viscosity of the transesterification stream 436 which is introduced into the interesterification column 426. The stream 436 is conducted through the transesterification column 424 where the 1-, 3- fatty acid moieties of the canola oil are progressively released and exchanged with unsaturated fatty acid components of the stream 436 by the acyl transfer activity of the immobilized enzyme. Such unsaturated fatty acid components may be initially present in the stream 436, may be produced by a small amount of hydrolysis from the water content of the stream, or may be derived from the unsaturated fatty acid urea adduct reservoir material 420. In this regard, as the saturated fatty acid moieties are released by the transesterification reaction, they undergo equilibration reaction with the reservoir urea inclusion compound crystals of the packing 424 and are exchanged with the unsaturated fatty acid components of the inclusion crystals. The efficiency of the overall production process is enhanced by close proximity of the enzyme and the inclusion compounds. In this manner, the saturated fatty components of the canola oil are progressively removed as the stream 436 is conducted through the column 426. An increase in diglyceride and fatty acid content will occur as a result of the small water content of the stream 436. When using unsaturated fatty monoesters, a vacuum may be periodically or continuously applied to the column 426 with a slow nitrogen bleed to remove monohydric alcohol, increase the triglyceride content and decrease the diglyceride content of the stream, if desired.

The stream 436 is conducted through the column 426 at a rate, combined with the transesterification rate and inclusion compound exchange rate, which produces an output stream 450 comprising less than 3 weight percent of saturated fatty acid content based on the total weight of the stream. The processing may be continued until the saturated fatty acid exchange capacity of the urea inclusion reservoir component 424 or the component 420 of the column 430 are exhausted. The output stream 450 may be refined in any appropriate manner such as counter-current solvent processing in refiner 452 to remove the fatty acid or monoester and any small amounts of urea. The low saturate triglyceride mixture may alternatively, or subsequently, be deodorized by conventional steam deodorization or supercritical carbon dioxide deodorization to produce a very low saturate vegetable oil product 460.

The urea inclusion reservoir component column packings 420, 424 may be replaced or regenerated periodically. Such replacement and regeneration may be accomplished by redissolving the urea in a hydroxy solvent such as methanol to release and separate the saturated fatty acid inclusion compound, and recycling the urea in solvent-reformed unsaturated fatty acid reservoir crystals. However, it is preferred to regenerate the hexagonal urea compound without dissolving it, using solvent or fatty acid or monoester components which are compatible with and/or easily separable from, the adduct. In this regard, for example, the packing 420 may be regenerated by passing therethrough a stream of a solvent such as hexane, liquified propane and/or unsaturated fatty acids 402 (which preferably may have had the saturated fatty acids removed therefrom) at a temperature sufficient to release the saturated fatty acid inclusion components, which may be up to a temperature above the decomposition temperature of the stearate and palmitate inclusion compounds (e.g., about 126° C.), but below the melting temperature of the urea (133° C.). An output stream high in stearic and palmitic acids is produced, which may be utilized or reprocessed as desired. The thermal stability limit for the enzyme should not be exceeded by such regeneration treatment if the enzyme is mixed or treated with the urea reservoir material. Layering as previously described permits separate regeneration treatment of the reservoir material. After releasing the saturated inclusion compounds from the packing 420 in this manner, it may be cooled in the presence of unsaturated fatty acids compounds, thereby reforming the reservoir material as an unsaturated fatty acid complex. Low molecular weight hydrocarbons such as hexane or petroleum ether, which form relatively unstable inclusion compounds, may be used to extract the saturated fatty acid component in such regeneration, or solvents which do not form an inclusion compound, such as liquified propane may be used. It may be desirable to remove all such solvent following regeneration by methods such as vacuum treatment. Regeneration may be carried out on a continuous counter-current basis with the "spent" inclusion compound packing 424 being continuously or periodically withdrawn from the bottom (counter-current inlet) and regenerated material added at the top transesterified oil outlet.

While described for urea/unsaturated fatty acid adducts, other suitable adsorbent or adduct forming materials may be used which preferentially adsorb saturated fatty acids or monoesters over unsaturated fatty acids or monoesters. For example, X and Y type zeolites and/or silicalite having appropriate pore structures which preferentially absorb saturated fatty acids may be regenerated or "recharged" with purified unsaturated fatty acids or monoesters, and used in admixture with the immobilized enzyme. Counter-current moving bed systems or simulated moving counter-current bed systems may be used to facilitate continuous operation. Other selectively adducting components, such as alpha, beta and gamma cyclodextrins, may also be used to selectively exchange or remove fatty acid components from the reaction mixture.

An additional aspect of the present invention is directed to methods for removing cholesterol from whole egg and egg yolks while minimizing loss of phosphatides, using a liquified subcritical gas such as ethane near its critical temperature and below the denaturation temperature of egg yolk protein. Such methods may be similarly used to remove cholesterol from vegetable oils used as cholesterol extractants, and to provide substantially cholesterol-free or cholesterol-reduced animal fats for use in transesterification, interesterification and esterification processes as described herein.

In accordance with such methods, whole or dried egg yolks may be inexpensively extracted using subcritical ethane or the like to remove cholesterol at temperatures which do not denature the egg yolk protein, and do not extract substantial quantities of phosphatides or phospholipoprotein complexes. The cholesterol treatment may also be carried out to remove triglycerides, to minimize the extraction of natural egg yolk triglycerides, or to substitute unsaturated triglycerides for the natural egg yolk triglycerides. Volatile flavor components may also be recovered from the cholesterol extraction mixture for recombination with the extracted egg yolk by appropriate treatment of the extracted high cholesterol components.

Liquified, normally gaseous hydrocarbons such as ethane, propane, and freons particularly including lower alkyl perfluorocarbons, are soluble in glycerides, free fatty acids, cholesterol and cholesterol esters at temperatures well below the critical temperature. However, as the temperature is increased toward the critical temperature of the liquefied gas, the mutual solubility dramatically decreases. This decrease is a function of the composition and functional groups molecular weight and other factors, so that higher molecular weight fatty materials form a separate phase at lower temperatures than lower molecular weight materials. The density of the compressed normally liquid hydrocarbon phase decreases as the critical temperature is approached, so that density differences after phase separation permit easy gravimetric separation of the liquid fatty material phase from the liquefied gas phase. As the critical temperature is approached, triglycerides become less soluble in the liquified gas and the liquified gas becomes less soluble in the triglyceride. Solubility of fatty materials in liquified propane also decreases with increasing unsaturation, and decreases with increasing numbers of carbon atoms. Egg yolk triglycerides lose miscibility in liquified propane at temperatures of 60°–80° C., as an inverse function of triglyceride molecular weight. This permits retention of a substantial portion of the egg yolk glycerides, which typically constitute about one third of the dry weight of the egg yolk. It also permits maintenance of a separate fatty phase for counter-current operation.

The liquefied propane critical temperature of 96.8° C. is too high for processing of egg yolk proteins at near-critical temperatures without denaturation of the protein, which destroys functional emulsification properties of the egg yolk. However, ethane has similar properties at lower temperatures, and becomes immiscible with fatty materials of even lower molecular weight at such lower temperatures. For example, liquified ethane having a critical temperature of about 32° C. begins to exhibit two-phase behavior with amyl stearate having a molecular weight of about 352 at temperatures above 19° C. Amyl stearate is of sufficiently low molecular weight that it does not form a two phase system with subcritical liquified propane. Mixtures of ethane and propane may be provided which have intermediate properties.

Cholesterol, depending upon extraction conditions and egg yolk composition, can be present as a monomer (molecular weight about 387), a hydrogen-bonded dimer (effective molecular weight about 773) or as a fatty ester such as cholesterol oleate (molecular weight about 612). Free cholesterol will associate through hydrogen bonding of its hydroxyl groups to from dimers having effectively twice the molecular weight of the free cholesterol, thereby reducing its solubility in the liquefied gas phase. However, by including a minor amount (e.g., from about 0.2 to about 3 weight percent, based on the weight of the liquefied subcritical gas) of a low molecular weight hydrogen bonding agent in the system, such as a lower alkyl alcohol (e.g., methanol, ethanol, propanol) or less desirably a lower alkyl acid (e.g., acetic acid), the cholesterol may be at least partially hydrogen-bonded to the low molecular weight hydrogen bonding agent, forming, for example, low molecular weight cholesterol-ethanol dimers which have relatively lower molecular weight than that of the fatty triglycerides of the egg yolk. [See, "The Solubility Relationships of High Molecular Weight Fatty Acids and Their Esters in Propane Near the Critical Temperature", Trans. Am. Inst. Chem. Engrs., 40, 675–894 (1944) ; Hixson, et al., "Liquid-Liquid Extraction Employing Solvents in the Region of Their Critical Temperatures", Trans. Am. Inst. Chem. Engrs., 38, 891–930 (1942)].

The phosphatide and phospholipoprotein components of egg yolks have significant molecular weight, and have ionic interaction which greatly increases their effective molecular weight, causing these materials to be substantially insoluble in liquified ethane. Accordingly, the free cholesterol and fatty acid esterified cholesterol is selectively removed in near subcritical ethane preferably containing a low molecular weight hydrogen-bonding agent at temperatures below protein denaturation temperatures at which egg yolk triglyceride solubility is reduced, and phosphatides are substantially insoluble. Ethane may be removed from egg yolk by vacuum treatment relatively easily in comparison to less volatile hydrocarbons such as hexane methyl ether, or ethyl ether. The near critical ethane-extracted egg yolk may be flushed with a gas such as nitrogen or carbon dioxide to remove traces of ethane or other low near subcritical fluid component. Ethane is also substantially inert as a food processing ingredient, as is propane nitrous oxide and various freons.

Figure 9:
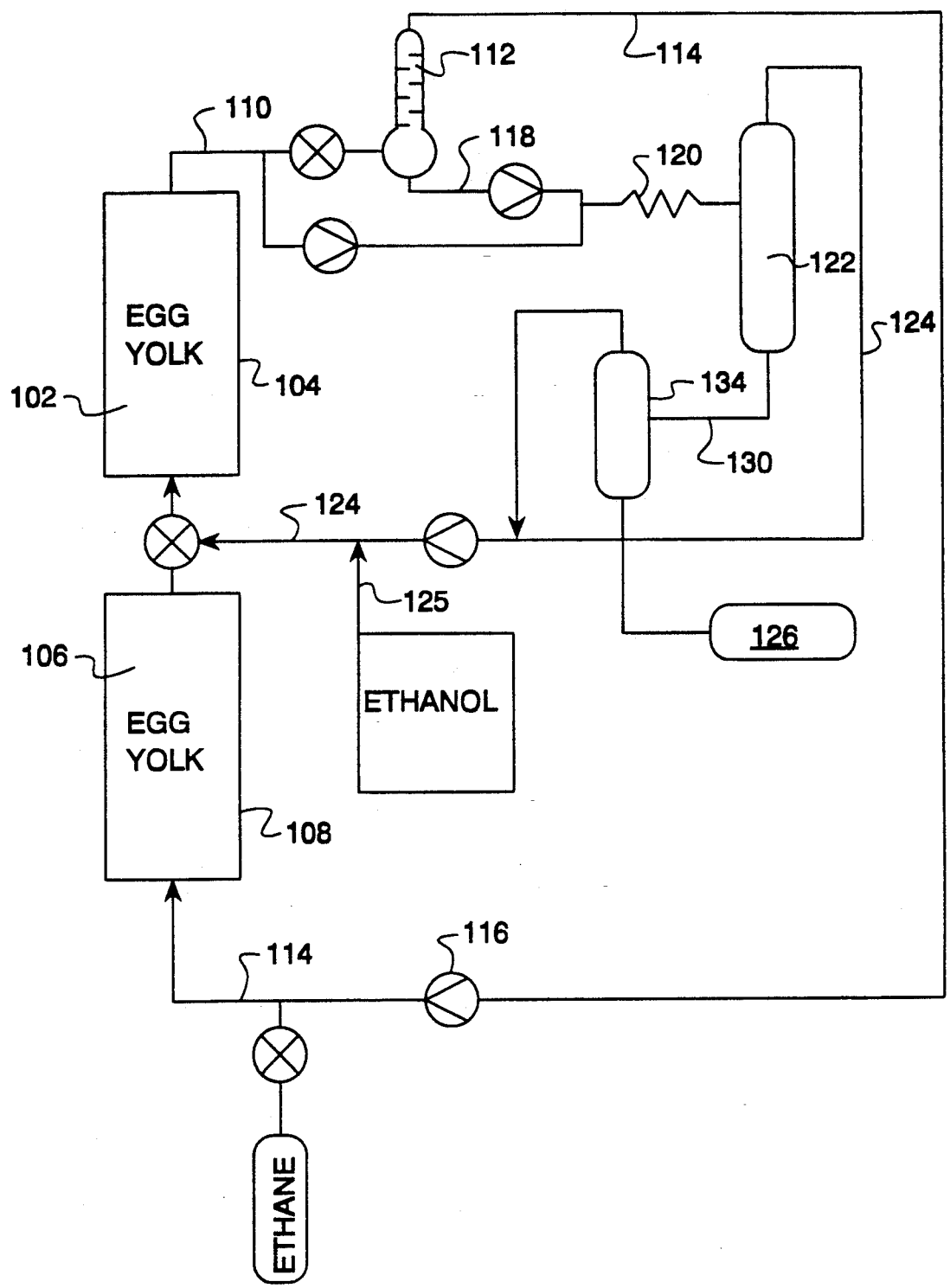
FIG. 9 is a schematic illustration of a process flow diagram of a method for removing cholesterol from dried whole egg or dried whole yolk.

Batch, concurrent and counter-current extractions may be carried out using near subcritical ethane or the like. Schematically illustrated in FIG. 9 is a cholesterol extraction system for dried egg yolks utilizing an inert, food-grade liquified gas having a critical temperature not more than 15° C., and preferably not more than 5° C. above the denaturation temperature of egg yolk proteins. Ethane near its critical temperature of 32.2° C. and above its critical pressure of 48.2 atmospheres or ethane/propane mixtures which are predominantly ethane, are preferred. Examples of other inert liquified gases, and their critical temperatures and critical pressures are:

|  | Critical temperature °C. | Critical pressure (atm.) |
|---|---|---|
| $CO_2$ | 31.1 | 72.8 |
| $CBrF_3$ | 67 | 39.1 |
| $CHF_3$ | 25.9 | 47.7 |
| $C_2F_6$ | 24.3 | — |
| $CF_3Cl$ | 28.9 | 38.7 |

FIG. 9 is a process flow diagram for a method for removing cholesterol from dried whole egg or dried egg yolk. As shown in FIG. 9, dried, powdered or flaked undenatured egg yolk 102 (e.g., having less than 5 weight percent moisture) which may be salted or unsalted is placed in a vacuum pressure vessel 104. Partially extracted dried egg yolk 106 (which has been extracted in ethane in a previous cycle, as will be described) is placed in a vacuum/pressure vessel 108. Two stages are used to achieve a partial counter-current effect. The vessels are flushed with inert gas (e.g., $CO_2$, nitrogen) and evacuated to withdraw all oxygen. Pure liquefied ethane 110 is introduced at a temperature above the multiphase point for the egg yolk triglycerides but below the critical temperature for ethane, such as a temperature of 25°–30° C. After filling the system, a recycle stream of ethane is used for the ethane flow, as shown in FIG. 9. The liquid ethane preferentially extracts cholesterol and ethanol from the egg yolk 106, while minimizing the extraction of egg yolk triglycerides. In this regard, the extraction temperature is generally above the multi-phase point at which the egg triglycerides lose their miscibility in the ethane. However, temperature fluctuation and concomitant variation of the amount of ethane in the yolk fat phase may be used to assist extraction. In this regard, the ethane flow may be stopped and the vessel 108 cooled at least once by 5°–10° C. or more to render the yolk triglycerides miscible in the ethane or to increase the amount of ethane dissolved in the yolk triglyceride phase. The vessel 108 is then heated back to 25°–30° C. to reduce the ethane in the triglyceride phase while removing cholesterol therefrom. The cholesterol, being of lower molecular weight, is more soluble, and is preferentially extracted. The egg yolk phosphatides and phospholipoprotein complexes are substantially insoluble in the ethane, because of their ionic self-associative properties. The ethane which passes through the egg yolk in the column is withdrawn from the top of the column 106. The ethane which has passed through the vessel 106 is introduced into the vessel 104 containing dried egg yolk 102. A recycle stream of ethane 124 with a small amount of a hydrogen-bonding lower alkyl alcohol or acid 125 such as ethanol or acetic acid (e.g., 1–2 weight percent ethanol based on the weight of ethane) is included in the ethane recycle stream.

The ethanol assists the preferential extraction of cholesterol by acting as a hydrogen bonding agent for the free cholesterol, thereby limiting the formation of cholesterol dimers having a doubled molecular weight and correspondingly decreased solubility. The dried whole egg or egg yolk may tend to physically entrap the cholesterol, and the ethanol or other hydrogen bonding agent assists in penetrating the dried particles to remove cholesterol. A small amount of water may be included in the ethane stream if desired for this purpose.

The liquid ethane/ethanol mixture 110, after passing through the egg yolk 102, contains a mixture of yolk extractants including cholesterol and some yolk triglyceride and is conducted from the top of the column 104. A portion (e.g., 10-50 volume percent) of the extractant mixture 110 is conducted to a refluxing fractional distillation column 112 where a portion thereof (e.g., 50 weight percent of the ethane) is distilled off as a substantially pure ethane stream 114 at low temperature for recycle introduction in the liquid state at 25°-30° C. into column 108 by recycle thermal conditioner/compressor 116, as shown in FIG. 9. The remaining "still-bottom" ethanol/ethane/mixture 118 containing the cholesterol is combined with the remaining portion of the stream 110 and heated in a heater 120 to a temperature above the critical temperature (at a pressure slightly above the critical pressure) to cause phase separation in a separator 122 into an oil-cholesterol liquid phase 130 and an ethane supercritical gas phase 124 containing ethanol (evaporation of the ethane may alternatively be used to provide a "purer" ethane for recycle at greater heating and compression cost). The oil/cholesterol layer 130 is stripped of ethane and ethanol in vacuum stripper 134 and sent to tank 126. The ethane/ethanol mixture is recycled to vessel 104. After passing ethane/ethanol in about 2-30 times the weight of egg yolks, through the column 104, the column 104 is reconnected to become column 108, a new vessel containing fresh dried egg yolks is connected as a vessel 104, and the column 108 is vacuum-stripped of ethane to provide a finished product. While this example is described using dried egg yolks, it may also be used to process dried whole eggs.

Figure 10:
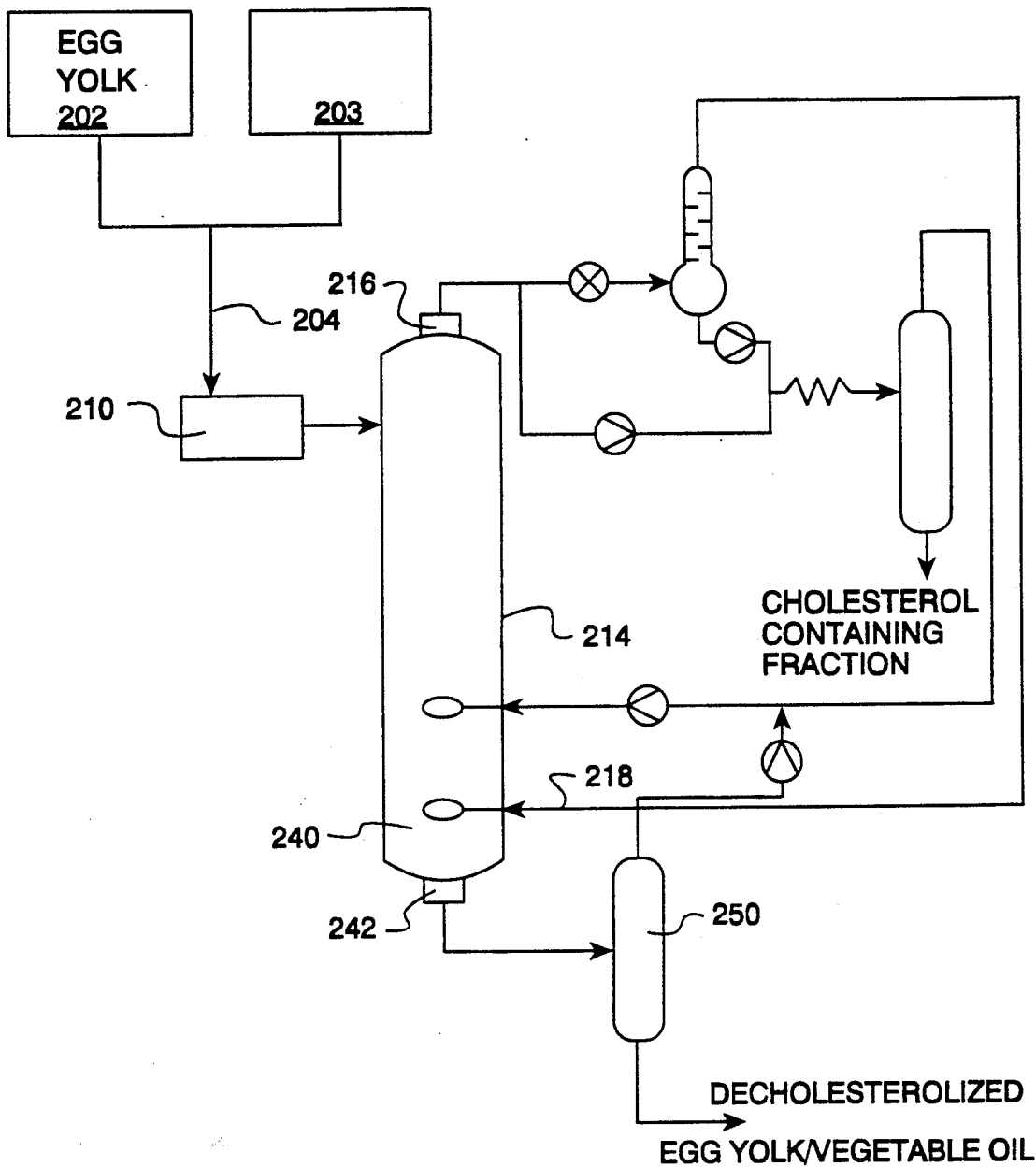
FIG. 10 is a schematic illustration of a continuous counter-current cholesterol extraction system.

For products in which the whole egg or egg yolk may be combined with vegetable oils or other fats, FIG. 10 illustrates a continuous counter-current cholesterol extraction system. The vegetable oil 203 or other fatty triglyceride (e.g., canola oil, soybean oil, etc.) is combined with dried egg yolk or dried whole egg 202 in amounts sufficient to form a pumpable paste or slurry 204, such as a slurry consisting of from about 10 to about 40 percent by weight of emulsified whole egg or whole egg yolk (water-in-oil), dried egg yolk, or dried whole egg, and 60-90 percent soybean oil. The vegetable oil tends to dissolve the egg yolk fats, and cholesterol components. The oil-yolk mixture is continuously introduced by a high pressure pump 210 into high pressure counter-current extraction column 214 at a point near the upper outlet 216. The column 214 is used to establish a concentration gradient and counter-current flow to preferentially remove cholesterol while minimizing removal of proteins, phosphatides, egg yolk triglycerides and phospholipoproteins.

In operation, liquefied ethane 218 containing a small amount of a hydrogen bonding agent such as 1-3 weight percent ethanol and/or acetic acid is introduced at the bottom of column 214 under pressure, flow rate and temperature conditions at which the relatively low molecular weight free cholesterol and cholesterol esters are significantly dissolved, but at which the high molecular weight triglycerides are less soluble and form a separate phase. Acetic acid may be a particularly desirable hydrogen bonding component in the ethane stripping liquid for egg products which will be used in acidified foods such as mayonnaise, where processing to remove substantially all traces of the acetic acid may be eliminated. The triglyceride phase and the egg yolk solids are heavier than the light, liquified ethane phase, and accordingly move counter-current to the upwardly moving ethane. The concentration of cholesterol accordingly increases to a maximum at the top of the column. More saturated and lower molecular weight triglycerides are also concentrated toward the top of the column and are preferentially removed with the cholesterol. The temperature in zones of the column or adjunct treatment chambers containing egg components may vary, but does not exceed the denaturation temperature of the egg proteins, which will be damaged at high temperatures. However, it is noted that the temperature in the upper zone of the column which does not contain egg protein may exceed the egg denaturation temperature if desired to assist in providing an internal reflux. In the illustrated embodiment, the ethane, or ethane/propane mixture, (with ethanol) may be introduced at a pressure of about 600-700 psi and a temperature of 20°-30° C. at a rate of about 2-15 times the rate of introduction of egg/vegetable oil dispersion. If a higher temperature is desired, ethane/propane mixtures, or other inert liquefied gases such as fluorocarbons having a critical temperature not significantly greater than the egg denaturation temperatures (e.g., 120°-160° F. ) may be used. The liquified ethane also dissolves in the separate vegetable oil/egg triglyceride(s) phase and serves as a diluent to dissolve the cholesterol and high melting fats so that they are accessible for cholesterol removal at the relatively low operating temperatures.

The liquefied ethane phase is substantially less dense than the downwardly moving vegetable oil stream. The pressure, temperature, column distances and flow rates of egg/oil slurry and liquid ethane are selected so that the cholesterol is progressively dissolved from the triglyceride into the upwardly moving liquid ethane/ethanol phase.

The decholesterolized egg yolk solids and vegetable oil flow to the bottom 240 of the extraction column, where they are pumped out by positive displacement pump or screw extruder pump 242 to an ethane vacuum stripping column 250. The vegetable oil/decholesterolized egg yolk slurry may be centrifuged if desired to recover the egg yolk solids, and the vegetable oil may be re-used. The slurry may be stripped using an inert gas such as $CO_2$ or $N_2$ under pressure and/or vacuum conditions to assist ethane and ethanol removal. The vegetable oil, decholesterolized egg yolk slurry may also be used directly in the manufacture of vegetable oil containing products such as mayonnaise and salad dressings.

The relative flow rates of ethane/ethanol and vegetable oil may be adjusted to remove, for example, 3-30 weight percent of the triglycerides of the vegetable oil/egg yolk slurry, together with 75-99 percent of the cholesterol, in the output stream. Operation for removing cholesterol from animal fats is similar.

Figures 11, 11A, 11B:
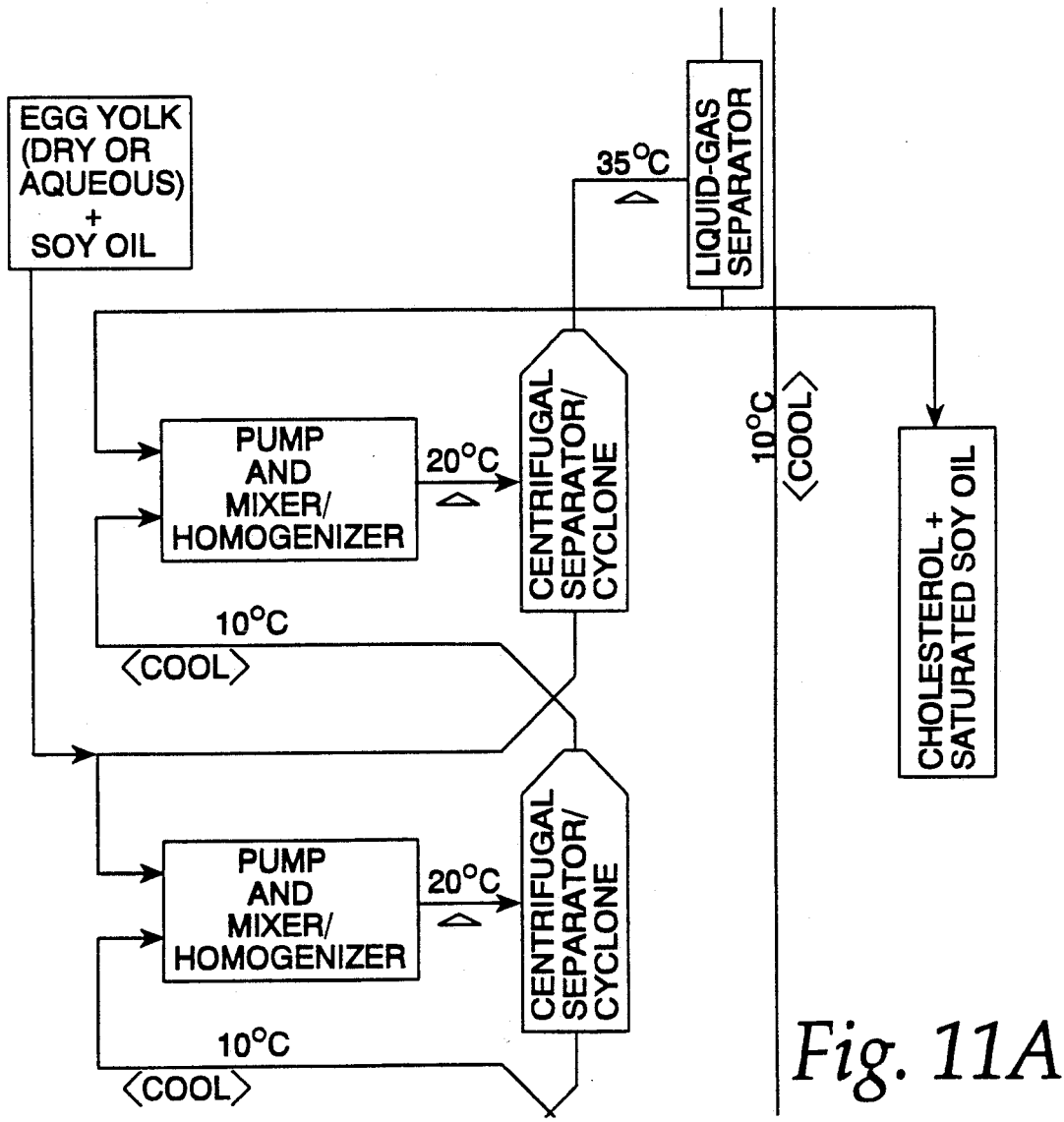
FIGS. 11A and 11B are a schematic illustration of a multi-stage cholesterol removal system using centrifugal phase separation.
Figure 11B:
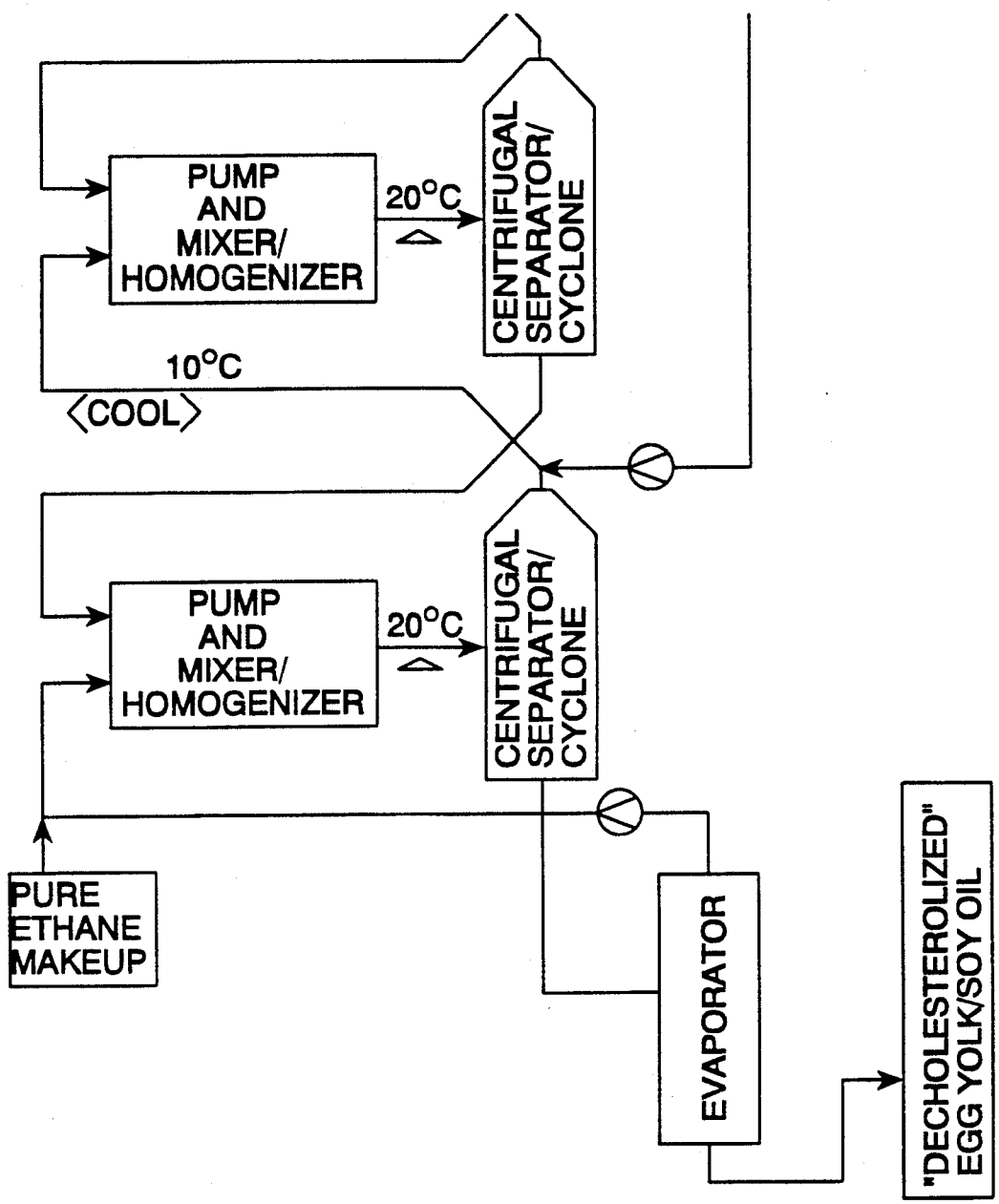

The cholesterol may also be removed using a multistage counter-current cascade system 300 such as illustrated in FIGS. 11A and 11B, in which the light ethane/ethanol phase is centrifugally separated using cyclone units (e.g., a parallel series of Dorrclone cyclone separator units having a diameter of about 1 centimeter) or a centrifuge unit, with cascaded, counter-current feedback. In FIG. 11, the light, subcritical gas phase is shown exiting from the upper exit port of the centrifugal or cyclone separators, and the heavier phase is shown exiting from the lower exit port of the centrifugal or cyclone separators. In pumping/mixing stages, the ethane/soy/egg yolk mixture may be cooled to miscibility of the triglycerides and liquified gas, to achieve thorough mixing at each stage and the mixture may be heated to immiscibility prior to centrifugal separation at each stage. Heat exchange devices (not shown) may be used to reduce the energy requirements. The system of FIG. 11 may also be used with aqueous egg or egg yolk solutions, fluid milk solutions, butterfat, tallow, lard, turkey fat, chicken fat and other cholesterol-containing materials. As described hereinabove, a hydrogen-bonding cosolvent for cholesterol, such as ethanol, may be used with the subcritical ethane.

The cholesterol-containing output stream may be separated from the cholesterol in a variety of ways and at least a portion of the noncholesterol components returned to the extracted yolk or other cholesterol-reduced end product, if desired. The cholesterol may be separated chromatographically, or with a selective cholesterol absorbant such as activated carbon, or may be selectively extracted (e.g., from alcohol solution) and precipitated. The entire mixture of extracted material may be hydrolyzed to provide a mixture of fatty acids, glycerol and free cholesterol which may be resolved into components.

The mixture, or hydrolyzed mixture, may also be separated by counter-current super- or subcritical fluid extraction by enhancing, rather than limiting the hydrogen bonding or other dimer forming tendency of the cholesterol, so that the cholesterol is not dissolved as much as other components. In this regard, an oil soluble or oil dispersible material such as partial cellulose esters (e.g., cellulose stearate; partially acylated cellulose, etc) having hydrogen bonding groups may be dissolved or slurried in the extraction oil containing the cholesterol, and the mixture extracted with a non-hydrogen bonding solvent such as near subcritical liquefied ethane or propane, to remove non-cholesterol components.

The cholesterol or cholesterol component of a cholesterol-containing mixture may also be formed into magnesium cholesterol alkoxides and/or magnesium cholesterol alkoxyl carbonates to increase the effective molecular weight and decrease the solubility of the cholesterol in a supercritical or subcritical solvent such as carbon dioxide, ethane, propane or fluorocarbons. Magnesium cholesterol alkoxide or magnesium carbonate cholesterol compounds including dimers and polymer-bound materials may be formed which are significantly increased in molecular weight over free cholesterol, and reduced in solubility in the extractant, as compared to the free cholesterol material. The extraction may be carried out in a counter-current manner, as previously described, using a near-critical liquefied gas (which need not be at a temperature below the denaturation temperature of egg protein because egg protein is not present) to preferentially dissolve and separate at least a part of the oil and flavor components, leaving a concentrated cholesterol-containing material.

More specifically cholesterol removal from fats and oils may be carried out by means of interaction with alkaline earth alkoxides, and preferably magnesium alkoxides of lower $C_1$–$C_3$ alcohols, such as magnesium ethoxide or methoxide. The magnesium alkoxides interact with the free hydroxyl radical of the cholesterol molecules at low to moderate temperature. Magnesium alkoxides are easily prepared by reacting surface-clean magnesium under anhydrous (Grignard-like) conditions with an alcohol, such as methyl alcohol or ethyl alcohol. Higher alkoxides may be prepared by displacement reaction and evaporation of the lower-boiling alcohol. For example, magnesium methoxide may be prepared in methanol, which may be displaced with ethanol to form magnesium ethoxide. By displacing a lower alkyl alcohol moiety of the magnesium alkoxide with a polyhydroxy compound, such as glycerol, ethylene glycol, propylene glycol, sugars, starches, cellulose, etc., a polymeric magnesium alkoxide may be formed which is useful in phase separation of the cholesterol from other components of a cholesterol-containing mixture. Grignard reagents, such as ethyl magnesium bromide or chloride may also be titrated against the free cholesterol component of a cholesterol-containing oil to form a cholesterol magnesium alkoxide.

Magnesium alkoxides such as magnesium ethoxides and methoxides have reasonably good solubility in alcohols, fluorocarbons and alcohol-hydrocarbon mixtures when freshly prepared. However, after evaporation to dryness from solution, such alkoxides may be insoluble. These properties may be used to advantage in the proposed cholesterol removal methods.

For example, in accordance with such methods, a substantially anhydrous animal fat containing cholesterol, such as tallow or milkfat is provided at a temperature in the range of 0°–100° C., preferably in a fully melted or dissolved condition at 30°–50° C. The fat may be pretreated with a specific cholesterol hydrolase to hydrolyze fatty acids esters of cholesterol. The animal fat may be dissolved in an inert solvent such as hexane or propane to reduce the viscosity and melting temperature of the fat, and to decrease the solubility of polyvalent cholesterol alkoxides, if desired. The cholesterol-containing fat or oil is contacted with a magnesium alkoxide of a low carbon alcohol such as magnesium methoxide or magnesium ethoxide, a food grade polyhydroxy material such as magnesium starch or magnesium cellulose alkoxide, and/or with an inorganic substrate having magnesium surface alkoxide groups. A stoichiometric excess of alkoxide may be used based on reaction with cholesterol, free fatty acids, mono- and diglycerides and other relatively labile-hydrogen-containing compounds, plus an amount to titrate any water present.

In this regard, an alkoxide solution may be directly introduced into the anhydrous animal fat, to produce mono- and dicholesterol alkoxides. An excess of the alkoxide is used to react with any excess water in the animal fat. The alkoxide will react with the free hydroxyl of the cholesterol to release the ethanol or other lower alcohol:

(Chol)—OH + Mg(O—Et)$_2$ (Chol)—O—Mg—O—Et;
(Chol)—O—Mg—O—(Chol) + EtOH

A vacuum and nitrogen purge may assist in removal of the lower alcohol, to drive the exchange reaction at low temperatures. The cholesterol alkoxides may have reduced solubility in the animal fat and may be adsorbed on inorganic and other surfaces under anhydrous conditions.

Simple alkoxides may be caused to form "half-carbonates" by contact with (anhydrous) carbon dioxide. The solubility of a cholesterol carbonate-alkoxide is further reduced in solvents such as subcritical liquified ethane or propane or supercritical gases.

(Chol)-O—Mg—O-(Chol) + CO$_2$ ⟶

-continued

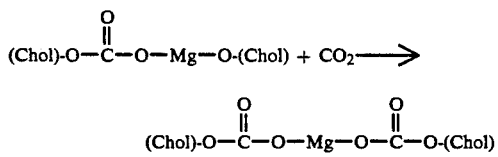

$$(\text{Chol})\text{-O}-\overset{\overset{\text{O}}{\|}}{\text{C}}-\text{O}-\text{Mg}-\text{O}-\overset{\overset{\text{O}}{\|}}{\text{C}}-\text{O-(Chol)}$$

Such carbonates have reduced solubility, and may precipitate out of the fat or oil at reduced temperature. The carbonates are more stable than the alkoxides to hydrolysis, but may nevertheless be easily dissociated by water or dilute edible acids. The carbonates may be made by bubbling dry carbon dioxide through the cholesterol magnesium alkoxide-containing butterfat or other triglyceride (preferably under at least 2 atmosphere pressure) after the cholesterol alkoxides have been formed. In any event, the chemical "mildness", complete reversibility and food-grade nature of the magnesium alkoxide and/or carbonate treatment is an important aspect of the treatment process.

The cholesterol containing fat or oil may also be treated by contacting the anhydrous animal fat with an insoluble or immobilized magnesium alkoxide, so that the cholesterol is also immobilized. Insolubilized magnesium alkoxide powders or fibers may be used as an insoluble, reactive adsorbent. The immobilized alkoxide may also be preferably formed as a polymer adsorbent of a polyhydroxy material such as a starch alkoxide or cellulose alkoxide, by introducing anhydrous starch into an alkoxide solution, and removing the solution or solvent. Starch and cellulose are both "food-type" materials which are inexpensive. The magnesium may bridge some of the oxygen groups of starch hydroxyl groups to crosslink the starch or may form mono-starch lower alcoholates:

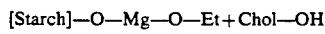

[Starch]—O—Mg—O—Et+Chol—OH

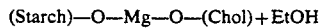

(Starch)—O—Mg—O—(Chol)+EtOH

In the same manner, an inorganic substrate such as an absorbent clay (which has been heated to, e.g., 400° C. to remove surface water) may be treated with an alkoxide solution and evaporated to dryness, to form surface magnesium alkoxide groups. These groups can react with cholesterol:

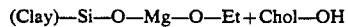

(Clay)—Si—O—Mg—O—Et+Chol—OH

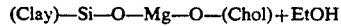

(Clay)—Si—O—Mg—O—(Chol)+EtOH

These immobilized inorganic and organic alkoxides may be contacted with the animal or other cholesterol-containing oil or fat to form surface cholesterol alkoxides, whether in batch mode, or by passing the animal fat through a column of the surface-reactive organic or inorganic solid substrates. Stearic hindrance will tend to prevent removal of the magnesium from the solid substrate, so that only one cholesterol is reacted to the magnesium, which remains attached to the solid substrate.

Other cholesterol components, including esterified cholesterol, free cholesterol and dissolved cholesterol magnesium alkoxides will have a tendency to agglomerate at the surface-bound or adsorbed cholesterol alkoxide, under low-temperature conditions which may be settled, filtered or centrifuged from the animal fat, to provide a purified animal fat having reduced cholesterol.

The recovered cholesterol alkoxides may be discarded or hydrolyzed by addition of water. Other hydroxyl or labile hydrogen compounds of the animal fat such as vitamins, mono- and di- glycerides, peptides, proteins, lecithins and fatty acid components also separated from the animal fat by the alkoxide treatment may be recovered (if present) and may be separated from the cholesterol by various means such as adsorption chromatography and returned to the animal fat if desired. Under the moderate (low temperature-short time) reaction conditions, there is little, if any, damage to these materials.

As an example, 250 grams of food grade, edible oil absorptive clay is heated to 700° C. and then dried in a vacuum oven at 100° C. for 4 hours. 200 grams of freshly prepared 5 weight percent solution of magnesium ethoxide in anhydrous ethanol is prepared by reacting Grignard magnesium turnings with ethanol, and the solution is clarified and filtered. The dried clay is slurried in the ethoxide solution, which is heated to boiling, cooled to fill all pores, and then evaporated to dryness, and heated to 90° C. under vacuum. 1,000 grams anhydrous butterfat containing about 0.2–0.3 weight percent cholesterol (90% free), less than 0.05 percent moisture, less than 0.5 weight percent free fatty acid and less than 1 weight percent mono- and di- glycerides is mixed with 200 grams of the alkoxide-treated clay absorbent at a temperature of 50° C. with stirring under vacuum (to remove ethanol) for 1 hour. optionally, an ethyl magnesium chloride Grignard reagent may be titrated into the mixture in up to a stoichiometric amount based on free cholesterol. The treated butterfat is then centrifuged or filtered under anhydrous conditions to separate the butterfat from the clay. The clarified, treated butterfat should be substantially reduced in cholesterol. The clay may be washed with anhydrous hexane to recover excess triglycerides.

The washed clay is then stirred in 95 percent ethanol/5 percent water to hydrolyze the adsorbed materials, including cholesterol, mono- and di- glycerides, vitamins and free fatty acids. These materials may be separated by absorption chromatography. Rather than slurrying, the butterfat may be conducted through a column containing the treated clay. Similarly, a solid absorbent may be prepared from cotton fibers which have been thoroughly dried under vacuum at 50° C. with a small nitrogen bleed for 12 hours. 250 grams of the dried cotton may be slurried with 250 grams of freshly prepared 5 weight percent magnesium ethoxide solution in ethanol, which is evaporated to dryness and dried under 50° C. vacuum to produce a cellulosic magnesium alkoxide having excess surface magnesium ethoxide.

The treated cellulose may be placed (or formed) in a column, and 1,000 grams of the anhydrous butterfat slowly conducted through the column under vacuum (to remove ethanol generated by reaction of the alkoxide with cholesterol and other components of the butterfat).

The butterfat which has passed through the column should be substantially purified of cholesterol. The magnesium alkoxide treated clay or cellulosic column material may be periodically washed, replaced or regenerated.

Silicon alkoxides (or halides, such as silicon tetrachloride) which may form soluble cholesterol silicon ethers unless immobilized, will react with surface hydroxyl groups of inorganic substrates to provide immobilized, cholesterol-reactive substrates with surface alkoxide groups.

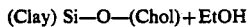

Strongly basic alkaline earth alkoxides, tin, or titanium alkoxides may react with or transesterify the triglycerides of the animal fat. Magnesium alkoxide on the other hand has very low basicity so it should not react with the triglycerides at low temperature, is non-toxic, generally non-catalytic and is destroyed by water. magnesium is water soluble, and is easily removed by a variety of safe and inexpensive cleanup steps such as water washing, or treatment with an ion exchange resin. Magnesium alkoxides, such as glycerol magnesium alkoxides (e.g., made by reacting glycerin with methyl magnesium alkoxide), may also be used in such separators. It will be appreciated that by forming cholesterol magnesium alkoxides in super- or subcritical fluid extraction mixtures, the effective molecular weight of the cholesterol component is increased. A subsequent super- or subcritical (preferably counter-current) extraction step will permit separation of these higher molecular weight cholesterol components from other components which were not separated in the initial extraction.

While the method of FIG. 10 has been described with respect to dried egg yolks and dried whole egg powder slurried in vegetable oil, it may also be used with whole liquid egg and whole liquid egg yolk, alone or slurried in vegetable oil. The ethane/alcohol extraction mixture has significant solubility in the water phase under the high pressure conditions, permitting rapid transport under conditions of moderate to high shear to the lipid zones in the aqueous phase of the egg. The liquid phase is much denser than the ethane phase, permitting easy separation of shear-induced emulsions and counter-current operation. For example, by appropriate counter-current mixing, coalescence and thermal cycling to increase and decrease the amount of ethane dissolved in the triglyceride phase with appropriate centrifugal separation stages, the cholesterol may be extracted to the ethane phase to produce a decholesterolized undenatured whole egg or whole egg yolk. It may be desirable to saturate the incoming ethane with water to prevent partial dehydration of the liquid egg or yolk. Vegetable oils may also be included in the egg or incoming ethane to substitute for part of the saturated fat of the egg yolk. In this manner, egg yolks or liquid whole eggs, having greatly reduced saturated fat and cholesterol content, may be produced.

Figure 12:
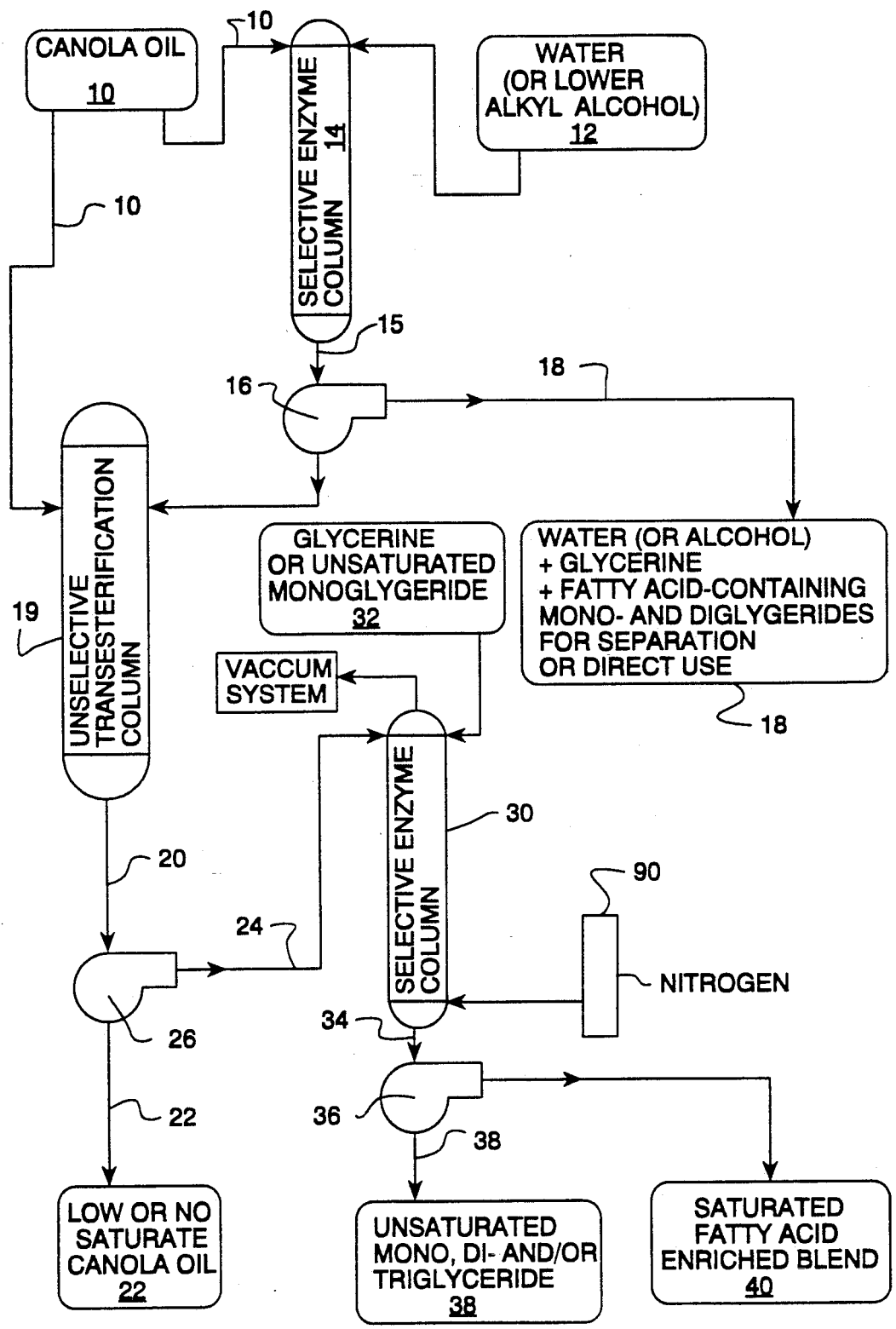
FIG. 12 is a schematic illustration of an integrated refining and counter-current transesterification system, which comprises a variety of processing methods.

The flow chart of FIG. 12 illustrates a method for producing transesterified oils with low or substantially no saturated fatty acid content.

As shown in FIG. 12, a source of canola oil 10 or other vegetable oil having a low (e.g., preferably less than 10 weight percent, and more preferably less than 7 weight percent) esterified saturated fatty acid content is provided as a starting material. High oleic sunflower seed oil and safflower oil may also be used. Other unsaturated oils such as soybean oil and cottonseed oil may also be used, but typically have relatively higher saturated fat content. The oil 10 is conducted to an enzymatic reactor 14 containing an immobilized delta-9 specific lipase, such as the lipase produced by *G. candidum*. [Iwai and Tsujisaka, Lipases, Borgstrum & Brockmann Ed., p. 443 (1984).] The delta-9 specific lipase may be immobilized in a suitable manner such as by inorganic support (Kieselguhr, Celite, etc.) or organic support (ion exchange resin, gel) and may be ionicly, covalently and/or hydrophobicly bound, as desired. Alternatively, a non-immobilized powdered or granular delta-9 specific lipase may be used or a whole cell cross-linked preparation of *G. candidum* or another suitable microbe cultivated so as to produce delta-9 specific lipase.

A glycerol replacement material 12 such as water or a low alkyl alcohol (e.g., ethanol or methanol) is also introduced into the reactor 14 in appropriate amount to achieve the desired degree of hydrolysis or alcoholysis. If water is introduced with the canola oil into the reactor 14, the enzyme selectively hydrolyzes the delta-9 unsaturated acids of the canola oil, such as oleic acid, linoleic acid and linolenic acid, leaving the saturated components esterified to the glycerine component of the oil. If instead, a lower alcohol is introduced, monoesters of the unsaturated acids are produced such as the methyl or ethyl esters of oleic, linoleic and linolenic acids, also leaving the saturated acid components esterified to the glycerine component of the oil. Desirably, at least 1.5 times the molar amount of water or alcohol to complete the hydrolysis or alcoholysis, and more desirably at least 4 times the molar amount will be emulsified with the oil in the reactor 14. If it is desired to limit hydrolysis or alcoholysis (e.g., to produce a diglyceride byproduct), lesser ratios may be used.

The selectively hydrolyzed (or lower alkyl monoesterified) mixture 15 produced contains unsaturated fatty acids (or esters), partial glycerides of saturated fatty acids, free glycerol and unreacted water or alcohol. Depending upon the degree of completion of the reaction, some unsaturated fatty acids may also remain esterified to the original glycerol component. Because of the relatively low saturated fatty acid content of the canola oil (e.g., 6 percent) and because of the high selectivity of the lipase (e.g., greater than 20:1), the unsaturated fatty acid component or monoester component produced in the mixture 15 is substantially pure (e.g., less than 0.4 weight percent saturated fatty acid) unsaturated fatty acids having a cis- double bond in the 9-position.

These components are separated in separator 16 to provide a stream 17 of unsaturated fatty acid (or fatty acid low alkyl monoester and one or more streams 18 of other components such as monoglycerides of saturated fatty acids, glycerine (+water or alcohol). The separator 16 may use any appropriate separation technique to separate the components. For example, excess alcohol may be used as a solvent, and the components selectively precipitated out by temperature reduction. Fractional crystallization, solvent/solvent extraction and supercritical solvent extraction may also be used to separate the unsaturated fatty acid or alcohol ester components from the other components.

Selective lipases (e.g., *Geotrichum candidum* lipase or whole cells) selectively hydrolyze (or esterify) unsaturated fatty acids. The selectivity may be 5-30 times greater for oleic acid than stearic or palmitic acids. By using such a selective lipase on oil such as canola oil which is already low in saturated fatty acids, a mixture of unsaturated fatty acids and a small amount of saturated monoglycerides may be produced.

The melting points for both palmitic and stearic monoglycerides are significantly higher than the corresponding free saturated fatty acid:

|  | Meeting Point °C. |
| --- | --- |
| Stearic Acid | 69.6 |
| Stearic-OH—OH Monoglyceride | 81.5 |
| OH-Stearic-OH Monoglyceride | 74.5 |
| Palmitic Acid | 62.9 |
| Palmitic-OH—OH Monoglyceride | 77.0 |
| OH-Palmitic-OH Monoglyceride | 68.5 |
| Oleic Acid | 16.25 |
| Oleic-OH—OH Monoglyceride | 35 |

The higher melting point and the different chemical and physical characteristics of the saturated fatty acid monoglycerides, as compared to the corresponding saturated free fatty acids, provides a greater thermodynamic driving force for fractional crystallization. Stearic-OH-OH and Palmitic-OH-OH, which have the highest melting points, are the predominant monoglycerides produced by low-temperature, selective hydrolysis of unsaturated fatty acids from canola oil, because the saturated fatty acids are largely in 1,3 positions of canola and other low-saturate vegetable oils.

Canola oil may be selectively partially hydrolyzed in a solvent such as hexane or propane, fractionally crystallized by (after glycerine removal, such as centrifugation), and again passed through a second selective hydrolysis column to redistribute and further hydrolyze the mixture, followed by a second fractional crystallization step. In this way, complete hydrolysis, which is difficult with enzymes, may be avoided.

It may also be economical to crystallize a fatty acid mixture from hydrolyzed canola oil to prepare a 3% fatty acid mixture, followed by treatment with a urea-/oleic acid adduct or silicalite/oleic acid adduct to remove most of the remaining saturated fatty acids. The urea (or silicalite) adduct may be periodically directly regenerated at elevated temperatures (e.g., below the 133° C. melting point of urea), using a dried 6% or 3% saturated fatty acid mixture prepared by hydrolysis (and fractional crystallization) of canola oil. Complete hydrolysis of the canola oil to form fatty acids is not necessary, because the triglycerides do not form adducts.

Because fatty acid dimer formation is limited in solvents such as ethanol, the mutual solubility effects of dimer formation which inhibit purification by crystallization may be minimized in such solvents.

One or more streams 18 of saturated monoglycerides and other components may be refined for use as a food grade end product, may be further hydrolyzed by enzyme or alkaline catalysts, or may be further esterified with saturated or unsaturated fatty acids, as will be discussed.

The unsaturated fatty acid (or lower alkyl monoester) component 17 is introduced into a transesterification reactor 19 together with canola oil 10, for transesterification to produce a low saturate triglyceride. The reactor desirably contains an immobilized nonspecific transesterification lipase such as *Candida cylindracae* or *Candida rugosa*. An immobilized 1-, 3-specific enzyme may similarly be used, because the saturated acid content of canola oil is concentrated in the 1 and 3 positions. The lipase may be immobilized on a high surface area inorganic or organic support, as previously described or may be non-immobilized. The reactor 19 may be a batch, or continuous concurrent reactor, but preferably is a counter-current reactor to substantially reduce the amount of unsaturated fatty acid or monoester 17 utilized to achieve a desired degree of saturated acid removed from the triglyceride oil. The transesterified stream 20 contains the transesterified triglyceride 22 and a transesterified fatty acid mixture 24 which are separated by separator 26. For example, in a batch or concurrent continuous reactor at equilibrium, a canola oil 10 having 6 weight percent saturated fatty acid mixed with unsaturated fatty acid or monoester 17 having 0.3 percent saturated fatty acid content in a 1:3 molar ratio will produce a triglyceride oil and a fatty acid or monoester mixture 20 having approximately 1.7 weight percent of saturated fatty acid in each component. However, in a counter-current transesterification process, a substantially smaller amount of the unsaturated fatty acid monoester or component is used to achieve a desired degree of fatty acid removal from the oil component; the triglyceride oil component 22 approaches the composition of the fatty acid stream 17, and the composition of the reacted stream 20 approaches the composition of the oil 10 in fatty acid content.

The saturated fatty acid or monoester may, in turn, be separated from the unsaturated fatty acid or monoester, by methods such as by fractional precipitation from ethanol solution or supercritical fluid extraction.

However, selective esterification or transesterification may also be used to preferentially separate unsaturated fatty acids or monoesters. For example, the mixture of saturated and unsaturated fatty acids or fatty monoesters 24 may be conducted into a reaction column 30 containing an immobilized delta-9 specific lipase, together with glycerine 32 or an unsaturated mono- or diglyceride. The reactor 30 should desirably have a high surface area of at least about 500 square meters per cubic meter. The fatty acid or monoester mixture and glycerine are introduced in a desired ratio to produce a desired mono-, di- or triglyceride end product, based on the unsaturated fatty acid content of the mixture 24. As light stoichiometric excess of unsaturated fatty acid moiety is desirable.

The reactor 30 is maintained at a subatmospheric pressure of less than about 100 mm of mercury and preferably less than 30 millimeters of mercury, and is heated using internal high surface area heating elements distributed throughout the volume of the reactor to a temperature of at least 40° C., and preferably at the highest temperature the enzyme can tolerate with good efficiency of transesterification. The temperature may be higher at the outlet end of the column under low water conditions. A small counter-current nitrogen purge may be used to remove water or lower alkyl alcohol (e.g., ethanol). As the mixture of glycerine and fatty acid or monoester 20 passes through the column, the unsaturated delta-9 fatty acid or monoesters are selectively reacted with the glycerine to form mono-, di- and triesters, as desired. Lower alkyl monoesters more readily form triglycerides, which are difficult to form from the fatty acids without a high level of di- or monoglycerides. The saturated fatty acids or monoesters remain substantially unreacted in the transesterified product mixture 34, which is separated into its components by separation step 36, such as a fatty acid caustic wash, steam stripping, selective solvent removal, solvent fractionation, etc. The unsaturated mono-, di- and-/or triglyceride component 38 may be conducted to the selective hydrolysis reactor 14, to effectively recycle these unsaturated fatty acid components. The saturated fatty acid or monoester component may be used in other transesterification processes or as a desired end product. For example, the component 40 enriched in saturated fatty acid moieties may be esterified with the saturated mono and diglyceride stream 18 in a vacuum reactor like reactor 30, to provide a di- or triglyceride product which is relatively high in saturated fatty acid content. The end products may be refined by a variety of methods such as supercritical gas separation methods, solvent extraction methods, molecular distillation methods and the like.

The canola or other low saturate oil 10 is mixed with water or alcohol 12 and hydrolyzed or alcoholized in reactor 14, which contains an immobilized 1-, 3-specific lipase or a non- specific lipase. The hydrolysis or alcoholysis is desirably carried out until it is over 90% complete at the 1,3 position or the 1,2,3 positions, respectively. After substantially complete hydrolysis or alcoholysis of the saturated and unsaturated fatty acid components, the hydrolyzed or alcoholized mixture is selectively re-esterified with the glyceride (in the case of 1,2,3 hydrolysis or alcoholysis) or the 2-monoglyceride (in the case of the 1,3 specific hydrolysis or alcoholysis). Other non- enzymatic hydrolysis or alcoholysis methods may also be used, such as autoclave hydrolysis techniques or catalyzed alcoholysis techniques using an inorganic catalyst. If the oil 10 is unrefined and not deodorized, the glycerine may best be separated, purified and returned. Excess water or alcohol is separated in any appropriate manner by separator 16, such as by evaporation, centrifugation, extraction, etc. Approximately 6–10 percent of the glycerol or 2-monoglyceride is also removed, leaving a molar excess of fatty acid or fatty monoester over the remaining glycerol, which is only slightly greater than the amount of saturated fatty acid or monoester in the mixture. The mixture 18 having a 6–10% molar excess of acid or monoester groups over glycerol hydroxyl group is then selectively esterified in a high surface area vacuum column containing an immobilized delta-9 selective lipase, as previously described. The resulting esterified mixture 20 contains unsaturated triglycerides and some diglycerides of unsaturated acids, together with the excess saturated acid or saturated monoester component. The saturated fatty acids may be separated (at 22) from the unsaturated triglyceride in a conventional manner, as by alkaline wash and steam stripping or deodorization to remove free fatty acids.

As previously indicated, supercritical fluids such as supercritical carbon dioxide, and sub- or supercritical hydrocarbons such as propane, nitrous oxide or fluorocarbons may be used to selectively dissolve, precipitate or otherwise separate fatty acids, triglycerides and other edible fat and oil components. Such fluids may be used in a counter-current flow to remove water in enzyme esterification reactions, as an alternative to vacuum.

While the counter-current methods disclosed herein have been specifically described hereinabove with respect to low-saturate vegetable oil manufacture, such methods may be generally applied to enzymatic and transesterification reactions of vegetable, marine and animal fats and oils.

51586

A further process utilizing precepts of the inventions disclosed herein provides a triglyceride with any desired fatty acid composition, for example, a low saturate (less than 3% saturated fatty acids) triglyceride containing less than 3% mono and diglycerides and less than 1% residual free fatty acids. The process comprises the steps of hydrolyzing a triglyceride raw material to provide a mixture of glycerol, water and mixed free fatty acids, separating the glycerol and water from the free fatty acids, separating the glycerol from the glycerol and water stream, separating the desired fatty acids from the free fatty acids, and esterifying the separated glycerol and desired fatty acids to provide a rearranged triglyceride containing essentially desired fatty acids. Other fatty acids of particular chain length and/or configuration, not present in the starting vegetable oil, may optionally be mixed with the desired fatty acids to provide a tailored triglyceride product having improved properties.

Figure 13:
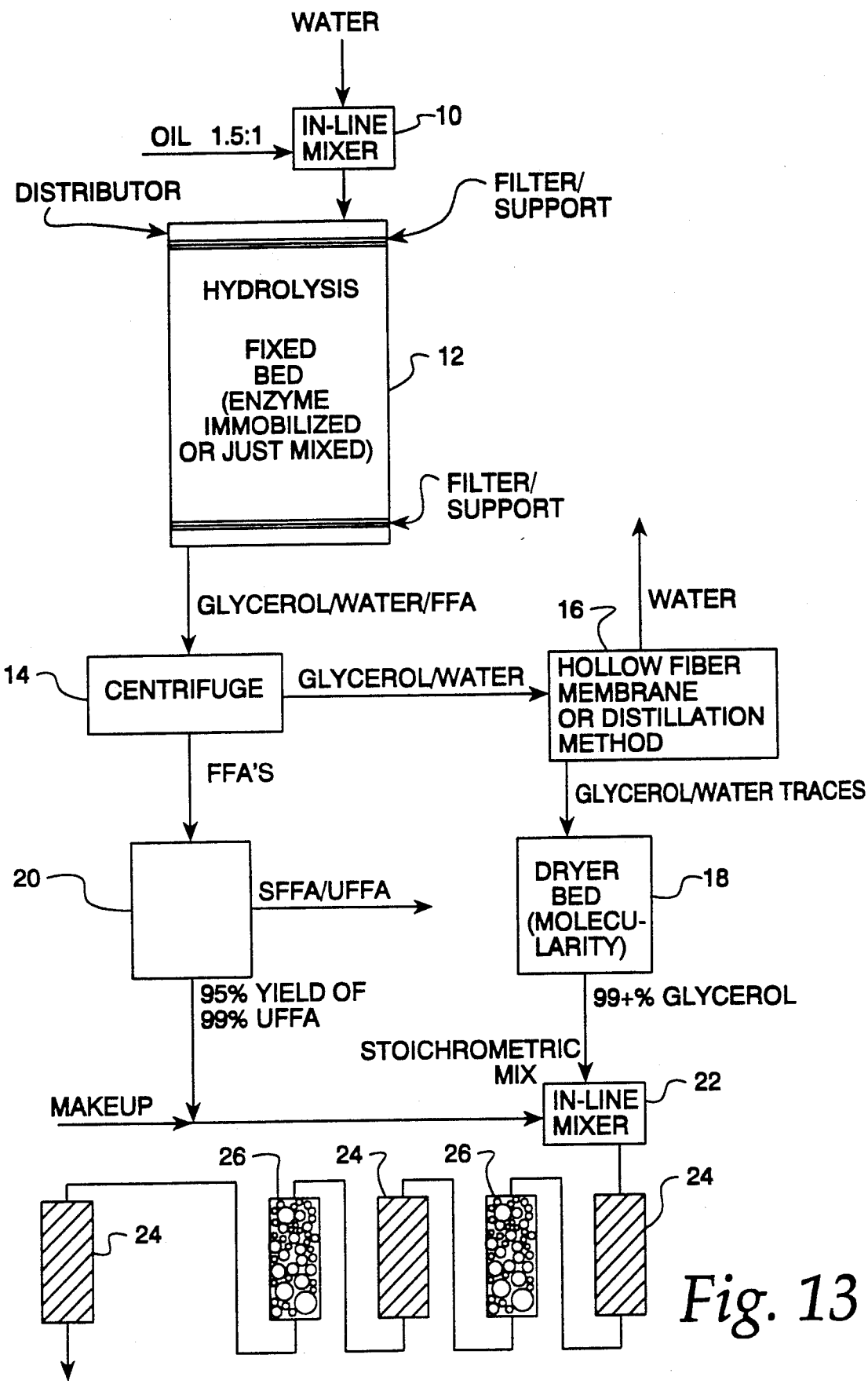
FIG. 13 is a schematic illustration of yet another embodiment of the present invention.

The process is best described by reference to FIG. 13 which illustrates a flow chart for a preferred embodiment of the process. The triglyceride oil feed to be modified and water are mixed together in an inline mixer 10 before introduction into a hydrolysis bioreactor 12. For example, in order to make an oil with less than 3% saturated fat, a preferred oil raw material is canola oil containing approximately 6% saturates. The water and oil are mixed together to provide a feed stream to the hydrolysis bioreactor and an emulsion is formed using a small amount of a food grade surfactant.

The hydrolysis of the triglyceride may be effected in any convenient manner, preferably through the use of a lipase enzyme. Any of the lipase enzyme sources described or referred to herein may be employed. An enzyme that has been found to be useful in achieving substantially complete hydrolysis is *Candida cylindracae*. Typically the hydrolysis reaction is carried out at a temperature of between about 0° C. and about 120° C. at atmospheric pressure.

Under the conditions described herein, and depending on the residence time, the product stream exiting the hydrolysis bioreactor is a mixture of between about 1.5% and about 90% free fatty acids, between about 0.2 and about 10% glycerol, and between about 0% and about 99% water. Typically the product stream contains between about 0% and about 5% glycerides. The glycerides may be separated from the product stream after removal of glycerol/water, by using membranes extraction, chromatography or other separation methods.

The next step in the process is the separation of the mixture of free fatty acids from the glycerol and water. As shown in FIG. 13, this separation may take place in a water wash/centrifuge 14 which results in separation of the lighter weight glycerol and water from the heavier free fatty acids providing two product streams for further processing.

The glycerol and water stream, which may contain between about 0% and about 2% free fatty acids, is further processed by any convenient technique to separate the water. Suitable methods include distillation, membrane separation, etc. The separation should be sufficiently complete such that the glycerol stream contains only traces of water. As shown in FIG. 13, it is contemplated that the separation of glycerol and water be done in two steps, a first gross separation of water by distillation or membrane separation in a suitable separating apparatus 16 providing a glycerol enriched stream containing between about 10% and about 99% water, which is then dried, for example by use of a molecular sieve in a dryer 18, to provide a purified glycerol stream containing 99+% glycerol.

The mixture of free fatty acids exiting the centrifuge 14 contains between about 0% and about 1% water plus glycerol, and between about 0% and about 1% of glycerides. These impurities are removed by using a desiccant such as a molecular sieve. The mixture of fatty acids is then introduced into a suitable separator 20 wherein the desired free fatty acids are separated from the saturated free fatty acids. Any one of a number of separation processes may be utilized, including vacuum distillation, molecular distillation and crystallization, to obtain any desired free fatty acid stream, for example, a fatty acid stream containing 99% free fatty acids.

It is also possible to separate the desired free fatty acids by urea adduction described herein, or by the use of cyclodextrins, Trends in Biotechnology, July 1989, Vol. 7, No. 7, p. 170 by Juzset Szejtli and Szejtli et al., 1979, (Acta Chim. Acad. Sci Hnng.), 99, 447–552. The zeolite membrane separation technique described herein may also be used.

The desired free fatty acids and purified glycerol are then mixed together in a desired ratio in mixer 22 and introduced into an esterification bioreactor where the triglyceride is reformed with substantially all desired fatty acid sidechains. For example, if a 99% unsaturated free fatty acid stream is used, the triglyceride will contain less than about 1% saturated fatty acids. As shown in FIG. 13, the esterification may take place in a series of bioreactors 24 separated by or mixed within suitable driers 26, for example molecular sieve columns, which remove the water by-product produced during esterification. Water may also be removed by operating the reactor under a vacuum. In preferred embodiments, a subcritical liquified gas phase (or a supercritical carbon dioxide phase) may be conducted counter-current to the glyceride phase in the enzyme reaction zone, as generally described herein. The subcritical liquefied gas phase, which may also utilize a hydrogen-bonding co-solvent for water, as previously described (e.g., 1 weight percent ethanol), is introduced into the reaction zone in a region of relatively high ester concentration and is withdrawn from the reaction zone in a region of relatively low ester concentration. The water is separated from the withdrawn liquefied gas by methods such as distillation of the liquified gas and use of drying agents such as molecular sieves or hygroscopic adsorbents such as anhydrous calcium sulfate. The dried gas is recycled into the reaction zone.

If desired, make up free fatty acids may be admixed with the free fatty acids flowing from the separator 14 to provide a particular combination of chain lengths. For example, unsaturated free fatty acids having intermediate chain lengths ($C_8$–$C_{10}$) or ($C_8$–$C_{16}$) may be introduced in desired ratios to provide particular end use products.

A non-specific lipase such as *Candida cylindracae* can be used to effect esterification in order to achieve randomization of the fatty acid distribution. However, by having selective enzymes in different reaction subzones and controlling the fatty acid reactants introduced into the different subzones, selective glycerides may be prepared.

Figure 4:
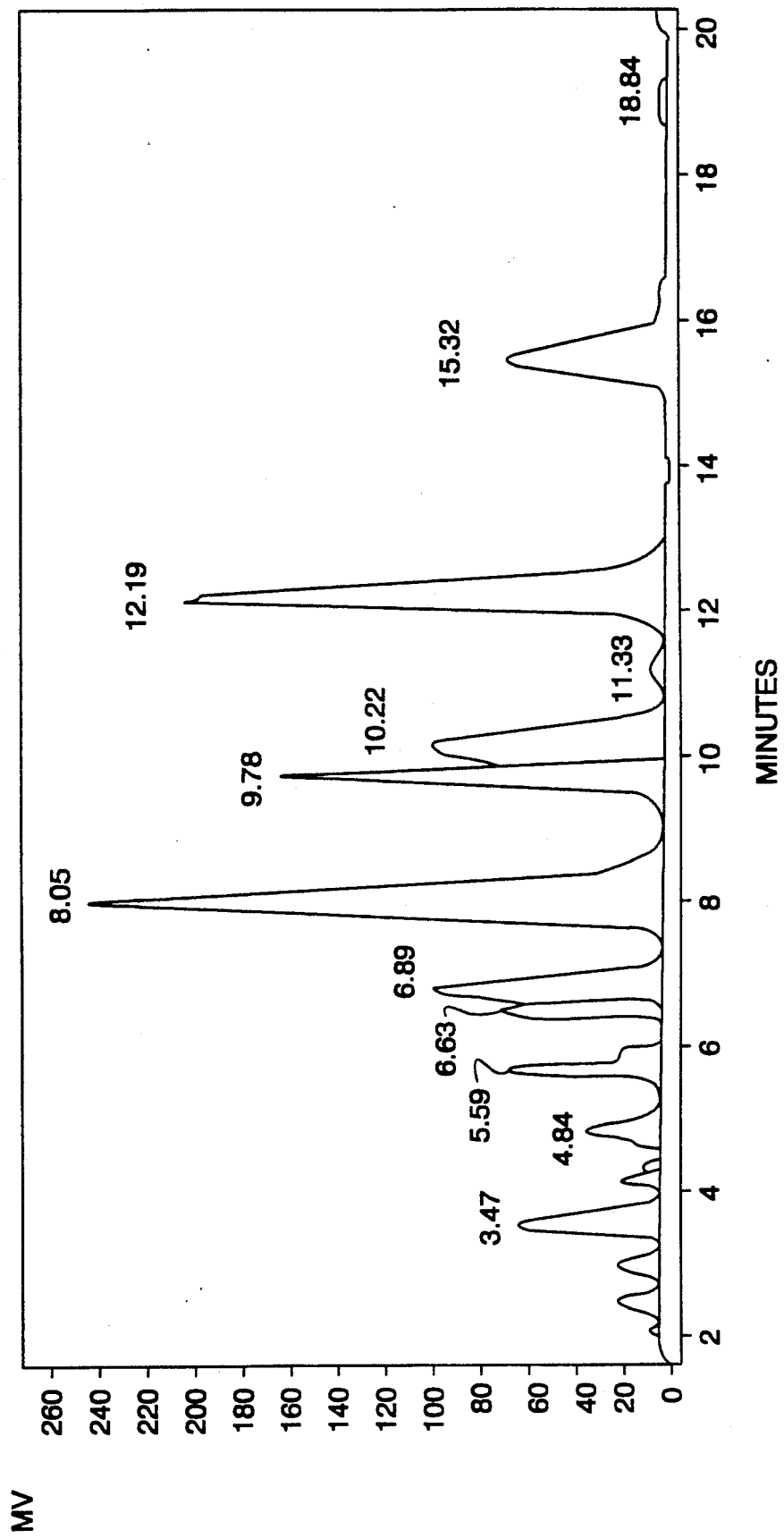
FIG. 4 is a high pressure liquid chromatographic elution chart representing the triglyceride composition of a margarine oil in accordance with the present invention prepared from the soybean oil of FIG. 3.
Figure 14:
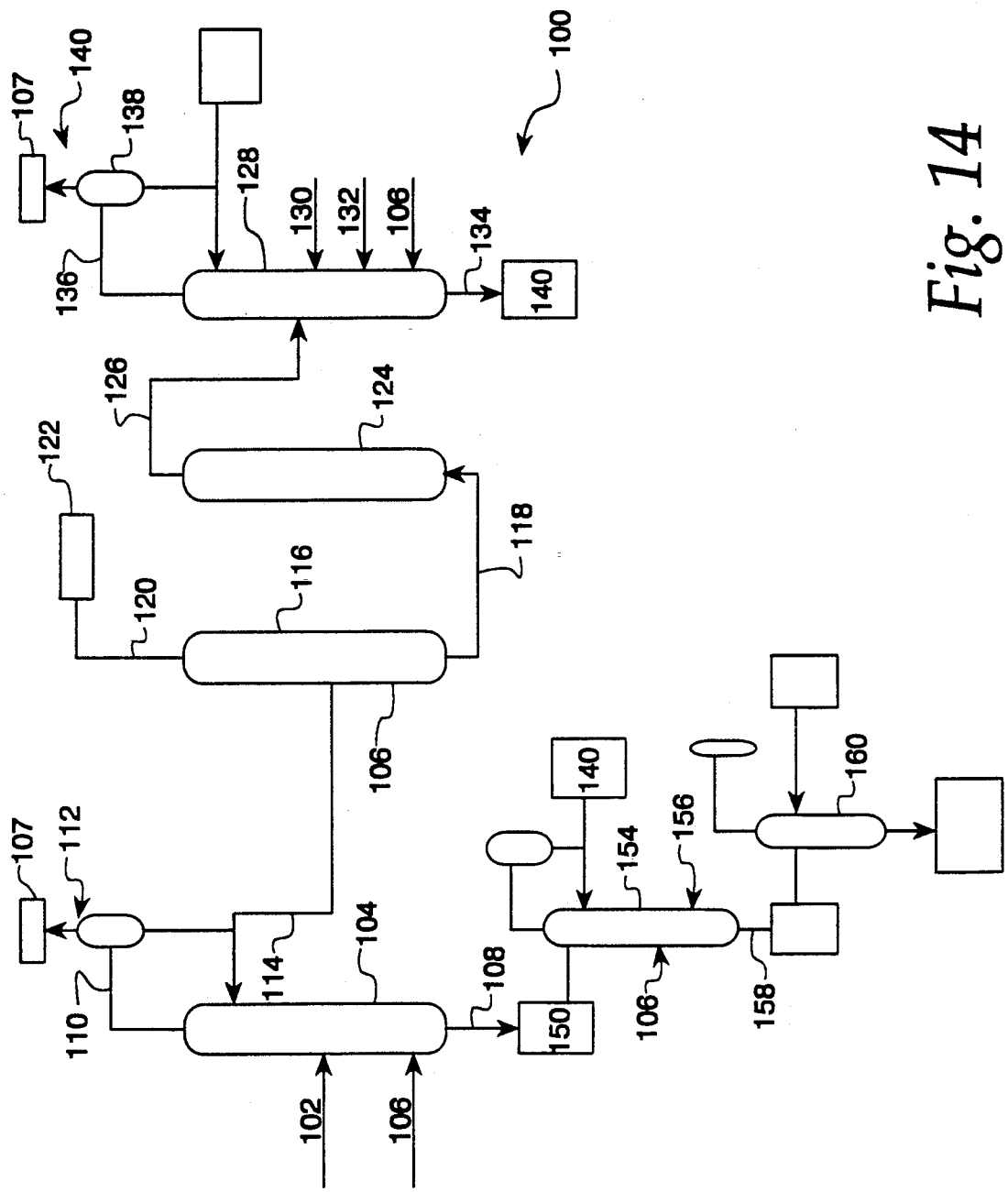
FIG. 14 is a schematic illustration of yet another embodiment of the present invention.

Illustrated in FIG. 14 is an integrated processing system 100 for refining and transesterifying vegetable, marine and/or animal fats and oils, utilizing subcritical liquified gas such as propane, propane/ethane mixture, fluorocarbons, etc., as described herein, which incorporates a variety of processing methods. By combining counter-current transesterification processing with subcritical solvent oil refining, the liquified subcritical gas solvent recovery steps and equipment costs are minimized. In order to simplify the Figure, liquefied gas recycle stages are not shown in detail, but may be provided as described herein. In this regard, as illustrated in FIG. 4, a crude vegetable oil 102 such as canola oil or soybean oil is introduced into a fractionation refining column 104, together with subcritical liquified gas 106, such as propane or an ethane/propane mixture. [H. J. Passino, *The Solexol Process, Industrial and Engineering Chemistry*, pp. 280–287, February 1949; E. B. Moore, *Decolorization of Tallow by Liquid-Liquid Extraction with Propane*, J. Amer. Oil Chem. Soc., 27, pp. 75–80, 1950, incorporated herein by reference]. The column 104 is operated under two phase conditions of temperature and liquified gas solvent/oil ratio such that substantially all of the triglycerides remain dissolved in the light phase, but high molecular weight color bodies and other non triglyceride materials, which are relatively insoluble in the subcritical liquid gas solvent, are discharged from the column 104 as a heavy phase stream 108 constituting 1–3 weight percent of the crude oil 102.

The light phase stream 110 containing substantially all of the triglycerides may be discharged from the column 104 to a reflux system 112 (e.g., as previously described), which may also reduce the solvent concentration of the triglyceride stream 110 with excess subcritical solvent sent to solvent recovery system 107, to provide a stream 114 for introduction into counter-current fractionation column 116. Column 116 is operated under two-phase, temperature (higher than column 104) and counter-current subcritical solvent ratio conditions under which substantially all of the triglyceride components are present in the heavy phase 118, which is discharged from the bottom of the column 116. Relatively low molecular weight components including unsaponifiable oil components, free fatty acids and tocopherols are present in a small fraction of light phase 120, constituting about 0.5 to 2 weight percent of the crude oil 102, which is discharged to recovery system 122. Antioxidants may be introduced into the refined oil stream to increase enzyme life. The triglyceride oil stream 118 is conducted through refining and extraction column 124 which may contain zones of bleaching clay, activated carbon, and water-saturated ion-exchange resin to remove natural, oil color compounds and any enzyme poisons, and to saturate or provide the stream with a relatively low water content (e.g., 0.1 to 0.4 weight percent), producing enzyme-conditioned, refined triglyceride stream 126 which is introduced into counter-current transesterification reactor 128. The reactor 128 is operated under two-phase subcritical solvent conditions, and contains a lipase or esterase transesterification enzyme, as generally previously described. As previously discussed, when the critical temperature of the subcritical liquefied gas is slightly above the optimum efficiency temperature for the selected lipase or other enzyme in the reactor 128, the reactor may desirably be a gravity-flow column containing the immobilized enzyme. Ethane/propane mixtures, and fluorocarbon gases having an effective critical temperature in the range of about 65°–75° C., are desirable in such systems for use with immobilized enzymes having an optimum operating temperature in the range of about 45°–65° C. If it is desired to use a liquefied gas such as propane near its critical temperature for optimizing component separation, with an enzyme not having thermal stability at that temperature, the reaction mixture may be conducted through cooled enzyme reaction zones distributed along a counter-current column which establishes the reaction component gradients. In addition, a cascaded system using counter-current feedback to multiple stages each having a cooled enzyme reaction zone and an elevated temperature centrifugal separation zone, may also be used, as indicated hereinbelow. The appropriate fatty acid or fatty acid monoester 130 is introduced into the column 128 downstream (with respect to the heavy triglyceride phase in the reactor) of the point of triglyceride stream 126. For example, in the production of a 1,3 stearoyl, 2-unsaturated fatty acid triglyceride for use as chocolate or confectionery fat, substantially pure (e.g., 98 percent by weight pure) stearic acid or ethyl stearate 130 may be introduced. In the production of a very low saturate triglyceride, a substantially pure (e.g., 98% by weight pure) unsaturated fatty acid 130 is introduced.

The transesterification reaction in the counter-current enzyme reactor 128 may also produce an amount of diglycerides and a very small amount of monoglycerides in view of the water which is present in the reaction mixture and/or the enzyme or its support. A fatty acid anhydride 132 may be introduced counter-currently downstream (with respect to the heavier triglyceride phase in the reactor 128) in a molar ratio of about 0.5:1 to about 2:1 to the diglyceride content of the reaction mixture in the absence of the acid anhydride 132 introduction. The fatty acid anhydride (e.g., stearic anhydride or aceto-stearic anhydride) for a cocoa butter substitute process;, oleic anhydride or aceto-oleic anhydride for an unsaturated oil product is utilized by the enzyme to esterify hydroxyl groups of mono- and diglycerides, while releasing a free fatty acid, to produce an enzymatically transesterified oil product having low mono- and diglyceride content. Short chain fatty acid anhydrides as $C_1$-$C_6$ anhydrides may also be used to introduce short chain fatty acids into the glyceride ester. The transesterified oil is stripped of free fatty acid in the bottom portion of the column 128, and is discharged as the heavy output phase stream 134 to a subcritical solvent recovering system 136 where the subcritical solvent is recovered for recyclic use, and the oil may be steam/vacuum stripped/deodorized and discharged as a finished product.

The light phase, which preferentially contains the counter-current fatty acid stream and some mono- and diglycerides, is discharged as light phase overhead stream 136 to a recycle reflux system 138 and to an overhead component fractionation and recovery system 140. The system 140 may be any suitable system, depending on the components, for component separation, such as those previously described.

For a cocoa butter substitute process, the system 140 may separate the fatty acids from triglycerides, hydrogenate the unsaturated fatty acids, and desirably separate the palmitic and lower molecular weight components from the mixture as previously described to provide a stearic acid recycle stream 130. For an unsaturated oil process, the saturated fat components may be separated as previously described to provide an unsaturated fatty acid recycle stream 130, which may also contain unsaturated mono-, di- and triglycerides. The system 140 may operate under pressure without removing the subcritical liquified gas solvent (e.g., freeze fractionation or liquid-liquid column separation treatment) or may remove the solvent before separation processing.

Transesterification and esterification synthesis methods may also be used to process phospholipids in accordance with the present disclosure. In this regard, for example, as indicated, hereinabove, the phosphatide-containing components of the crude vegetable oil are discharged as heavy process stream 108 from the refiner column 104. The phosphatide stream may be separated from the other components in a refiner 150 by conventional procedures to produce a pure phosphatide stream 152 containing about 0.1 to 0.4 weight percent water, which is introduced into a counter-current reaction column 154 containing an immobilized phospholipase $A_2$ enzyme, which acts at the 2-position of the phospholipids. A polyunsaturated fatty acid such as eicosapentanoic acid (EPA), docosahexanoic acid (DHA), alpha linolenic acid, gamma linolenic acid and/or conjugated linoleic acid (CLA) is introduced as a fatty acid counter-current reactant stream 156 to the reactor column 154, which operates in a similar manner to the previously described counter-current lipase reactors, to produce a phospholipid containing heavy output stream 158 containing a 2-substituted phospholipid having the polyunsaturated fatty acid in the 2-position. The 2-substituted phospholipid may be used as a functional food ingredient directly, or may be subsequently selectively hydrolyzed in reactor 160 using an immobilized phospholipase C enzyme to produce a 1-diglyceride, followed by enzymatic esterification as described herein to produce a triglyceride product having a 2-substituted polyunsaturated fatty acid component. By selecting starting materials and reactants, the 1-, and 3- positions may be saturated fatty acids such as stearic acid flanking the polyunsaturated fatty acid in the triglyceride, in order to provide increased oxidation stability to triglycerides, which may be used as a food component.

While various counter-current enzyme reactor systems have been described as counter-current enzyme reaction columns, it is also noted that counter-current cascade systems such as described herein with respect to cholesterol removal systems, may be used to achieve counter-current, multi-phase efficiency, particularly where interstage cooling is necessary between the enzyme reactor zone, and the 2-phase centrifugal separation zones, to accommodate the lipase enzyme stability temperature range. Such cascade systems may use centrifugal separators between continuous flow enzyme reactors, with the centrifugal separators being rotating separators, or non-rotating cyclone separators, to separate heavy from light phases. For example, with reference to FIG. 13, a multistage counter-current cascade system for interesterification, esterification or transesterification may be provided in which a cooled enzyme reaction zone is provided immediately following each of the pump and mixer/homogenizer stages. After exiting the enzyme reaction zones, the mixture is heated to the optimum phase separation temperature and centrifugally separated into heavy and light factions which are processed in a counter-current manner, in accordance with the principles described herein.

51587

During the course of an interesterification reaction, intermediate streams are produced which may be purified for further use in the system. One such stream contains the partially hydrolyzed triglyceride product containing between about 2% and about 20% mono- and diglycerides and between about 50% and about 80% free fatty acids. Another stream contains a mixture of saturated and unsaturated free fatty acids. It is desirable to separate the triglycerides from the mono- and diglycerides and free fatty acids. Similarly, it is desirable to separate the unsaturated and saturated free fatty acids. There are many possible means of accomplishing these separations, e.g. chromatographic (adsorption) processes, solvent extraction, vacuum distillation, selective crystallization, etc., but these processes may have deficiencies of high cost, difficulty of implementing continuous operation, difficulty of recovering elution or extraction solvents, etc. It has been found possible to continuously separate these streams using a zeolitic membrane which overcomes the problems and difficulties of alternative processes.

A commercially available zeolitic membrane (Suzuki Laboratories) is prepared by hydrothermal in-situ crystallization of zeolite (e.g. Na faujasite) on a porous (20A) Vycor 7930 support. The membrane is in the form of a 12" tube contained within an annular chamber.

EXAMPLE 1

Zeolite used for tube construction is preferably Na-ZSM-5. A stream containing 1:1 (wt) . Triacylglycerols (TAG) and free fatty acids (FFA) are passed continuously into the lumen of the tube while vacuum is applied to the annulus, with a cold trap. The liquid collected in the cold trap is essentially pure FFA. Operation of this apparatus in continuous recycle mode results in virtually complete separation of the TAG and FFA.

EXAMPLE 2

Zeolite used for tube construction is preferably Fe-ZSM-5. A stream containing 95:5 (wt ratio) unsaturated free fatty acids (UFFA) to saturated free fatty acids (SFFA) are passed continuously into the lumen of the tube while vacuum is applied to the annulus, with a cold trap. The liquid collected in the cold trap is essentially pure SFFA. operation of this apparatus in continuous recycle mode results in virtually complete separation of the SFFA and UFFA.

EXAMPLE 3

Apparatus similar to examples (1) and (2) except instead of vacuum applied to the annulus, pressure of 25-200 psig is applied to the lumen side.

EXAMPLE 4

Apparatus similar to examples (1) and (2) respectively, but instead of vacuum applied to the annulus, a sweep solvent is passed through the annulus. This solvent has high solvency for FFA, e.g. acetone, and differential pressure is maintained on the lumen side to minimize flux of solvent from the annulus to the lumen.

51585

The disclosed processes may be employed to introduce specific types of fatty acids into triglycerides. One example of this is the introduction of medium chain lengths fatty acids ($C_8$–$C_{12}$) into triglycerides rich in linolenic and oleic acids to provide a fat source for food products that is more easily metabolized by certain segments of the population that are unable to metabolize fats having all or a majority of long chains, i.e., $C_{16}$ and above, fatty acids.

Ideally, the triglyceride raw materials are high in unsaturated oleic and linoleic fatty acids at the 2-position. Examples of such triglycerides include high oleic sunflower oil, high linoleic safflower oil, canola oil and soybean oil.

The medium chain length fatty acids may be provided by naturally occurring oils such as cuphea oil (85% $C_{10}$ fatty acids) or by purified fatty acids having the desired $C_8$–$C_{12}$ chain length. The esterification is desirably carried out using a 1,3 specific lipase as described herein in order to provide a triglyceride product having a predominance of long chain unsaturated fatty acids, i.e., oleic and linoleic, at the 2-position and medium chain length fatty acids at the 1- and 3-positions.

In an example of this process, soybean oil having a fatty acid distribution of 52% linoleic acid and 22% oleic acid with the 2-position comprising 70% linoleic acid and 23% oleic acid was interesterified in a 1:1 ratio with a $C_{10}$ saturated fatty acid in hexane solvent in the presence of Novo IM20 lipase catalyst. The reaction was carried out at 40° C. with stirring for hours. After separation of the enzyme and solvent, the resulting triglyceride had a fatty acid distribution as follows:

| Fatty Acid Distribution (wt. %) | |
| --- | --- |
| $C_{10}$ | 36.1% |
| $C_{16}$ | 3.8% |
| $C_{18:0}$ | 1.5% |
| $C_{18:1}$ | 14.4% |
| $C_{18:2}$ | 38.4% |
| $C_{18:3}$ | 3.9% |
| Other | 1.9% |

50194

Yet another example of a tailored synthetic triglyceride that may be prepared in accordance with the disclosed processes is a triglyceride containing conjugated linoleic fatty acid residues. Conjugated linoleic acid (CLA) is believed to possess anti-carcinogenic activity, possibly acting as an antioxidant. It would be desirable to introduce the anticarcinogenic properties of conjugated linoleic acid into triglycerides used in foods and as cooking fats.

The conjugated linoleic acid may be interesterified with naturally occurring triglycerides, for example the soybean, canola, sunflower and safflower oils described herein, or with synthetic triglycerides.

One such triglyceride is that which results from the interesterification of triolein and conjugated linoleic acid in the presence of a 1,3 specific lipase. 2.0 grams of triolein and 1.0 grams of conjugated linoleic acid are dissolved in hexane solvent and 1.0 grams of NOVO IM 20 1-, 3- specific lipase are added. The interesterification reaction is carried out at 40° C. with stirring for 24 hours. After separation of solvent and enzyme, a triglyceride product is obtained having a fatty acid distribution as follows:

| Fatty Acid Distribution (wt. %) | |
| --- | --- |
| CLA | 27% |
| $C_{18:1}$ | 73% |

51588

Another example of the preparation of an engineered triglyceride having specified desirable properties, particularly when the triglyceride is intended for use in food products, is the preparation of a triglyceride having furan containing fatty acid side chains. Fatty acids containing a furan ring are described by Gorst-Allman et al., *Lipids,* Vol. 23, No. 11, pp. 1032-6 (1988). These naturally occurring fatty acids are only metabolized about 30% as compared to the fatty acids found in naturally occurring triglycerides. Esterification processes, as disclosed herein, may be used to introduce furan fatty acids into triglycerides. Such triglycerides will have a reduced caloric content, as compared to natural triglycerides, and find use in reduced calorie foods.

Having generally described various aspects of the present low saturate vegetable oil products and methods which may be utilized to prepare such products, the invention will now be more particularly described with respect to the following specific examples. Unless otherwise noted, all percentages are by weight. All references cited herein are specifically incorporated by reference.

EXAMPLE 1

Soybean oil (SBO) was converted into a stick margarine oil product which has a similar solid fat index/melting temperature profile to that of a conventional stick margarine oil product, and a smooth organoleptic characteristic. This was done by interesterifying soybean oil with stearic acid, in a two step process, using NOVO IM 20 Lipase, a *Mucor miehei* immobilized lipase, which is 1-, 3- positionally specific, supplied by NOVO Laboratories, Inc., such as described in European Patent 0140542. The fatty acid distribution of the five major fatty acids of the starting soybean oil was as follows:

TABLE 1

|  | Weight Percent Fatty Acids in Position | | |
|---|---|---|---|
|  | 1,2 + 3 | 2 | 1 + 3 |
| Palmitic (P) | 10.4 | 0.73 | 15.24 |
| Stearic (S) | 4.2 | 0.30 | 6.15 |
| Oleic (O) | 22.01 | 23.03 | 21.50 |
| Linoleic (L) | 52.11 | 69.49 | 43.42 |
| Linolenic (Ln) | 6.0 | 6.45 | 5.78 |

In a first step, 73 grams of a commercial stearic acid product which was 94.0% stearic acid and 4.2 weight percent palmitic acid (Aldrich) was mixed with 157.2 grams of the liquid soybean oil, calculated to provide a final stearic acid concentration of 28.9 weight percent, equivalent to 43.4 weight percent stearic acid in the 1+3 positions.

The reaction was carried out in a hexane solvent system and utilized 0.625 grams of Novo lipase (containing 3.0-11.0 weight percent of water) per gram of oil. The reaction mixture was incubated at 40° C. in a stirred reaction vessel at 250 rpm for 48 hours to assure full equilibration. To stop the reaction, the lipase was removed via filtration and the hexane solvent distilled off. The free fatty acids were removed by distillation at less than 1.0 mm Hg at a temperature of 500° F. A second reaction was subsequently carried out in the same manner using the transesterified, distilled oil from the first step reaction, using the same stoichiometry, calculated to give a second step reaction product having final theoretical stearic acid concentration of about 45 weight percent.

The following table shows the Fatty Acid Distribution (FAD) in weight percents of the respective first and second step products and the Solid Fat Index (SFI) of the second step product after hexane fractionation compared to a conventional stick margarine oil:

TABLE 2

| FAD % | 1st Step Product | 2nd Step Product | 2nd Step °C. Oil | Conventional Product | Stick Margarine |
|---|---|---|---|---|---|
| Palmitic Acid (P) | 7.6 | 5.7 | 10.0 | 29.0 | 28.3 |
| Stearic Acid (S) | 27.1 | 45.0 | 21.1 | 21.2 | 15.3 |
| Oleic Acid (O) | 16.7 | 12.7 | 26.7 | 5.0 | 8.5 |
| Linoleic Acid (L) | 41.4 | 33.1 | 33.3 | 1.4 | 2.3 |
| Linolenic Acid (Ln) | 5.7 | 4.2 SFI | 37.8 | 0.5 | 0.0 |

EXAMPLE 2

Further enzymatic interesterification reactions between soybean oil and stearic acid were carried out as described in Example 1. Samples were withdrawn periodically and analyzed by HPLC. A rapid HPLC analysis for triglycerides was implemented. The HPLC conditions are summarized below:

Column: C-18 (Alltech) Adsorbosphere 4.6×250 mm, 5 micron
Mobile Phase: 70:30 Acetone-Acetonitrile
Flow Rate: 2 mL/min.
Temperature: 40° C.
Detector: Refractive Index (Waters 401)

A chromatogram of a sample of soybean oil is illustrated in FIG. 3. The respective component peaks are identified by their respective retention times, in minutes. The corresponding weight percents of the components as shown in FIG. 3 are as follows:

TABLE 3

| Peak Compound | Retention Time | Weight Percent |
|---|---|---|
| LLLn | 4.83 | 9.8 |
| LLL | 5.51 | 25.2 |
| OLL | 6.53 | 14.3 |
| PLL | 6.73 | 16.4 |
| OOL | 7.91 | 7.5 |
| PLO | 8.14 | 14.0 |
| POO | 9.93 | 10.3 |
| SLS | 12.20 | 2.6 |

Triglycerides in soybean oil were identified, along with product TAGs from an interesterification reaction of soybean oil with stearic acid, through the use of standard oils with known TAG composition. Mixed standards were also produced by the interesterification of standard TAGs, such as LLL, with stearic and palmitic acids. When most of the significant TAGs were identified and their retention times on the HPLC column were noted, data on the enzyme reaction was gathered. FIG. 4 is an HPLC chromatogram of soybean oil which has been transesterified with stearic acid. As in FIG. 3, the respective component peaks are identified by their respective retention times. The corresponding weight percentages of the components, as shown in FIG. 4 are as follows:

TABLE 4

| Peak Compound | Retention Time | Weight Percent |
|---|---|---|
| Unknown | 3.47 | 5.5 |
| LLLn | 4.84 | 2.3 |

TABLE 4-continued

| Peak Compound | Retention Time | Weight Percent |
|---|---|---|
| LLL | 5.59 | 6.8 |
| OLL | 6.63 | 3.3 |
| PLL | 6.89 | 6.6 |
| SLL | 8.05 | 21.4 |
| SLO | 9.78 | 11.5 |
| SLP | 10.22 | 9.5 |
| Unknown | 11.33 | .23 |
| SLS | 12.19 | 26.4 |
| SOS | 15.32 | 7.8 |
| Unknown | 18.84 | .48 |

By quantitatively following the disappearance of certain TAGS, such as LLL, from the initial soybean oil, or the production of certain TAGS, such as SLL or SLS, classical kinetic data was obtained and used to design a single step reaction using an increased level of transesterification enzyme, and a reduction in reaction time from 96 to 6 hours, as described in the following example.

EXAMPLE 3

A single step reaction using increased levels of enzyme, was carried out having a decreased reaction time of 6 hours. The downstream separation processing of the interesterified oil was aided out by fractional crystallization of the free fatty acids from the reaction mixture. This also increased product yield. To provide the desired composition, 180 grams of stearic acid reagent was added to 157.2 grams soybean oil.

The reaction was set up in a hexane solvent system which consisted of 2.5 ml hexane per gram of reactants. For this example, 0.375 grams of NOVO IM 20 Lipase product (a *Mucor miehei* immobilized 1-, 3- specific lipase) was used per gram of oil.

The reaction was incubated for 6 hours at 40° C. in a stirred reaction vessel at 250 rpm.

A large excess of stearic acid was utilized in this batch mode reaction to achieve the desired degree of substitution of stearic acid in the triglyceride end product. In order to improve the economics of the process, and to prevent the formation of undesirable trisaturates during subsequent distillation or deodorization procedures, the excess stearic acid should be removed and recovered from the reaction mixture, prior to high temperature treatment. This was done by selective crystallization of the stearic acid from the reaction mixture. To accomplish this, the mixture was filtered to remove the enzyme, which was then washed with hexane to remove any absorbed fat. The washings and filtrate were combined and concentrated to about 70 percent of the original reaction volume. The concentrated solution was allowed to stand for 8 hours at 20° C., then at 4° C. for 16 hours, which produced a crystalline precipitate of saturated fatty acid. The large crystalline mass was broken up, slurried with cold hexane and vacuum filtered. The crystals were washed a total of four times, with an equal volume of cold hexane each time, to remove fat. The combined washings were distilled to remove hexane and the fat was then subjected to deodorization. The crystals were then dried under vacuum and analyzed. The FAD and glyceride analyses of the crystals are shown in Tables 5 and 6.

TABLE 5

FAD Analysis of Recovered Fatty Acid Crystals

| | Fatty Acid | % |
|---|---|---|
| | C12 | <0.1 |
| | 12:0 | <0.1 |
| | 12:1 | <0.1 |
| | 13:0 | <0.1 |
| | 13:1 | <0.1 |
| | 14:0 | <0.1 |
| | 14:1 | <0.1 |
| | 15:0 | <0.1 |
| | 15:1 | <0.1 |
| P | 16:0 | 3.7 |
| | 16:1 | <0.1 |
| | 17:0 | 0.9 |
| | 17:1 | <0.1 |
| S | 18:0 | 92.2 |
| O | 18:1 | 0.8 |
| | 18:1 trans | <0.1 |
| L | 18:2 | 1.4 |
| | 20:0 | 0.2 |
| Ln + | 18:3 + 20:1 | 0.2 |
| | 20:2 | <0.1 |
| | 20:3 | <0.1 |
| | 22:0 | 0.2 |
| | 22:1 + 20:4 | <0.1 |
| | 24:0 | <0.1 |
| | 24.1 | <0.1 |
| | Unknown | 0.1 |

TABLE 6

Analysis of Recovered Fatty Acid Crystals

| Fatty Acid | Mono-glycerides | Diglycerides | Triglyceride Carbon Number (total) | | | | |
|---|---|---|---|---|---|---|---|
| | | | 48 | 50 | 52 | 54 | 56 | 58 |
| 94.3 | 0.1 | 2.9 | — | — | 1.0 | 1.7 | — | — |

The overall recovery of stearic acid in the crystallization step, accounting for exchange, was 88.7% of the theoretical value.

The reaction product was processed in a manner similar to that of the two step process of Example 1. The fatty acid distribution and solid fat indices, respectively, of the reaction product as compared to a conventional stick margarine oil, were as follows:

TABLE 7

Fatty Acid Distribution

| FAD % | One Step Product | Conventional Stick Margarine Oil |
|---|---|---|
| P 16:0 | 5.9 | 11.6 |
| S 18:0 | 40.1 | 7.4 |
| O 18:1 | 14.7 | 34.1 |
| L 18:2 | 34.1 | 7.6 |
| Ln 18:3 | 4.1 | 0.2 |
| Total Trans | 1.9 | 33.2 |

TABLE 8

Solid Fat Index

| SFI °C. | One Step Product | Conventional Stick Margarine Oil |
|---|---|---|
| 10.0 | 28.7 | 28.3 |
| 21.1 | 21.8 | 15.3 |
| 26.7 | 8.5 | 8.5 |
| 33.3 | 2.4 | 2.3 |
| 37.8 | 1.9 | 0.0 |

To test the feasibility of reusing the recovered stearic acid in subsequent reactions, a test was set up in which recovered stearic acid was used for a one stage transesterification reaction as described hereinabove. Analyses of this particular batch of stearic acid crystals indicated that the material was 86.5 weight percent free fatty acids, of which 89.9 weight percent was stearic acid, and approximately 10.1 weight percent of mono-, di- and triglycerides. The amount of stearic acid added to the reaction mixture was adjusted to account for the amount of stearic acid present in the recycled acid. SFI, FAD and glyceride analyses on the transesterified product indicate that it is essentially the same as control batches. These results can be seen in Tables 9 through 11.

TABLE 9

SFI Analysis of Transesterified Soybean Oil Produced Using Recovered Stearic Acid

| Weight percent solids | Temperature |
|---|---|
| 29.9 | 10.0° C. |
| 29.7 | 10.0° C. |
| 21.2 | 21.1° C. |
| 21.0 | 21.1° C. |
| 6.3 | 26.7° C. |
| 6.4 | 26.7° C. |
| 2.5 | 33.3° C. |
| 2.4 | 33.3° C. |
| *2.2 | 37.8° C. |
| 2.2 | 37.8° C. |

*(Values are slightly high due to SSS formed during deodorization)

TABLE 10

FAD Analysis of Transesterified Soybean Oil Produced Using Recovered Stearic Acid

| | Fatty Acid | % |
|---|---|---|
| | C12 | <0.1 |
| | 12:0 | <0.1 |
| | 12:1 | <0.1 |
| | 13:0 | <0.1 |
| | 13:1 | <0.1 |
| | 14:0 | 0.1 |
| | 14:1 | <0.1 |
| | 15:0 | <0.1 |
| | 15:1 | <0.1 |
| P | 16:0 | 5.0 |
| | 16:1 | 0.1 |
| | 17:0 | 0.2 |
| | 17:1 | <0.1 |
| S | 18:0 | 41.9 |
| O | 18:1 | 13.9 |
| | 18:1 trans | <0.1 |
| L | 18:2 | 33.2 |
| | 20:0 and | |
| Ln + | 18:3 + 20:1 | 4.5 |
| | 20:2 | <0.1 |
| | 20:3 | <0.1 |
| | 22:0 | 0.3 |
| | 22:1 | <0.1 |
| | 24:0 | 0.1 |
| | 24.1 | 0.3 |
| | Unknown | 0.3 |

TABLE 11

Glyceride Analysis of Transesterified Soybean Oil Produced Using Recovered Stearic Acid

| Fatty Acid | Mono-glycerides | Di-glycerides | Triglyceride Carbon Number | | | | | |
|---|---|---|---|---|---|---|---|---|
| | | | 48 | 50 | 52 | 54 | 56 | 58 |
| <0.1 | <0.1 | 8.8 | 0.1 | 1.4 | 11.7 | 76.9 | <0.1 | 0.4 |

EXAMPLE 4

In order to make margarine, a ten liter reaction flask, and a temperature-controlled water bath were used to prepare a batch of transesterified margarine oil generally as previously described in Example 3. In accordance with such reaction, 700 grams of soybean oil, 800 grams of stearic acid, 262 grams of the NOVO IM 20 immobilized Lipase enzyme product and 3.75 liters of hexane were reacted to substantial equilibrium in the reaction flask. This provided a 15-fold scale up and enough transesterified oil for two batches of margarine. Analyses indicated that the fat produced in the large scale batch was substantially identical to the small scale preparations described in Example 3. The transesterified soybean oil, which had an SFI profile substantially equivalent to that of conventional stick margarine, was incorporated into both stick margarine oil and tub margarine oil formulas. These were prepared on a small scale (350 grams), in a jacketed, cooled Waring blender. The transesterified soybean oil, when incorporated into the tub margarine oil formula, demonstrated harder physical properties than the control. When transesterified soybean oil was incorporated into the stick margarine oil formula, the physical properties were similar to that of the stick margarine oil control.

The removal of free fatty acids from the interesterification reaction mixture was done by vacuum steam distillation (deodorization). The conditions of the distillation and also the concentration of free fatty acids in the reaction mixture were factors which were investigated to determine if they produced changes in the final product, both physically and chemically.

Table 12 shows the effect of free stearic acid concentration, in transesterification mixture and also of extended hold times at elevated temperatures (480° F.).

TABLE 12

| Deodorization | 15'–350° F. 60'–480° F. | 15'–350° F. 60'–480° F. | 500° F. No Hold |
|---|---|---|---|
| Conditions Hg | <0.1 mm Hg | <0.1 mm Hg | <0.1 mm |
| Sample mix | transesterification reaction mix | trans-esterification | Post trans-esterification |
| SFI 0° C. | | | |
| 10.0 | 32.2 | 28.1 | 27.2 |
| 21.2 | 21.7 | 17.3 | 21.6 |
| 26.7 | 17.0 | 12.3 | 9.0 |
| 33.3 | 11.1 | 7.4 | 0.0 |
| 37.8 | 9.5 | 5.8 | 0.0 |
| % SSS | 4.2 | 2.6 | 0.0 |
| Free Fatty Acids | 0.3 | 0.02 | 0.3 |

At higher stearic acid concentrations, tristearin (SSS), is produced and increases the melting solids at 37.8° C. This table also shows that at extended hold times, SSS is produced. These results indicate that in the presence of a high concentration of stearic acid (30%) or when the deodorization is held at 480° F. for 1 hour, undesirable non-enzymatic interesterification may occur during deodorization producing high melting tristearin which adversely affects the mouthfeel of the product. It is therefore necessary to remove, in a suitable manner such as via crystallization, the bulk of the stearic acid remaining in the reaction mixture prior to deodorization to avoid formation of undesirable tristearin.

Accordingly, in accordance with the present invention, it will be appreciated that improved margarine oils have been provided which have low trans- acid content, together with smooth, organoleptic mouthfeel characteristics and desirable melt characteristics. While the invention has been described with respect to certain specific embodiments, it will be appreciated that various modifications and adaptations will be apparent from the present disclosure, and are intended to be within the scope of the following claims.

EXAMPLE 4A

Soybean oil was interestified with behenic acid, in a one step process, using NOVO IM 20 Lipase, a Mucor miehei immobilized lipase, which is 1-, 3- positionally specific. The fatty acid distribution of the five major fatty acids of the starting soybean oil was as follows:

TABLE 1

| | Weight Percent Fatty Acids in Position | | |
|---|---|---|---|
| | 1,2 + 3 | 2 | 1 + 3 |
| Palmitic (P) | 10.4 | 0.73 | 15.24 |
| Stearic (S) | 4.2 | 0.30 | 6.15 |
| Oleic (O) | 22.01 | 23.03 | 21.50 |
| Linoleic (L) | 52.11 | 69.49 | 43.42 |
| Linolenic (Ln) | 6.0 | 6.45 | 5.78 |
| Behenic acid | 0.0 | 0.00 | 0.00 |

80 grams of a commercial behenic acid product which was 94% behenic acid and was mixed with 157.2 grams of the liquid soybean oil, calculated to provide a final behenic acid concentration of 28.6 weight percent, equivalent to 41.9 weight percent behenic acid in the 1+3 positions.

The reaction was carried out in a hexane solvent system and utilized 0.175 grams of Novo lipase IM20 (containing 3.0–11.0 weight percent of water) per gram of reactant. The reaction mixture was incubated at 45° C. in a stirred reaction vessel at 250 rpm for 24 hours to assure full equilibration. To stop the reaction, the lipase was removed via filtration and the hexane solvent distilled off. The free fatty acids were removed by distillation at less than 1.0 mm Hg at a temperature of 500° F.

The following table shows the Fatty Acid Distribution (FAD) in weight percents of the products

TABLE 2

| FAD % | Product |
|---|---|
| Palmitic Acid (P) | 6.2 |
| Stearic Acid (S) | 2.7 |
| Oleic Acid (O) | 16.4 |
| Linoleic Acid (L) | 37.0 |
| Linolenic Acid (Ln) | 3.5 |
| Arachidic acid (Ar) | 1.4 |
| Behenic Acid (B) | 28.9 |
| Lignoceric acid (Lg) | 0.6 |

EXAMPLE 5

Runs 1 and 2

To produce a low saturate oil, two different lots of canola oil were transesterified with oleic and linoleic acids. Transesterification reactions were carried out in 2.5 ml of hexane, per gram of reactants. NOVO IM 20 Lipase, an immobilized 1-, 3- positionally specific lipase from *Mucor miehei* as previously described, was used at a level of 0.375 gram, per gram of oil. The transesterification reactions were run in a water bath at 40° C., under 250 rpm agitation for 6 hours. The reactions were stopped by removing the immobilized lipase by filtration. The hexane was removed by distillation. The reaction mixture at this point was deodorized under a vacuum of 0.1 mm Hg to a maximum temperature of 500° F. The product was then analyzed for fatty acid distribution (FAD).

The FAD may be resolved into the five major fatty acids, palmitic (P), stearic (S), oleic (O), linoleic (L), linolenic (Ln) and all the remaining fatty acids designated as "other". A typical FAD of the fatty acid components is set forth in the following Table 1.

TABLE 1

| | Oleic Acid | Linoleic Acid |
|---|---|---|
| P | 0.51 | — |
| S | 0.17 | 0.04 |
| O | 98.46 | 0.67 |
| L | 0.27 | 98.85 |
| Ln | — | 0.06 |
| Other | 0.59 | 0.38 |

The weight of reactants used in these runs was as follows:

TABLE 2

| | Weight of Reactants (g) | Percent by weight |
|---|---|---|
| Canola oil | 157.2 | 13.58 |
| Linoleic acid | 600.0 | 51.85 |
| Oleic acid | 400.0 | 34.57 |

These amounts were selected based on a "target" transesterified composition having a weight ratio of esterified monounsaturated fatty acids to pulyunsaturated fatty acids of about 1:1. Following the reactions, the fatty acid distribution (FAD) of the products was determined, as set forth in Table 3:

TABLE 3

| % | Starting Material Canola Oil* | Target for Run 1 | Run 1 | Run 2 | Run 3 | Targets* 2 & 3 |
|---|---|---|---|---|---|---|
| P | 4.15 | 2.78 | 0.89 | 2.91 | 2.55 | 0.60 |
| S | 1.81 | 1.39 | 0.35 | 1.26 | 1.22 | 0.22 |
| O | 56.74 | 53.78 | 45.71 | 52.61 | 51.63 | 44.71 |
| L | 19.97 | 30.83 | 45.53 | 33.60 | 35.34 | 47.83 |
| Ln | 7.85 | 6.73 | 5.67 | 6.49 | 6.32 | 5.47 |
| Other | 9.39 | 4.49 | 1.82 | 3.13 | 2.94 | 1.14 |
| Total Sats ($C_{12-18}$) | 6.03 | 4.26 | 1.26 | 4.17 | 3.87 | 0.83 |

*Starting FAD and targeted FAD are data from one experiment, but are representative of all three trials Neither reaction reached its targeted equilibrium. These results suggest that there is some property of canola oil which is affecting the catalytic properties of the immobilized lipase.

Run 3

A further reaction was conducted in the same manner with 0.02% TBHQ added as an antioxidant to prevent the formation of peroxides during the reaction which might interfere with the transesterification. Also, the lipase enzyme product concentration was doubled (0.750 grams lipase per gram of oil) to compensate for any other inhibition which might be occurring. Table 3 also illustrates the FAD of the product triglycerides. Again, the targeted equilibrium was not achieved and only a slight decrease in the saturates was observed compared to Runs 1 and 2.

Run 4

Runs 1–3 indicated that there was some contaminant in the canola oil which affected the lipase activity in such a way that the reaction could not reach equilibrium under those conditions. Canola oil triglycerides were purified by Florisil column chromatography.

Canola oil was purified on activated Florisil (dried at 100° C. for 18 hours, then equilibrated to 3 weight percent water at room temperature by the addition of distilled water). A 125 ml volume of activated Florisil was equilibrated in hexane in a column of 2.5×50 centimeters. Fifty-five grams of canola oil were eluted with 3 column volumes of hexane. This fraction was collected and was found to be the triglyceride fraction. This fraction was distilled to remove the hexane and used as a source of canola oil triglycerides. These purified triglycerides were used to determine initial reaction conditions in Run 4. Run 4 was carried out in a manner substantially identical to Run 3 using the Florisil purified canola oil. Table 4 illustrates the FAD of the product triglycerides:

TABLE 4

| % | Starting Material Canola Oil* | Run #4 | Run #5 | Targets* for 4 & 5 |
|---|---|---|---|---|
| P | 4.15 | 1.05 | 1.02 | 0.60 |
| S | 1.81 | 0.58 | 0.63 | 0.22 |
| O | 56.74 | 48.16 | 47.33 | 44.71 |
| L | 19.97 | 43.48 | 42.95 | 47.83 |
| Ln | 7.85 | 4.98 | 5.67 | 5.47 |
| Other | 9.39 | 1.75 | 2.40 | 1.14 |
| Total Sats | 6.03 | 1.64 | 1.69 | 0.83 |
| Monounsats to Polyunsats | 2:1 | 1:1 | 1:1 | 1:1 |

*See Table 3

Run 4 Florisil purified canola triglycerides with 0.02% TBHQ—Run 5 canola oil with 0.02% TBHQ Run 5

Another lot of canola oil was also transesterified under substantially identical parameters as described for Run 3, including 0.02 weight percent TBHQ as an antioxidant. Table 4 also illustrates the FAD of this product. This lot did not demonstrate any lipase inhibition since the targeted equilibrium was nearly attained. Thus, the contaminant causing this inhibition is variable from lot to lot.

EXAMPLE 2

High oleic sunflower oil and high oleic safflower oil having low levels of saturated fatty acids were transesterified with substantially pure oleic and linoleic acids, substantially as described in Run 4 of Example 1. Table 5 illustrates the starting FAD, and the FAD of the transesterified products:

TABLE 5

| % | Starting Material | Transesterified Product |
|---|---|---|
| High Oleic Sunflower Oil | | |
| P | 3.71 | 0.44 |
| S | 4.15 | 0.54 |
| O | 80.86 | 47.46 |
| L | 8.92 | 49.43 |
| Ln | 0.10 | 0.21 |
| Other | 2.26 | 1.92 |
| Total Sats | 7.94 | 0.98 |
| High Oleic Safflower Oil | | |
| P | 5.35 | 0.55 |
| S | 2.26 | 0.33 |
| O | 73.15 | 47.49 |
| L | 17.25 | 50.99 |
| Ln | 0.11 | 0.05 |
| Other | 1.88 | 0.59 |
| Total Sats | 7.82 | 0.90 |

Neither oil appeared to demonstrate any inhibition of the lipase, and oils with <1 weight percent saturates were produced.

EXAMPLE 3

An oil having very low saturated fatty acid content and a 2:1:1 weight ratio of omega-9:omega-6:omega-3 fatty acids is a nutritionally desirable product which is not naturally available. Canola oil was transesterified with purified oleic, linoleic and linolenic acids as previously described for Run 4 of Example 1, with the addition of linolenic acid to the reaction mixture to prepare such a product. Table 6 illustrates these results:

TABLE 6

| % | Starting Material | Transesterified Product | Target |
|---|---|---|---|
| P | 4.15 | 1.31 | 0.59 |
| S | 1.81 | 0.79 | 0.20 |
| O | 56.74 | 49.14 | 48.02 |
| L | 19.97 | 21.81 | 24.49 |
| Ln | 7.85 | 22.05 | 25.31 |
| Other | 9.39 | 4.90 | 1.38 |
| Total Sats | 6.03 | 2.10 | 0.80 |
| Monounsats to Polyunsats | 2:1 | 1:1 | 1:1 |
| omega-9: omega-6: omega 3 | 7:2:1 | 2:1:1 | 2:1:1 |

EXAMPLE 4

In the previously described runs, the transesterified oils had a very low target amount of less than 1.3 weight percent saturated fats. To achieve this level of unsaturation in the final product a ratio of fatty acids: oil of 6.4:1 in the reaction mixture was utilized, in which the reaction mixture contained only 13.5% oil. Transesterified canola oils having about 3 weight percent saturated fats may be more economically produced using lower ratios of unsaturated fatty acids to oil in the reaction mixture. The calculations used to produce a canola oil with close to 3% saturates are shown in Table 7:

TABLE 7

| | REACTANTS | | | | | | Total | Targeted Fatty Acids | |
|---|---|---|---|---|---|---|---|---|---|
| % | Canola Oil #1–#3 157.2 g | | Linoleic Acid 90 g | | Oleic Acid 90 g | | Amount of Exchangeable Fatty Acids | at Equilibrium, Weight Percent #1 + #3 | Overall |
| P | 6.06 | + | — | + | 0.46 | = | 6.52 | 2.33 | 1.67 |
| S | 2.72 | + | 0.036 | + | 0.15 | = | 2.91 | 1.04 | 0.69 |
| O | 59.64 | + | 0.60 | + | 88.61 | = | 148.85 | 53.16 | 52.42 |
| L | 13.42 | + | 88.97 | + | 0.24 | = | 102.63 | 36.66 | 35.46 |
| Ln | 3.96 | + | 0.06 | + | — | = | 4.02 | 1.44 | 6.17 |
| Other | 14.96 | + | 0.34 | + | 0.53 | = | 14.96 | 5.34 | 3.59 |

TABLE 7-continued

|  | 280.00 | 100.00 | 100.00 |
| --- | --- | --- | --- |
|  | Weight of Reactants (g) | Percent by Weight | |
| Canola Oil | 157.2 | 46.62 | |
| Linoleic Acid | 90.0 | 26.69 | |
| Oleic Acid | 90.0 | 26.69 | |
|  |  | 100.00 | |

Product at equilibrium: 2.38% saturates (theoretical)
1.15:1 Fatty acids:Oil

Theoretically, it should be possible to produce a canola oil having less than or about 3 weight percent saturates with a fatty acid:oil ratio of 1.15:1, assuming the fatty acid feedstock has a saturate level of 0.72 weight percent or less.

Canola oil (Kraft Food Ingredients Group) was transesterified using the procedure of Run 3, Example 1, with the proportion of reaction components as described hereinabove. The results from two trials were tabulated in Table 8:

TABLE 8
FAD'S OF Transesterified Canola Oil Products

| % | Starting Material Canola Oil | Run #1 | Run #2 | Target |
| --- | --- | --- | --- | --- |
| P | 4.15 | 1.86 | 1.71 | 1.67 |
| S | 1.81 | 1.14 | 1.07 | 0.69 |
| O | 56.74 | 53.12 | 52.58 | 52.42 |
| L | 19.97 | 33.35 | 34.27 | 35.46 |
| Ln | 7.85 | 5.58 | 5.03 | 6.17 |
| Other | 9.39 | 4.95 | 5.34 | 3.59 |
| Total Sats | 6.03 | 3.00 | 2.78 | 2.38 |

The FAD results show that the reactions approached their targeted equilibria, to produce a canola oil with less than or about 3 weight percent saturates using a fatty acid:oil reaction weight ratio of 1.15:1 in a batch reaction. The reaction mixture of this Example 4 contains 46.5% oil. Instead of using a mixture of oleic and linoleic acids, canola oil may be transesterified with a fatty acid mixture derived from canola oil, from which saturated fatty acids have been removed. The transesterification reaction may be carried out using a canola oil unsaturated fatty acid: canola oil reaction weight ratio of 1.15:1 as described in Runs 1 and 2 of this Example, to provide a transesterified canola oil having less than 3 weight percent esterified saturated fatty acids, and an omega-9:omega-6:omega-3 esterified unsaturated fatty acid weight ratio of about 7:3:1.

Accordingly, it will be appreciated that in accordance with the present invention, novel low-saturate vegetable oils and methods for manufacturing such oils have been provided. Such methods can be used to produce oils with preselected unsaturated fatty acid compositions as a function of the composition of the starting oil and the fatty acids used in the reactions. While the invention has been described with respect to certain specific embodiments, various modifications and adaptations will be apparent from the present disclosure, which are intended to be within the scope of the following claims.

What is claimed is:

1. An enzymatic transesterification method for preparing a margarine oil having both low trans- acid and low intermediate chain fatty acid content, together with a broad margarine solids fat index melting profile and a smooth organoleptic consistency, said margarine oil comprising a blend of from about 84 to about 95 weight percent fatty acid triglycerides, from about 5 to about 15 weight percent fatty acid diglycerides and less than about one weight percent of fatty acid monoglycerides, based on the total weight of said blend, less than 3 weight percent of esterified trans- unsaturated fatty acid and less than 6 weight percent of intermediate chain saturated fatty acids, from about 25 to about 45 weight percent of esterified linoleic acid, from about 0 to about 11 weight percent of esterified linolenic acid, from about 5 to about 25 weight percent of esterified oleic acid based on the total weight of esterified fatty acids, said margarine oil also having a non-random fatty acid distribution in which esterified stearic acid is predominantly distributed in the 1-, 3- positions, while esterified unsaturated fatty acid moieties are in higher concentration at the 2- position of said glycerides within the following ranges:

|  | 1-,3- Glyceride positions weight percent | 2- Glyceride position weight percent |
| --- | --- | --- |
| Palmitic acid | 5–10 | 0–2.0 |
| Stearic acid | 50–70 | 0–5.0 |
| Oleic acid | 5–15 | 20–30 |
| Linoleic acid | 10–30 | 60–80 |
| Linolenic acid | 0–10 | 3–12 | and said margarine oil having a solid fat content profile within the following ranges:

| Temperature | Dilatometric Solid Fat Index, Percent |
| --- | --- |
| 10° C. | 7–31 |
| 21.1° C. | 3–25 |
| 26.7° C. | 0.75–10 |
| 33.3° C. | 0.5–4 |
| 38.7° C. | less than 3, | said method comprising the steps of providing a transesterification reaction mixture containing a stearic acid source material selected from the group consisting of stearic acid, stearic acid monoesters of low molecular weight monohydric alcohols, and mixtures thereof, said stearic acid source material comprising at least about 84 weight percent of stearic acid, based on the total weight of fatty acids in said stearic acid source material, and an edible liquid vegetable oil comprising at least about 80 weight percent of esterified eighteen carbon fatty acid moieties based on the total weight of the edible liquid vegetable oil triglyceride, said vegetable oil further comprising less than 7 weight percent of esterified palmitic acid in 2- glyceride position, and less than 4 weight percent of esterified stearic acid in the 2- glyceride position, at least about 20 weight percent of esterified oleic acid in each of the 1, 2 and 3 glyceride positions, at least about 20 weight percent of esterified linoleic acid, at least about 5 weight percent of esterified linolenic acid, and less than 2 weight percent of esterified stearic acid in the 2- position, transesterifying said stearic acid source material and said vegetable oil triglyceride using a 1-, 3- positionally specific lipase, at a weight ratio of stearic acid source material to the vegetable oil triglyceride in the range of from about 0.5:1 to about 2:1 to substantially equilibrate the ester groups in the 1-, 3- positions of the glyceride component with non-glyceride fatty acid components of the reaction mixture, separating transesterified free fatty acid components from glyceride components of the transesterification mixture to provide a transesterified margarine oil product and a fatty acid mixture comprising fatty acids, fatty acid monoesters or mixtures thereof released from said vegetable oil, and hydrogenating the fatty acid mixture to provide a recycle stearic acid source material for recycle reaction with said vegetable oil triglyceride.

2. A method as defined in claim 1, wherein the margarine oil has a firm bodied consistency at refrigeration temperature and a solid fat content profile of from about 23 to about 31 percent at 10° C., from about 15 to about 25 percent at 21.1° C., from about 0.75 to about 10 percent at 26.7° C., from about 0.5 to about 4 percent at 33.3° C., and from about 0 to about 3 percent at 38.7° C.

3. A method as defined in claim 1, wherein the margarine oil has a firm bodied consistency at refrigeration temperature and a solid fat content profile of from about 7 to about 12 percent at 10° C., from about 3 to about 10 percent at 21.1° C., from about 0.75 to about 8 percent at 26.7° C., from about 0.5 to about 3 percent at 33.3° C., and from about 0 to about 1.5 percent at 38.7° C.

4. A counter-current method for preparing a transesterified oil comprising the steps of providing a transesterification reaction zone containing a 1-, 3-positionally specific lipase, introducing a vegetable oil into the transesterification reaction zone to provide a triglyceride reaction stream through the reaction zone, introducing a stearic acid source material selected from the group consisting of stearic acid, stearic acid lower alkyl monoesters and mixtures thereof into the transesterification reaction zone to provide a stearic acid or stearic acid monoester reaction stream, conducting a supercritical gas or subcritical liquefied gas counter-current fluid which preferentially dissolves stearic acids and stearic acid monoesters over triglycerides under two-phase conditions through said zone counter-current to the flow of the triglyceride reaction stream, at a rate and under a pressure and temperature conditions to maintain a separate phase of said counter-current fluid containing stearic acid or stearic acid monoester through the reaction zone in intimate contact with the triglyceride reaction stream, carrying out transesterification reaction of the triglyceride stream with the stearic acid or stearic acid monoester stream in the reaction zone, withdrawing a transesterified triglyceride margarine oil stream which has been transesterified with the stearic acid source material from the reaction zone, withdrawing a counter-current fluid phase from said reaction zone counter-current to the margarine oil stream having dissolved therein transesterified stearic acids or stearic acid monoester produced by transesterification of said stearic acid source material with said vegetable oil, hydrogenating said transesterified stearic acid or stearic acid monoester to provide a hydrogenated recycle stearic acid source material, and introducing said hydrogenated recycle stearic acid source material into said reaction zone.

5. A method as defined in claim 4, wherein intermediate chain fatty acids are at least partially removed from the hydrogenated recycle stearic source material by distillation to provide a recycle stearic acid source material having less than 6 weight percent of intermediate chain saturated fatty acids.

* * * * *